United States Patent
DeMarco et al.

(10) Patent No.: US 8,658,604 B2
(45) Date of Patent: Feb. 25, 2014

(54) TEMPLATE-FIXED BETA-HAIRPIN PEPTIDOMIMETICS WITH PROTEASE INHIBITORY ACTIVITY

(75) Inventors: Steven J. DeMarco, Diegten (CH); Kerstin Moehle, Wettswil (CH); Heiko Henze, Zürich (CH); Odile Sellier, Zürich (CH); Françoise Jung, Huningue (FR); Frank Gombert, Huttingen (DE); Daniel Obrecht, Battwil (CH); Christian Ludin, Obeswil (CH)

(73) Assignees: Polyphor Ltd, Allschwil (CH); Universitat Zurich, Zurich (CH)

( * ) Notice: Subject to any disclaimer, the term of this patent is extended or adjusted under 35 U.S.C. 154(b) by 1113 days.

(21) Appl. No.: 11/816,589

(22) PCT Filed: Feb. 17, 2005

(86) PCT No.: PCT/EP2005/001622
§ 371 (c)(1),
(2), (4) Date: Oct. 5, 2007

(87) PCT Pub. No.: WO2006/087001
PCT Pub. Date: Aug. 24, 2006

(65) Prior Publication Data
US 2009/0054345 A1 Feb. 26, 2009

(51) Int. Cl.
*A61K 38/10* (2006.01)
*A61K 38/12* (2006.01)

(52) U.S. Cl.
USPC .......... 514/21.5; 514/21.1; 530/327; 530/317

(58) Field of Classification Search
None
See application file for complete search history.

(56) References Cited

U.S. PATENT DOCUMENTS 7,786,078 B2 * 8/2010 Zumbrunn et al. ............ 514/3.8

FOREIGN PATENT DOCUMENTS

| WO | WO 02/070547 A | | 9/2002 |
|---|---|---|---|
| WO | WO-03/054000 | * | 7/2003 |
| WO | WO 03/054000 | | 7/2003 |
| WO | WO 2004/018503 A | | 3/2004 |
| WO | WO 2004/033489 A | | 4/2004 |
| WO | WO 2004/096838 A | | 11/2004 |
| WO | WO 2004/096839 A | | 11/2004 |

OTHER PUBLICATIONS

Descours, ChemBioChem, 2002, 3, 318-323.*
Korsinczky, Current Protein and Peptide Science, 2004, 5, 351-364.*

* cited by examiner

*Primary Examiner* — Satyanarayana R Gudibande
(74) *Attorney, Agent, or Firm* — Hoffmann & Baron, LLP

(57) ABSTRACT

Template-fixed β-hairpin peptidomimetics of the general formulae

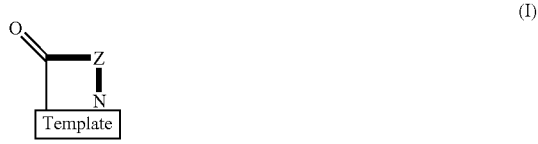

(I)

wherein Z is a chain of 11 α-amino acid residues which, depending on their positions in the chain (counted starting from the N-terminal amino acid) are Gly, or Pro, or Pro (4NHCOPhe), or of certain types which, as the remaining symbols in the above formula, are defined in the description and the claims, and salts thereof, have the property to inhibit proteases, in particular serine proteases, especially Cathepsin G or Elastase or Tryptase. These β-hairpin peptidomimetics can be manufactured by processes which are based on a mixed solid- and solution phase synthetic strategy.

35 Claims, No Drawings

SEQUENCE LISTING

<160> NUMBER OF SEQ ID NOS: 196

<210> SEQ ID NO 1
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 1

Phe Cys Thr Lys Ser Glu Pro Pro Ile Cys Thr
1               5                   10

<210> SEQ ID NO 2
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 2

Phe Cys Thr Lys Ser Asp Pro Pro Ile Cys Asp
1               5                   10

<210> SEQ ID NO 3
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 3

Phe Cys Thr Lys Ser Asp Pro Pro Ile Cys Asn
1               5                   10

<210> SEQ ID NO 4
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 4

Phe Cys Thr Lys Ser Asp Pro Pro Ile Cys Ser
1               5                   10

```
<210> SEQ ID NO 5
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 5

Phe Cys Thr Lys Ser Asp Pro Pro Ile Cys Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 6

Tyr Cys Thr Lys Ser Asp Pro Pro Ile Cys Thr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: core sequence of beta-hairpin moiety

<400> SEQUENCE: 7

Arg Glu Thr Lys Ser Asp Pro Pro Ile Arg Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (10)..(10)
<223> OTHER INFORMATION: Nle

<400> SEQUENCE: 8

Arg Xaa Thr Lys Ser Asp Pro Pro Ile Xaa Phe
1               5                   10

<210> SEQ ID NO 9
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 4AmPhe
<220> FEATURE:
<221> NAME/KEY: DISULFID
<222> LOCATION: (2)..(10)
```

```
<400> SEQUENCE: 9

Xaa Cys Thr Lys Ser Asp Pro Pro Ile Cys Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 10

Xaa Cys Thr Lys Ser Asp Pro Pro Ile Cys Ser
1               5                   10

<210> SEQ ID NO 11
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 11

Xaa Cys Thr Lys Ser Asp Pro Pro Ile Cys Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 12

Xaa Cys Thr Lys Ser Asp Pro Pro Ile Cys Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 2Cl-Phe
<220> FEATURE:
<221> NAME/KEY: DISULFID
<222> LOCATION: (2)..(10)
```

```
<400> SEQUENCE: 13

Xaa Cys Thr Lys Ser Asp Pro Pro Ile Cys Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 14

Ile Cys Thr Lys Ser Asp Pro Ala Ile Cys Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<223> OTHER INFORMATION: Nle
<220> FEATURE:
<221> NAME/KEY: MOD_RES
<222> LOCATION: (9)..(9)
<223> OTHER INFORMATION: Nle

<400> SEQUENCE: 15

Phe Cys Thr Lys Ser Asp Pro Pro Xaa Cys Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 16

Phe Cys Thr Lys Ser Asp Pro Pro Xaa Cys Ser
1               5                   10

<210> SEQ ID NO 17
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 17

Ile Cys Thr Lys Ser Asp Pro Pro Gln Cys Arg
1               5                   10

<210> SEQ ID NO 18
```

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 18

Ile Cys Thr Lys Ser Asp Pro Pro Tyr Cys Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Nle

<400> SEQUENCE: 19

Ile Cys Thr Lys Ser Asp Pro Pro Xaa Cys Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 20

Ile Cys Thr Lys Ser Asp Pro Pro Xaa Cys Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 21

Phe Cys Thr Lys Ser Glu Pro Pro Ile Cys Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
```

```
<220> FEATURE:
<221> NAME/KEY: MOD_RES
<222> LOCATION: (4)..(4)
<223> OTHER INFORMATION: Nle

<400> SEQUENCE: 22

Ile Cys Thr Xaa Ser Asp Pro Pro Ile Cys Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (4)..(4)
<223> OTHER INFORMATION: Nle

<400> SEQUENCE: 23

Phe Cys Thr Xaa Ser Asp Pro Pro Ile Cys Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (5)..(5)
<223> OTHER INFORMATION: AlloThr

<400> SEQUENCE: 24

Phe Cys Thr Lys Xaa Asp Pro Pro Ile Cys Ser
1               5                   10

<210> SEQ ID NO 25
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (5)..(5)
<223> OTHER INFORMATION: Dpr

<400> SEQUENCE: 25

Phe Cys Thr Lys Xaa Asp Pro Pro Ile Cys Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
```

```
<400> SEQUENCE: 26

Tyr Cys Thr Lys Ser Asp Pro Pro Ile Cys Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 27

Xaa Cys Thr Lys Ser Asp Pro Pro Ile Cys Asn
1               5                   10

<210> SEQ ID NO 28
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 28

Xaa Cys Thr Lys Ser Asp Pro Pro Ile Cys Thr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 29

Xaa Cys Thr Lys Ser Asp Pro Pro Ile Cys Asp
1               5                   10

<210> SEQ ID NO 30
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
```

```
<400> SEQUENCE: 30

Xaa Cys Thr Lys Ser Asp Pro Pro Ile Cys Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 4AmPhe
<220> FEATURE:
<221> NAME/KEY: DISULFID
<222> LOCATION: (2)..(10)

<400> SEQUENCE: 31

Xaa Cys Thr Lys Ser Asp Pro Pro Ile Cys Asn
1               5                   10

<210> SEQ ID NO 32
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 4AmPhe
<220> FEATURE:
<221> NAME/KEY: DISULFID
<222> LOCATION: (2)..(10)

<400> SEQUENCE: 32

Xaa Cys Thr Lys Ser Asp Pro Pro Ile Cys Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Cha
<220> FEATURE:
<221> NAME/KEY: DISULFID
<222> LOCATION: (2)..(10)

<400> SEQUENCE: 33

Xaa Cys Thr Lys Ser Asp Pro Pro Ile Cys Asn
1               5                   10

<210> SEQ ID NO 34
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Cha
<220> FEATURE:
<221> NAME/KEY: DISULFID
<222> LOCATION: (2)..(10)
```

```
<400> SEQUENCE: 34

Xaa Cys Thr Lys Ser Asp Pro Pro Ile Cys Thr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Cha
<220> FEATURE:
<221> NAME/KEY: DISULFID
<222> LOCATION: (2)..(10)

<400> SEQUENCE: 35

Xaa Cys Thr Lys Ser Asp Pro Pro Ile Cys Asp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Cha
<220> FEATURE:
<221> NAME/KEY: DISULFID
<222> LOCATION: (2)..(10)

<400> SEQUENCE: 36

Xaa Cys Thr Lys Ser Asp Pro Pro Ile Cys Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 37

Xaa Cys Thr Lys Ser Asp Pro Pro Ile Cys Asn
1               5                   10

<210> SEQ ID NO 38
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)
```

-continued

<400> SEQUENCE: 38

Xaa Cys Thr Lys Ser Asp Pro Pro Ile Cys Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 39

Xaa Cys Thr Lys Ser Asp Pro Pro Ile Cys Asp
1               5                   10

<210> SEQ ID NO 40
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 40

Xaa Cys Thr Lys Ser Asp Pro Pro Ile Cys Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 41

Xaa Cys Thr Lys Ser Asp Pro Pro Ile Cys Asn
1               5                   10

<210> SEQ ID NO 42
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

```
<400> SEQUENCE: 42

Xaa Cys Thr Lys Ser Asp Pro Pro Ile Cys Thr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 43

Xaa Cys Thr Lys Ser Asp Pro Pro Ile Cys Asp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 44

Xaa Cys Thr Lys Ser Asp Pro Pro Ile Cys Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 2Cl-Phe
<220> FEATURE:
<221> NAME/KEY: DISULFID
<222> LOCATION: (2)..(10)

<400> SEQUENCE: 45

Xaa Cys Thr Lys Ser Asp Pro Pro Ile Cys Asn
1               5                   10

<210> SEQ ID NO 46
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 46

Phe Cys Thr Lys Ser Asp Pro Pro Ile Cys Ser
```

```
<210> SEQ ID NO 47
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 47

Phe Cys Thr Lys Ser Asp Pro Pro Ile Cys Ser
1               5                   10

<210> SEQ ID NO 48
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 48

Phe Cys Thr Lys Ser Asp Pro Pro Ile Cys Ser
1               5                   10

<210> SEQ ID NO 49
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 49

Phe Cys Thr Lys Ser Asp Pro Pro Ile Cys Ser
1               5                   10

<210> SEQ ID NO 50
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 50

Phe Cys Thr Lys Ser Asp Pro Pro Ile Cys Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 51

Phe Cys Thr Lys Ser Asp Pro Pro Ile Cys Ser
```

<210> SEQ ID NO 52
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 52

Ile Cys Thr Lys Ser Asp Pro Ala Ile Cys Arg
1               5                   10

<210> SEQ ID NO 53
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Nle

<400> SEQUENCE: 53

Phe Cys Thr Lys Ser Asp Pro Pro Xaa Cys Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 54

Phe Cys Thr Lys Ser Asp Pro Pro Xaa Cys Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 55

Ile Cys Thr Lys Ser Asp Pro Pro Gln Cys Arg
1               5                   10

<210> SEQ ID NO 56
<211> LENGTH: 11
<212> TYPE: PRT
<213> ORGANISM: Artificial Sequence
<220> FEATURE:

```
<223> OTHER INFORMATION: core sequence of beta-hairpin moiety
<220> FEATURE:
<221> NAME/KEY: DISULFID
<222> LOCATION: (2)..(10)

<400> SEQUENCE: 56

Ile Cys Thr Lys Ser Asp Pro Pro Tyr Cys Arg
1               5                   10

<210> SEQ ID NO 57
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Nle

<400> SEQUENCE: 57

Ile Cys Thr Lys Ser Asp Pro Pro Xaa Cys Arg
1               5                   10

<210> SEQ ID NO 58
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 58

Ile Cys Thr Lys Ser Asp Pro Pro Xaa Cys Arg
1               5                   10

<210> SEQ ID NO 59
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 59

Ile Cys Thr Xaa Ser Asp Pro Pro Ile Cys Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
```

```
<222> LOCATION: (2)..(10)
<220> FEATURE:
<221> NAME/KEY: MOD_RES
<222> LOCATION: (4)..(4)
<223> OTHER INFORMATION: Nle

<400> SEQUENCE: 60

Phe Cys Thr Xaa Ser Asp Pro Pro Ile Cys Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 61

Trp Cys Thr Lys Ser Asp Pro Pro Ile Cys Ser
1               5                   10

<210> SEQ ID NO 62
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 1-Nal
<220> FEATURE:
<221> NAME/KEY: DISULFID
<222> LOCATION: (2)..(10)

<400> SEQUENCE: 62

Xaa Cys Thr Lys Ser Asp Pro Pro Ile Cys Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Nle

<400> SEQUENCE: 63

Xaa Cys Thr Lys Ser Asp Pro Pro Xaa Cys Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
```

```
<222> LOCATION: (2)..(10)

<400> SEQUENCE: 64

Phe Cys Thr Lys Ser Asp Pro Pro Ile Cys Ser
1               5                   10

<210> SEQ ID NO 65
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)

<400> SEQUENCE: 65

Xaa Cys Thr Lys Ser Asp Pro Pro Tyr Cys Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)
<223> OTHER INFORMATION: Chg
<220> FEATURE:
<221> NAME/KEY: MOD_RES
<222> LOCATION: (9)..(9)
<223> OTHER INFORMATION: Cha

<400> SEQUENCE: 66

Xaa Cys Thr Lys Ser Asp Pro Pro Xaa Cys Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)
<220> FEATURE:
<221> NAME/KEY: MOD_RES
<222> LOCATION: (5)..(5)
<223> OTHER INFORMATION: AlloThr

<400> SEQUENCE: 67

Xaa Cys Thr Lys Xaa Asp Pro Pro Tyr Cys Tyr
1               5                   10

<210> SEQ ID NO 68
<211> LENGTH: 11
<212> TYPE: PRT
```

```
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 68

Phe Cys Thr Lys Ser Asp Pro Pro Ile Cys Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 69

Phe Cys Thr Lys Ser Asp Pro Pro Ile Cys Ser
1               5                   10

<210> SEQ ID NO 70
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: 4AmPhe
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 70

Xaa Cys Thr Lys Ser Asp Pro Pro Xaa Cys Asn
1               5                   10

<210> SEQ ID NO 71
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Chg
<220> FEATURE:
<221> NAME/KEY: DISULFID
<222> LOCATION: (2)..(10)
<220> FEATURE:
<221> NAME/KEY: MOD_RES
<222> LOCATION: (9)..(9)
<223> OTHER INFORMATION: Cha

<400> SEQUENCE: 71

Xaa Cys Thr Lys Ser Asp Pro Pro Xaa Cys Arg
1               5                   10

<210> SEQ ID NO 72
<211> LENGTH: 11
<212> TYPE: PRT
```

<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 72

Phe Cys Thr Lys Ser Asp Pro Pro Ile Cys Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 73

Phe Cys Thr Lys Ser Asp Pro Pro Ile Cys Ser
1               5                   10

<210> SEQ ID NO 74
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 74

Phe Cys Thr Lys Ser Asp Pro Pro Ile Cys Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 75

Arg Cys Thr Lys Ser Asp Pro Pro Ile Cys Phe
1               5                   10

<210> SEQ ID NO 76
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 76

Ile Cys Thr Ala Ser Leu Pro Pro Gln Cys Tyr
1               5                   10

<210> SEQ ID NO 77
<211> LENGTH: 11
<212> TYPE: PRT

```
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 77

Xaa Cys Thr Thr Ser Ile Pro Pro Tyr Cys Tyr
 1               5                  10

<210> SEQ ID NO 78
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (4)..(4)
<223> OTHER INFORMATION: Abu

<400> SEQUENCE: 78

Xaa Cys Thr Xaa Ser Ile Pro Pro Gln Cys Tyr
 1               5                  10

<210> SEQ ID NO 79
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Nle

<400> SEQUENCE: 79

Xaa Cys Thr Ala Ser Xaa Pro Pro Gln Cys Tyr
 1               5                  10

<210> SEQ ID NO 80
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
```

```
<222> LOCATION: (6)..(6)
<223> OTHER INFORMATION: Aoc

<400> SEQUENCE: 80

Xaa Cys Thr Ala Ser Xaa Pro Pro Gln Cys Tyr
 1               5                  10

<210> SEQ ID NO 81
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 81

Xaa Cys Thr Ala Ser Xaa Pro Pro Gln Cys Tyr
 1               5                  10

<210> SEQ ID NO 82
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 82

Xaa Cys Thr Ala Ser Xaa Pro Pro Gln Cys Tyr
 1               5                  10

<210> SEQ ID NO 83
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: hLeu

<400> SEQUENCE: 83

Xaa Cys Thr Ala Ser Xaa Pro Pro Gln Cys Tyr
 1               5                  10
```

```
<210> SEQ ID NO 84
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Chg

<400> SEQUENCE: 84

Xaa Cys Thr Ala Ser Xaa Pro Pro Gln Cys Tyr
 1               5                  10

<210> SEQ ID NO 85
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: t-BuAla

<400> SEQUENCE: 85

Xaa Cys Thr Ala Ser Xaa Pro Pro Gln Cys Tyr
 1               5                  10

<210> SEQ ID NO 86
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<223> OTHER INFORMATION: Nle

<400> SEQUENCE: 86

Xaa Cys Ala Ala Ser Ile Pro Pro Gln Cys Tyr
 1               5                  10

<210> SEQ ID NO 87
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
```

```
<220> FEATURE:
<221> NAME/KEY: DISULFID
<222> LOCATION: (2)..(10)
<220> FEATURE:
<221> NAME/KEY: MOD_RES
<222> LOCATION: (3)..(3)
<223> OTHER INFORMATION: Abu

<400> SEQUENCE: 87

Xaa Cys Xaa Ala Ser Ile Pro Pro Gln Cys Tyr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (8)..(8)
<223> OTHER INFORMATION: Pro(4NHCOPhe)

<400> SEQUENCE: 88

Xaa Cys Thr Ala Ser Ile Pro Xaa Gln Cys Tyr
1               5                   10

<210> SEQ ID NO 89
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 89

Xaa Cys Thr Ala Ser Ile Pro Pro Phe Cys Tyr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 90

Xaa Cys Thr Ala Ser Ile Pro Pro Gln Cys Phe
1               5                   10

<210> SEQ ID NO 91
<211> LENGTH: 11
```

```
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 91

Xaa Cys Thr Ala Ser Ile Pro Pro Gln Cys Gln
1               5                   10

<210> SEQ ID NO 92
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 92

Xaa Cys Thr Ala Ser Ile Pro Pro Gln Cys Arg
1               5                   10

<210> SEQ ID NO 93
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 93

Xaa Cys Thr Ala Ser Ile Pro Pro Gln Cys Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: Nle

<400> SEQUENCE: 94

Xaa Cys Thr Ala Ser Ile Pro Pro Gln Cys Xaa
1               5                   10
```

```
<210> SEQ ID NO 95
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: 2-Nal

<400> SEQUENCE: 95

Xaa Cys Thr Ala Ser Ile Pro Pro Gln Cys Xaa
1               5                   10

<210> SEQ ID NO 96
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: 2Cl-Phe

<400> SEQUENCE: 96

Xaa Cys Thr Ala Ser Ile Pro Pro Gln Cys Xaa
1               5                   10

<210> SEQ ID NO 97
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: Cha

<400> SEQUENCE: 97

Xaa Cys Thr Ala Ser Ile Pro Pro Gln Cys Xaa
1               5                   10

<210> SEQ ID NO 98
<211> LENGTH: 11
<212> TYPE: PRT
<213> ORGANISM: Artificial Sequence
<220> FEATURE:
<223> OTHER INFORMATION: core sequence of beta-hairpin moiety
```

```
<220> FEATURE:
<221> NAME/KEY: MOD_RES
<222> LOCATION: (1)..(1)
<223> OTHER INFORMATION: Nle
<220> FEATURE:
<221> NAME/KEY: DISUL

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)

<400> SEQUENCE: 102

Xaa Cys Thr Ala Ser Ile Pro Pro Gln Cys Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 103

Xaa Cys Thr Ala Ser Ile Pro Pro Gln Cys Tyr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 104

Xaa Glu Thr Ala Ser Ile Pro Pro Gln Lys Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 105

Xaa Glu Thr Ala Ser Ile Pro Pro Gln Arg Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
```

<221> NAME/KEY: MOD_RES
<222> LOCATION: (1)..(1)
<223> OTHER INFORMATION: Nle

<400> SEQUENCE: 106

Xaa Thr Thr Ala Ser Ile Pro Pro Gln Lys Tyr
1               5                   10

<210> SEQ ID NO 107
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 107

Xaa Gln Thr Ala Ser Ile Pro Pro Gln Arg Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 108

Xaa Thr Thr Ala Ser Ile Pro Pro Gln Met Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 109

Xaa Gln Thr Ala Ser Ile Pro Pro Gln Thr Tyr
1               5                   10

<210> SEQ ID NO 110
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 110

Xaa Thr Thr Ala Ser Ile Pro Pro Gln Gln Tyr
1               5                   10

<210> SEQ ID NO 111
<211> LENGTH: 11

```
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle

<400> SEQUENCE: 111

Xaa Gln Thr Ala Ser Ile Pro Pro Gln Ser Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: C5al

<400> SEQUENCE: 112

Xaa Cys Thr Ala Ser Xaa Pro Pro Gln Cys Tyr
1               5                   10

<210> SEQ ID NO 113
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 113

Xaa Cys Thr Ala Ser Leu Pro Pro Tyr Cys Tyr
1               5                   10

<210> SEQ ID NO 114
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 114

Ile Cys Thr Ala Ser Leu Pro Pro Tyr Cys Tyr
1               5                   10

<210> SEQ ID NO 115
<211> LENGTH: 11
<212> TYPE: PRT
<213> ORGANISM: Artificial Sequence
<220> FEATURE:
```

-continued

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 115

Xaa Cys Thr Ala Ser Ile Pro Pro Gln Cys Tyr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 116

Xaa Cys Thr Ala Ser Ile Pro Pro Gln Cys Tyr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 117

Xaa Cys Thr Ala Ser Ile Pro Pro Gln Cys Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 118

Xaa Cys Thr Ala Ser Ile Pro Pro Gln Cys Tyr
1               5                   10

<210> SEQ ID NO 119
<211> LENGTH: 11
<212> TYPE: PRT
<213> ORGANISM: Artificial Sequence
<220> FEATURE:
```

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 119

Xaa Cys Thr Ala Ser Ile Pro Pro Gln Cys Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 120

Xaa Cys Thr Ala Ser Ile Pro Pro Gln Cys Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 121

Xaa Cys Thr Ala Ser Ile Pro Pro Gln Cys Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 122

Xaa Cys Thr Ala Ser Ile Pro Pro Gln Cys Tyr
1               5                   10

<210> SEQ ID NO 123
<211> LENGTH: 11
<212> TYPE: PRT
<213> ORGANISM: Artificial Sequence
<220> FEATURE:
```

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 123

Xaa Cys Thr Ala Ser Ile Pro Pro Gln Cys Tyr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 124

Xaa Cys Thr Ala Ser Ile Pro Pro Gln Cys Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 125

Xaa Cys Thr Ala Ser Ile Pro Pro Gln Cys Tyr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 126

Xaa Cys Thr Ala Ser Ile Pro Pro Gln Cys Tyr
1               5                   10

<210> SEQ ID NO 127
<211> LENGTH: 11
<212> TYPE: PRT
<213> ORGANISM: Artificial Sequence
<220> FEATURE:
```

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 127

Xaa Cys Thr Ala Ser Ile Pro Pro Gln Cys Tyr
 1               5                  10

<210> SEQ ID NO 128
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 128

Xaa Cys Thr Ala Ser Ile Pro Pro Gln Cys Tyr
 1               5                  10

<210> SEQ ID NO 129
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 129

Xaa Cys Thr Ala Ser Xaa Pro Pro Gln Cys Gln
 1               5                  10

<210> SEQ ID NO 130
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 130

Xaa Cys Thr Ala Ser Ile Pro Pro Gln Cys Tyr
 1               5                  10

<210> SEQ ID NO 131
```

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 131

Xaa Cys Thr Ala Ser Ile Pro Pro Gln Cys Gln
1               5                   10

<210> SEQ ID NO 132
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe

<400> SEQUENCE: 132

Xaa Glu Thr Ala Ser Ile Pro Pro Gln Lys Tyr
1               5                   10

<210> SEQ ID NO 133
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 133

Xaa Cys Thr Ala Ser Xaa Pro Pro Gln Cys Gln
1               5                   10

<210> SEQ ID NO 134
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe

<400> SEQUENCE: 134

Xaa Thr Thr Ala Ser Ile Pro Pro Gln Gln Tyr
1               5                   10

<210> SEQ ID NO 135
<211> LENGTH: 11
<212> TYPE: PRT
```

```
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: OctG

<400> SEQUENCE: 135

Xaa Thr Thr Ala Ser Xaa Pro Pro Gln Gln Tyr
1               5                   10

<210> SEQ ID NO 136
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: Phg

<400> SEQUENCE: 136

Xaa Cys Thr Ala Ser Ile Pro Pro Gln Cys Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 137

Xaa Cys Thr Ala Ser Ile Pro Pro Gln Cys Phe
1               5                   10

<210> SEQ ID NO 138
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (8)..(8)
<223> OTHER INFORMATION: Pro(4NHCOPhe)
```

```
<400> SEQUENCE: 138

Xaa Cys Thr Ala Ser Ile Pro Xaa Gln Cys Tyr
1               5                   10

<210> SEQ ID NO 139
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (6)..(6)
<223> OTHER INFORMATION: Cha

<400> SEQUENCE: 139

Xaa Thr Thr Ala Ser Xaa Pro Pro Gln Gln Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Chg

<400> SEQUENCE: 140

Xaa Cys Thr Ala Ser Xaa Pro Pro Gln Cys Tyr
1               5                   10

<210> SEQ ID NO 141
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 141

Xaa Cys Thr Ala Ser Xaa Pro Pro Gln Cys Tyr
1               5                   10

<210> SEQ ID NO 142
<211> LENGTH: 11
<212> TYPE: PRT
<213> ORGANISM: Artificial Sequence
<220> FEATURE:
```

```
-continued

<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe

<400> SEQUENCE: 142

Xaa Gln Thr Ala Ser Ile Pro Pro Gln Thr Tyr
1               5                   10

<210> SEQ ID NO 143
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 143

Xaa Cys Thr Ala Ser Ile Pro Pro Gln Cys Gln
1               5                   10

<210> SEQ ID NO 144
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (11)..(11)
<223> OTHER INFORMATION: 2Cl-Phe

<400> SEQUENCE: 144

Xaa Cys Thr Ala Ser Ile Pro Pro Gln Cys Xaa
1               5                   10

<210> SEQ ID NO 145
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)

<400> SEQUENCE: 145

Xaa Cys Thr Ala Ser Ile Pro Pro Gln Cys Phe
1               5                   10

<210> SEQ ID NO 146
<211> LENGTH: 11
<212> TYPE: PRT
<213> ORGANISM: Artificial Sequence
```

```
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 146

Xaa Cys Thr Ala Ser Ile Pro Pro Gln Cys Phe
1               5                   10

<210> SEQ ID NO 147
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG

<400> SEQUENCE: 147

Xaa Thr Thr Ala Ser Ile Pro Pro Gln Gln Tyr
1               5                   10

<210> SEQ ID NO 148
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 148

Xaa Cys Thr Ala Ser Xaa Pro Pro Gln Cys Gln
1               5                   10

<210> SEQ ID NO 149
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)

<400> SEQUENCE: 149

Xaa Cys Thr Ala Ser Ile Pro Pro Gln Cys Gln
1               5                   10

<210> SEQ ID NO 150
<211> LENGTH: 11
<212> TYPE: PRT
```

```
<213> ORGANISM: Artificial Sequence
<220> FEATURE:
<223> OTHER INFORMATION: core sequence of beta-hairpin moiety
<220> FEATURE:
<221>

```
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 153

Xaa Cys Thr Ala Ser Xaa Pro Pro Gln Cys Gln
1               5                   10

<210> SEQ ID NO 154
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG

<400> SEQUENCE: 154

Xaa Gln Thr Ala Ser Ile Pro Pro Gln Thr Tyr
1               5                   10

<210> SEQ ID NO 155
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 155

Xaa Cys Thr Ala Ser Xaa Pro Pro Gln Cys Phe
1               5                   10

<210> SEQ ID NO 156
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG

<400> SEQUENCE: 156

Xaa Glu Thr Ala Ser Ile Pro Pro Gln Lys Tyr
1               5                   10

<210> SEQ ID NO 157
<211> LENGTH: 11
<212> TYPE: PRT
<213> ORGANISM: Artificial Sequence
<220> FEATURE:
```

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 157

Xaa Cys Thr Ala Ser Xaa Pro Pro Gln Cys Phe
1               5                   10

<210> SEQ ID NO 158
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 158

Xaa Cys Thr Ala Ser Xaa Pro Pro Gln Cys Gln
1               5                   10

<210> SEQ ID NO 159
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 159

Xaa Cys Thr Ala Ser Xaa Pro Pro Gln Cys Gln
1               5                   10

<210> SEQ ID NO 160
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)
```

```
<220> FEATURE:
<221> NAME/KEY: MOD_RES
<222> LOCATION: (6)..(6)
<223> OTHER INFORMATION: Cha
<220> FEATURE:
<221> NAME/KEY: MOD_RES
<222> LOCATION: (8)..(8)
<223> OTHER INFORMATION: Proo(4NHCOPhe)

<400> SEQUENCE: 160

Xaa Cys Thr Ala Ser Xaa Pro Xaa Gln Cys Gln
1               5                   10

<210> SEQ ID NO 161
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 161

Xaa Cys Thr Ala Ser Xaa Pro Pro Gln Cys Tyr
1               5                   10

<210> SEQ ID NO 162
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 162

Xaa Cys Thr Ala Ser Xaa Pro Pro Gln Cys Tyr
1               5                   10

<210> SEQ ID NO 163
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG
```

```
<400> SEQUENCE: 163

Xaa Cys Thr Ala Ser Xaa Pro Pro Gln Cys Tyr
1               5                   10

<210> SEQ ID NO 164
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 164

Xaa Cys Thr Ala Ser Xaa Pro Pro Gln Cys Gln
1               5                   10

<210> SEQ ID NO 165
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)

<400> SEQUENCE: 165

Xaa Cys Thr Ala Ser Ile Pro Pro Gln Cys Tyr
1               5                   10

<210> SEQ ID NO 166
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 166

Xaa Cys Thr Ala Ser Ile Pro Pro Gln Cys Tyr
1               5                   10

<210> SEQ ID NO 167
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
```

```
<223> OTHER INFORMATION: Nle
<220> FEATURE:
<221> NAME/KEY: DISULFID
<222> LOCATION: (2)..(10)

<400> SEQUENCE: 167

Xaa Cys Thr Ala Ser Ile Pro Pro Gln Cys Tyr
 1               5                  10

<210> SEQ ID NO 168
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 168

Xaa Cys Thr Ala Ser Ile Pro Pro Gln Cys Tyr
 1               5                  10

<210> SEQ ID NO 169
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 169

Xaa Cys Thr Ala Ser Xaa Pro Pro Gln Cys Tyr
 1               5                  10

<210> SEQ ID NO 170
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 170

Xaa Cys Thr Ala Ser Xaa Pro Pro Gln Cys Tyr
 1               5                  10

<210> SEQ ID NO 171
```

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 171

Xaa Cys Thr Ala Ser Xaa Pro Pro Gln Cys Xaa
1               5                   10

<210> SEQ ID NO 172
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha
<220> FEATURE:
<221> NAME/KEY: MOD_RES
<222> LOCATION: (11)..(11)
<223> OTHER INFORMATION: Cha

<400> SEQUENCE: 172

Xaa Cys Thr Ala Ser Xaa Pro Pro Gln Cys Xaa
1               5                   10

<210> SEQ ID NO 173
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 173

Xaa Cys Thr Ala Ser Ile Pro Pro Gln Cys Tyr
1               5                   10

<210> SEQ ID NO 174
<211> LENGTH: 11
<212> TYPE: PRT
<213> ORGANISM: Artificial Sequence
<220> FEATURE:
```

```
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: hPhe
<220> FEATURE:
<221> NAME/KEY: DISULFID
<222> LOCATION: (2)..(10)

<400> SEQUENCE: 174

Xaa Cys Thr Ala Ser Ile Pro Pro Gln Cys Tyr
1               5                   10

<210> SEQ ID NO 175
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha
<220> FEATURE:
<221> NAME/KEY: MOD_RES
<222> LOCATION: (11)..(11)
<223> OTHER INFORMATION: 2Cl-Phe

<400> SEQUENCE: 175

Xaa Cys Thr Ala Ser Xaa Pro Pro Gln Cys Xaa
1               5                   10

<210> SEQ ID NO 176
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha
<220> FEATURE:
<221> NAME/KEY: MOD_RES
<222> LOCATION: (8)..(8)
<223> OTHER INFORMATION: Pro(4NHCOPhe)

<400> SEQUENCE: 176

Xaa Cys Thr Ala Ser Xaa Pro Xaa Gln Cys Gln
1               5                   10

<210> SEQ ID NO 177
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
```

```
<223> OTHER INFORMATION: OctG
<220> FEATURE:
<221> NAME/KEY: DISULFID
<222> LOCATION: (2)..(10)

<400> SEQUENCE: 177

Xaa Cys Thr Ala Ser Ile Pro Pro Gln Cys Tyr
1               5                   10

<210> SEQ ID NO 178
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: OctG
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: OctG

<400> SEQUENCE: 178

Xaa Cys Thr Ala Ser Xaa Pro Pro Gln Cys Gln
1               5                   10

<210> SEQ ID NO 179
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 179

Xaa Cys Thr Ala Ser Ile Pro Pro Gln Cys Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 180

Ile Cys Thr Lys Ser Leu Pro Pro Ile Cys Arg
1               5                   10

<210> SEQ ID NO 181
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
```

```
<220> FEATURE:
<221> NAME/KEY: MOD_RES
<222> LOCATION: (6)..(6)
<223> OTHER INFORMATION: hPhe

<400> SEQUENCE: 181

Ile Cys Thr Lys Ser Xaa Pro Pro Ile Cys Arg
1               5                   10

<210> SEQ ID NO 182
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
<220> FEATURE:
<221> NAME/KEY: MOD_RES
<222> LOCATION: (6)..(6)
<223> OTHER INFORMATION: Cha

<400> SEQUENCE: 182

Ile Cys Thr Lys Ser Xaa Pro Pro Ile Cys Arg
1               5                   10

<210> SEQ ID NO 183
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 183

Ile Cys Thr Lys Ser Tyr Pro Pro Ile Cys Arg
1               5                   10

<210> SEQ ID NO 184
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 184

Phe Cys Thr Lys Ser Leu Pro Pro Ile Cys Arg
1               5                   10

<210> SEQ ID NO 185
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 185

Ile Cys Thr Lys Ser Leu Pro Pro Arg Cys Arg
1               5                   10

<210> SEQ ID NO 186
```

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 186

Ile Cys Thr Lys Ser Leu Pro Pro Lys Cys Arg
1               5                   10

<210> SEQ ID NO 187
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 187

Ile Cys Thr Lys Ser Leu Pro Pro His Cys Arg
1               5                   10

<210> SEQ ID NO 188
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 188

Ile Cys Thr Lys Ser Leu Pro Pro Gln Cys Arg
1               5                   10

<210> SEQ ID NO 189
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 189

Ile Cys Thr Lys Ser Leu Pro Pro Thr Cys Arg
1               5                   10

<210> SEQ ID NO 190
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 190

Ile Cys Thr Lys Ser Leu Pro Pro Arg Cys Lys
1               5                   10

<210> SEQ ID NO 191
```

```
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 191

Leu Cys Thr Lys Ser Leu Pro Pro Lys Cys Arg
1               5                   10

<210> SEQ ID NO 192
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Nle
<220> FEATURE:
<221> NAME/KEY: DISULFID
<222> LOCATION: (2)..(10)

<400> SEQUENCE: 192

Xaa Cys Thr Lys Ser Leu Pro Pro Lys Cys Arg
1               5                   10

<210> SEQ ID NO 193
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: MOD_RES
<222> LOCATION: (1)..(1)
<223> OTHER INFORMATION: Cha
<220> FEATURE:
<221> NAME/KEY: DISULFID
<222> LOCATION: (2)..(10)

<400> SEQUENCE: 193

Xaa Cys Thr Lys Ser Leu Pro Pro Lys Cys Arg
1               5                   10

<210> SEQ ID NO 194
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 194

Tyr Cys Thr Lys Ser Leu Pro Pro Lys Cys Arg
1               5                   10

<210> SEQ ID NO 195
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)
```

```
<400> SEQUENCE: 195

Trp Cys Thr Lys Ser Leu Pro Pro Lys Cys Arg
1               5                   10

<210> SEQ ID NO 196
<211> LENGTH: 11
<212> TYPE: PRT
<213> ORGANISM: Artificial Sequence
<220> FEATURE:
<223> OTHER INFORMATION: core sequence of beta-hairpin moiety
<220> FEATURE:
<221> NAME/KEY: DISULFID
<222> LOCATION: (2)..(10)

<400> SEQUENCE: 196

Arg Cys Thr Lys Ser Leu Pro Pro Lys Cys Tyr
1               5                   10
```

TEMPLATE-FIXED BETA-HAIRPIN PEPTIDOMIMETICS WITH PROTEASE INHIBITORY ACTIVITY

CROSS-REFERENCE TO RELATED APPLICATIONS

This application is the National Stage of International Application No. PCT/EP2005/001622, filed Feb. 17, 2005, the entire contents of which are incorporated by reference herein.

FIELD OF THE INVENTION

The present invention provides template-fixed β-hairpin peptidomimetics incorporating a template-fixed chain of 11 α-amino acid residues which, depending on their position in the chain, are Gly, or Pro, or Pro(4NHCOPhe), or are of certain types, as defined hereinbelow. These template-fixed β-hairpin peptidomimetics are useful as inhibitors of protease enzymes. They are especially valuable as inhibitors of various serine proteases such as human cathepsin G, elastase, or tryptase. In addition the present invention provides an efficient process by which these compounds can, if desired, be made in library-format.

The β-hairpin peptidomimetics of the invention show improved efficacy, oral bioavailability, improved half-life and most importantly a high selectivity ratio among different serine proteases which depends on the proper choice of certain types of α-amino acid residues and their position in said chain. In addition these β-hairpin peptidomimetics show a low hemolysis on red blood cells and low cytotoxicity.

BACKGROUND OF THE INVENTION

Inhibitors of proteases are emerging with promising therapeutic uses in the treatment of diseases such as cancers (R. P. Beckett, A. Davidson, A. H. Drummond, M. Whittaker, *Drug Disc. Today* 1996, 1, 16-26; L. L. Johnson, R. Dyer, D. J. Hupe, *Curr. Opin. Chem. Biol.* 1998, 2, 466-71; D. Leung, G. Abbenante, and D. P. Fairlie, *J. Med. Chem.* 2000, 43, 305-341, T. Rockway, *Expert Opin. Ther. Patents* 2003, 13, 773-786), parasitic, fungal, and viral infections [e.g. schistosomiasis (M. M. Becker, S. A. Harrop, J. P. Dalton, B. H. Kalinna, D. P. McManus, D. P. Brindley, *J. Biol. Chem.* 1995, 270, 24496-501); *C. albicans* (C. Abad-Zapetero, R. Goldman, S. W. Muchmore, C. Hutchins, K. Stewart, J. Navaza, C. D. Payne, T. L. Ray, *Protein Sci.* 1996, 5, 640-52), HIV (A. Wlodawer, J. W. Erickson, *Annu. Rev. Biochem.* 1993, 62, 543-85; P. L. Darke, J. R. Huff, *Adv. Pharmacol.* 1994, 5, 399-454), hepatitis (J. L. Kim, K. A. Morgenstern, C. Lin, T. Fox, M. D. Dwyer, J. A. Landro, S. P. Chambers, W. Markland, C. A. Lepre, E. T. O'Malley, S. L. Harbeson, C. M. Rice, M. A. Murcko, P. R. Caron, J. A. Thomson, *Cell,* 1996, 87, 343-55; R. A. Love, H. E. Parge, J. A. Wickersham, Z. Hostomsky, N. Habuka, E. W. Moomaw, T. Adachi, Z. Hostomska, *Cell,* 1996, 87, 331-342), herpes (W. Gibson, M. R. Hall, *Drug. Des. Discov.* 1997, 15, 39-47)], and inflammatory, immunological, respiratory (P. R. Bernstein, P. D. Edwards, J. C. Williams, *Prog. Med. Chem.* 1994, 31, 59-120; T. E. Hugli, *Trends Biotechnol.* 1996, 14, 409-12,), cardiovascular (M. T. Stubbs, W. A. Bode, *Thromb. Res.* 1993, 69, 1-58; H. Fukami et al, *Current Pharmaceutical Design* 1998, 4, 439-453), and neurodegenerative defects including Alzheimer's disease (R. Vassar, B. D. Bennett, S. Babu-Kahn, S. Kahn, E. A. Mendiaz, *Science,* 1999, 286, 735-41), angiogenesis (Kaatinen M et al, *Atherosklerosis* 1996, 123 1-2, 123-131) and multiple sclerosis (Ibrahim M Z et al, *J. Neuroimmunol* 1996, 70, 131-138.

As most proteases bind their substrates in extended or β-strand conformations, good inhibitors must thus be able to mimic mimic such a conformation. β-Hairpin mimetics are thus ideally suited to lock peptide sequences in an extended conformation.

Among proteases, serine proteases constitute important therapeutic targets. Serine proteases are classified by their substrate specificity, particularly by the type of residue found at P1, as either trypsin-like (positively charged residues Lys/Arg preferred at P1), elastase-like (small hydrophobic residues Ala/Val at P1), or chymotrypsin-like (large hydrophobic residues Phe/Tyr/Leu at P1). Serine proteases for which protease-inhibitor X-ray crystal data is available on the PDB data base (PDB: www.rcsb.org/pdb) include trypsin, α-chymotrypsin, γ-chymotrypsin, human neutrophil elastase, thrombin, subtilisin, human cytomegalovirus, proteinase A, *achromobacter*, human cathepsin G, glutamic acid-specific protease, carbopeptidase D, blood coagulation factorVIIa, porcine factor 1XA, mesentericopeptidase, HCV protease, and thermitase. Other serine proteases which are of therapeutic interest include tryptase, complement convertase, hepatitis C-NS3 protease. Inhibitors of thrombin (e.g. J. L. Metha, L. Y. Chen, W. W. Nichols, C. Mattsson, D. Gustaffson, T. G. P. Saldeen, *J. Cardiovasc. Pharmacol.* 1998, 31, 345-51; C. Lila, P. Gloanec, L. Cadet, Y. Herve, J. Fournier, F. Leborgne, T. J. Verbeuren, G. DeNanteuil, *Synth. Comm.* 1998, 28, 4419-29) and factor Xa (e.g. J. P. Vacca, *Annu. Rep. Med. Chem.* 1998, 33, 81-90) are in clinical evaluation as antithrombotics, inhibitors of elastase (J. R. Williams, R. C. Falcone, C. Knee, R. L. Stein, A. M. Strimpler, B. Reaves, R. E. Giles, R. D. Krell, *Am. Rev. Respir. Dis.* 1991, 144, 875-83) are in clinical trials for emphysema and other pulmonary diseases whereas tryptase inhibitors are currently in phase II clinical trials for asthma (C. Seife, *Science* 1997, 277, 1602-3), urokinase inhibitors for breast cancer, and chymase inhibitors for heart related diseases. Finally, cathepsin G and elastase are intimately involved in the modulation of activities of cytokines and their receptors. Particularly at sites of inflammation, high concentration of cathepsin G, elastase and proteinase 3 are released from infiltrating polymorphonuclear cells in close temporal correlation to elevated levels of inflammatory cytokines, strongly indicating that these proteases are involved in the control of cytokine bioactivity and availability (U. Bank, S. Ansorge, *J. Leukoc. Biol.* 2001, 69, 177-90). Thus inhibitors of elastase and cathepsin G constitute valuable targets for novel drug candidates particularly for chronic obstructive pulmonary disease (Ohbayashi H, *Epert Opin. Investig. Drugs* 2002, 11, 965-980).

Of the many occurring proteinaceous serine protease inhibitors, one is a 14 amino acid cyclic peptide from sunflower seeds, termed sunflower trypsin inhibitor (SFTI-1) (S. Luckett, R. Santiago Garcia, J. J. Barker, A. V. Konarev, P. R. Shewry, A. R. Clarke, R. L. Brady, *J. Mol. Biol.* 1999, 290, 525-533; Y.-Q. Long, S.-L. Lee, C.-Y. Lin, I. J. Enyedy, S. Wang, P. Li, R. B. Dickson, P. P. Roller, *Biorg. & Med. Chem. Lett.* 2001, 11, 2515-2519), which shows both sequence and conformational similarity with the trypsin-reactive loop of the Bowman-Birk family of serine protease inhibitors. The inhibitor adopts a β-hairpin conformation when bound to the active site of bovine β-trypsin. SFTI-1 inhibited β-trypsin ($K_i$<0.1 nM), cathepsin G ($K_i$~0.15 nM), elastase ($K_i$~105 µM), chymotrypsin ($K_i$~7.4 µM) and thrombin ($K_i$~136 mM).

BRIEF SUMMARY OF THE INVENTION

We illustrate here an approach to inhibitor design which involves transplanting the β-hairpin loop from the naturally occurring peptide onto a hairpin-inducing template. Based on the well defined 3D-structure of the β-hairpin mimetics, libraries of compounds can be designed which ultimately can lead to novel inhibitors showing different specificity profiles towards several classes of proteases.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), and serine proteinase-inhibiting template-fixed peptidomimetics and methods for their synthesis have been described in International Patent Application WO2003/054000 A1 and in Descours A, Moehle K., Renard A, Robinson J. *ChemBioChem* 2002, 3, 318-323 but the previously disclosed molecules do not exhibit high selectivity and particularly high potency. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112).

These methods allow the synthesis and screening of large hairpin mimetic libraries, which in turn considerably facilitates structure-activity studies, and hence the discovery of new molecules with highly potent and selective serine protease inhibitory activity, oral bioavailability, low hemolytic activity to human red blood cells and low cytotoxicity.

DETAILED DESCRIPTION OF THE INVENTION

The β-hairpin peptidomimetics of the present invention are compounds of the general formula

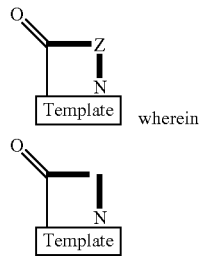

(I)

wherein is a group of one of the formulae

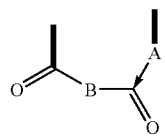

(a1)

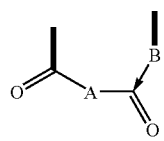

(a2)

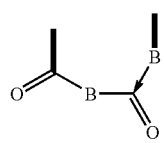

(a3)

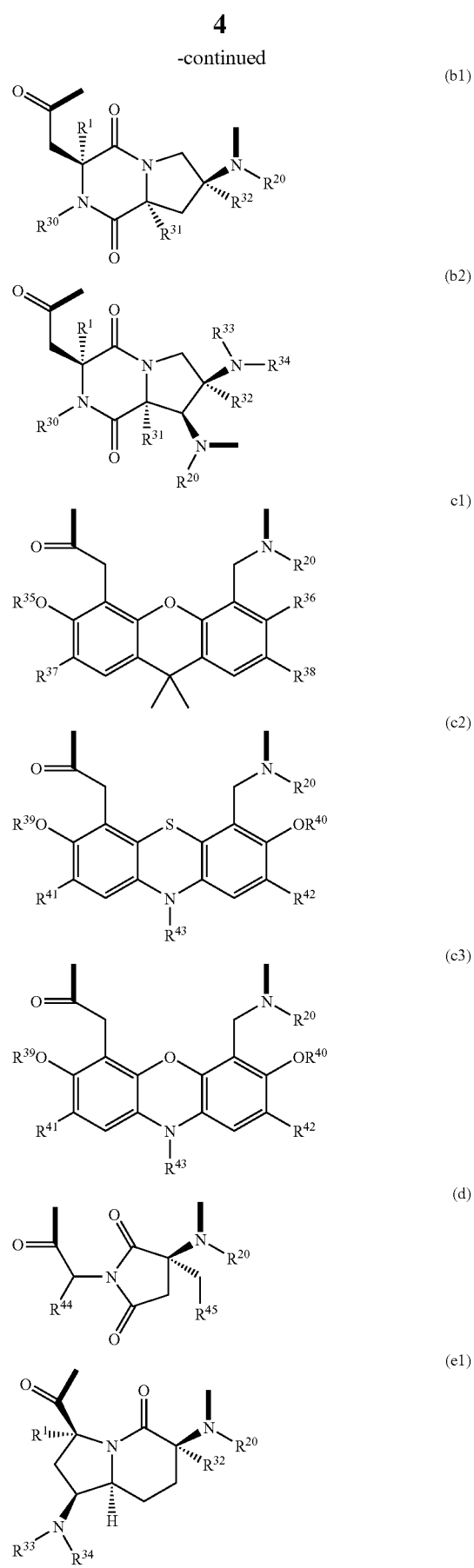

5
-continued
(e2)
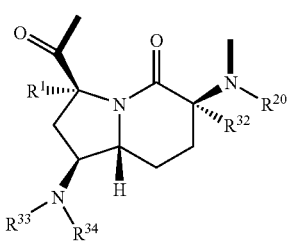
(e3)
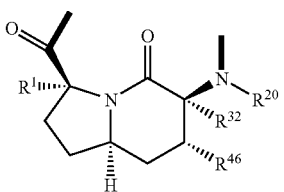
(e4)
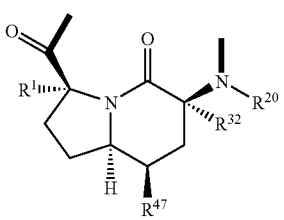
(f)
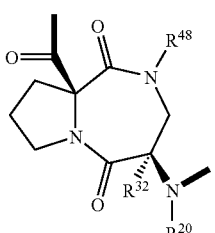
(g)
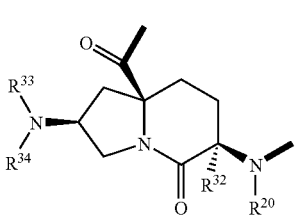
(h)
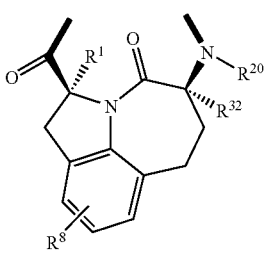
(i1)
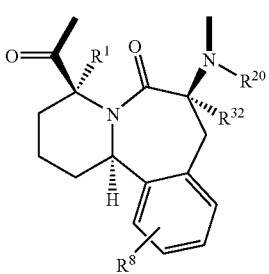
6
-continued
(i2)
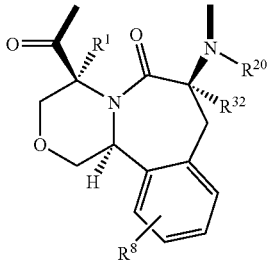
(i3)
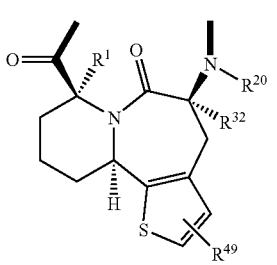
(i4)
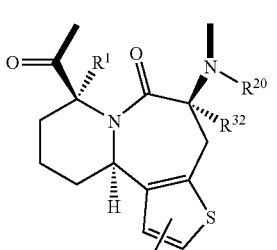
(j)
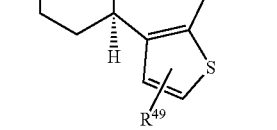
(k)
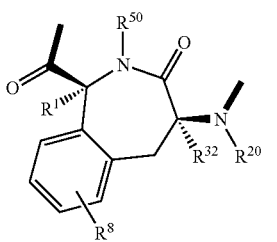
(l)
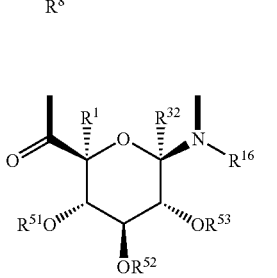

(m)
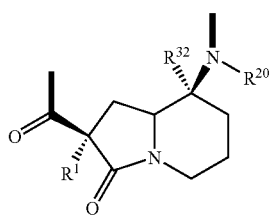
(n)
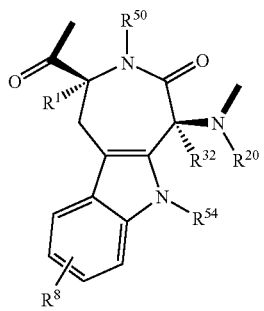
(o)
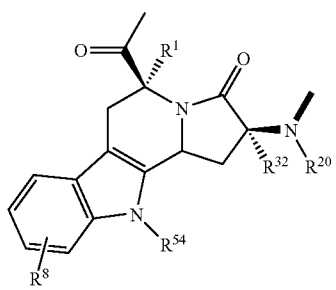
(p)
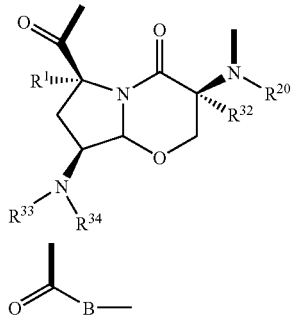
wherein
is Gly or the residue of an L-α-amino acid with B being a residue of formula —NR$^{20}$CH(R$^{71}$)— or the enantiomer of one of the groups A1 to A69 as defined hereinafter;
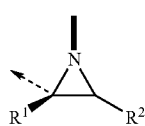
is a group of one of the formulae
A1
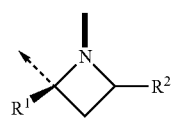
A2
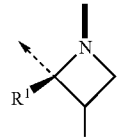
A3
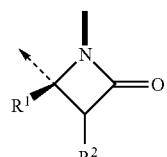
A4
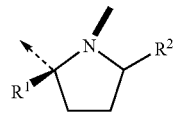
A5
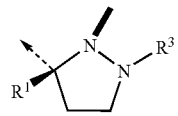
A6
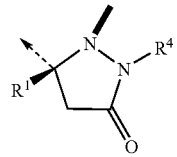
A7
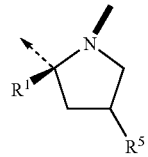
A8
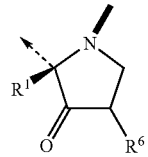
A9
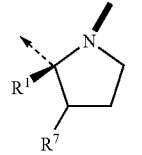
A10
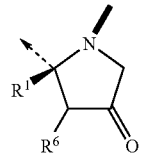
A11

-continued
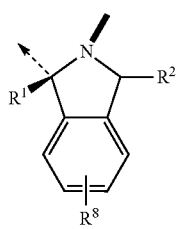
A12
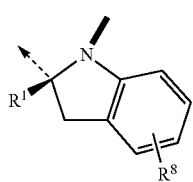
A13
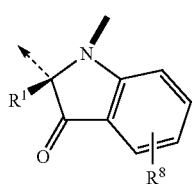
A14
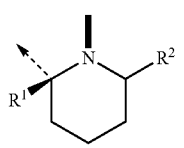
A15
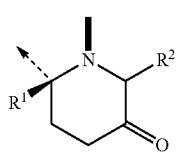
A16
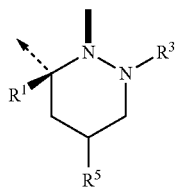
A17
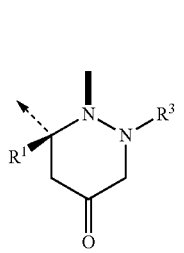
A18
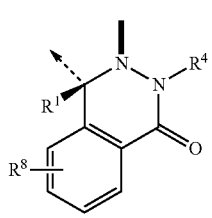
A19
-continued
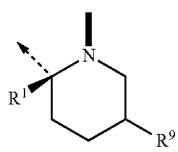
A20
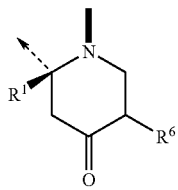
A21
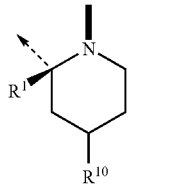
A22
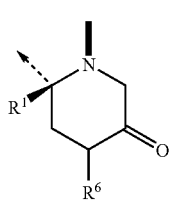
A23
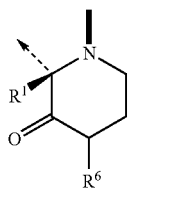
A24
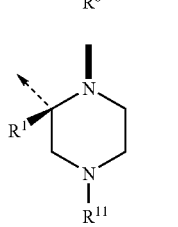
A25
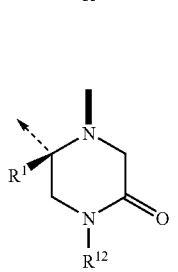
A26
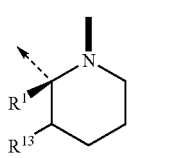
A27

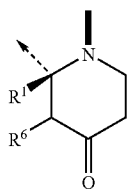 A28
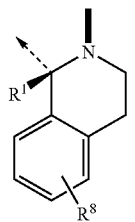 A29
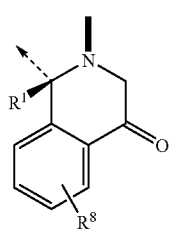 A30
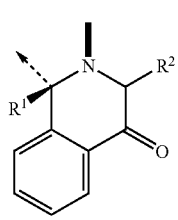 A31
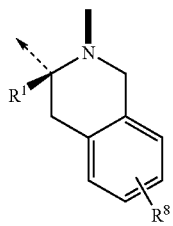 A32
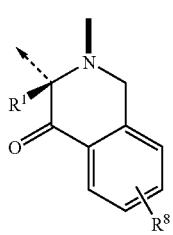 A33
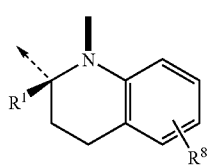 A34
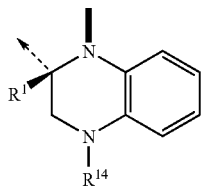 A35
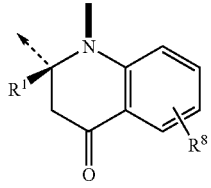 A36
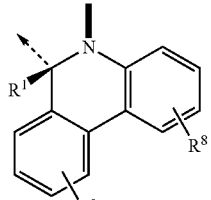 A37
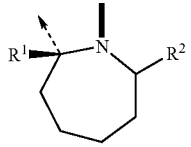 A38
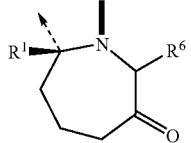 A39
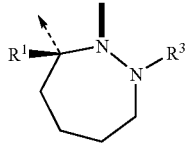 A40
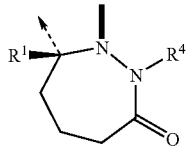 A41
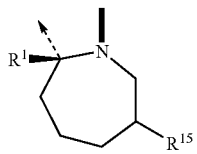 A42
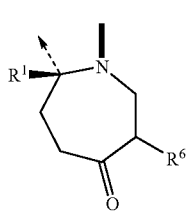 A43

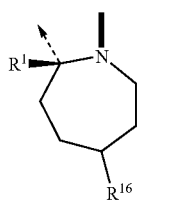 A44
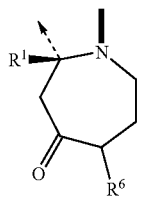 A45
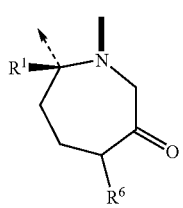 A46
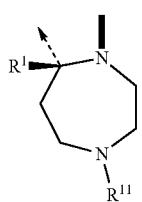 A47
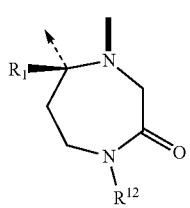 A48
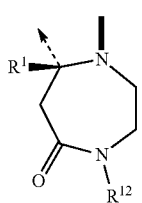 A49
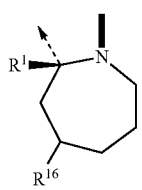 A50
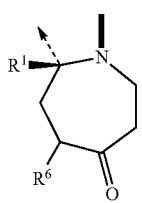 A51
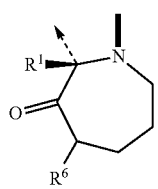 A52
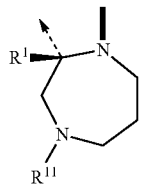 A53
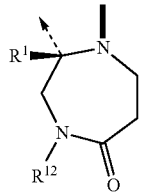 A54
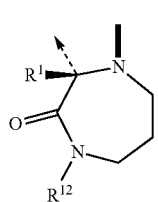 A55
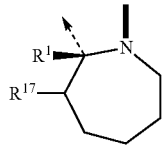 A56
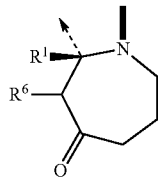 A57
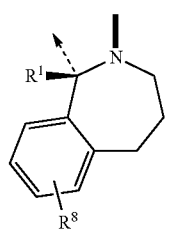 A58
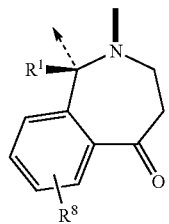 A59

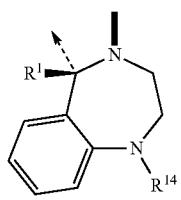 A60
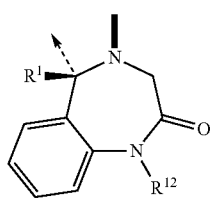 A61
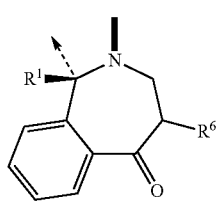 A62
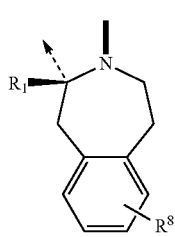 A63
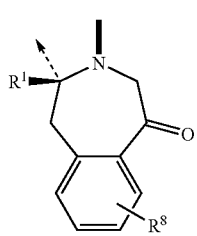 A64
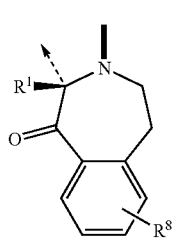 A65
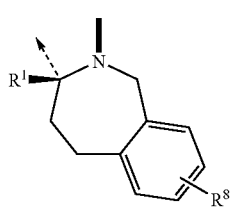 A66
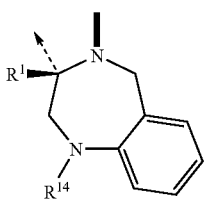 A67
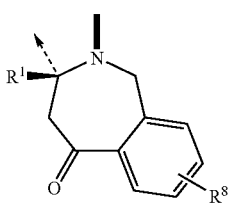 A68
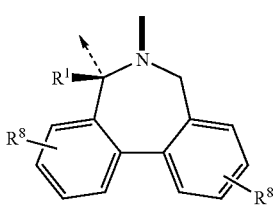 A69
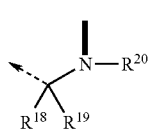 A70
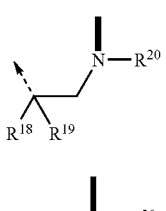 A71
A72
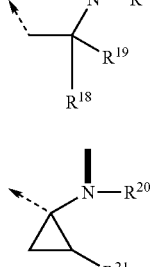 A73
A74
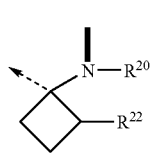 A75

17
-continued
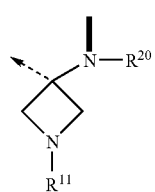
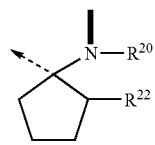
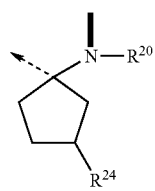
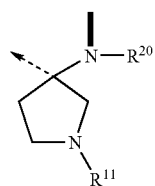
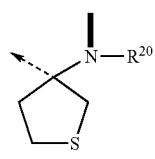
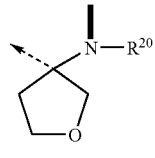
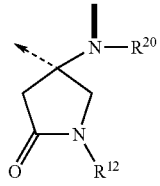
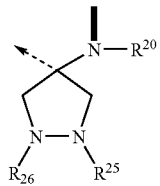
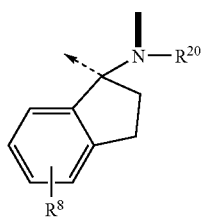
18
-continued
A76
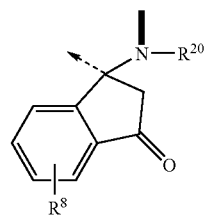
A77
A78
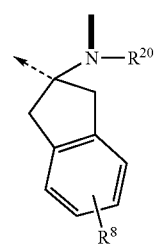
A79
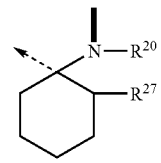
A80
A81
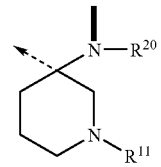
A82
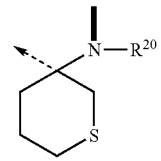
A83
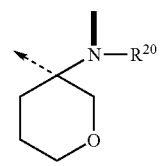
A84
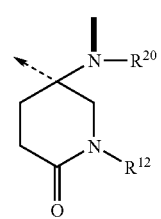
A85
A86
A87
A88
A89
A90
A91
A92

-continued

A93 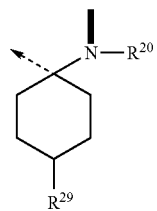

A94 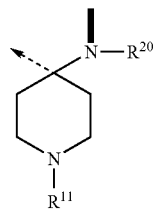

A95 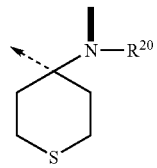

A96 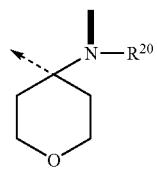

A97 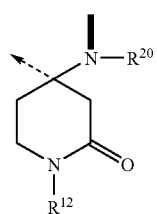

A98 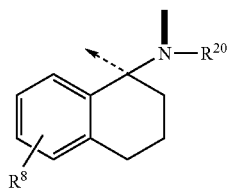

A99 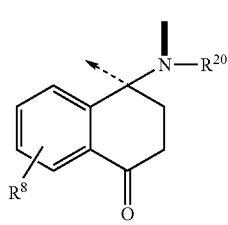

A100 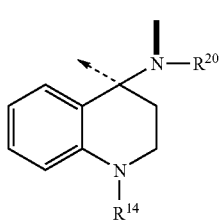

-continued

A101 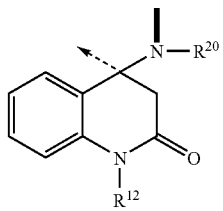

A102 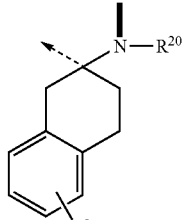

A103 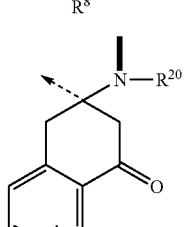

and

A104 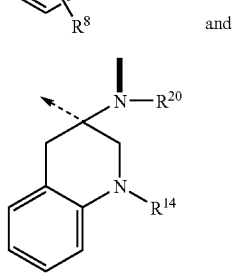

R$^1$ is H; lower alkyl; or aryl-lower alkyl;

R$^2$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^3$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^4$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)OCONR$^{33}$R$^{75}$; —(CH$_2$)$_m$(CHR$^{61}$)$_s$NR$^{20}$CONR$^{33}$R$^{82}$; —(CH$_2$)$_p$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^5$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$;

—$(CH_2)_o(CHR^{61})_sSO_2R^{62}$; or —$(CH_2)_o(CHR^{61})_s C_6H_4R^8$;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^7$ is alkyl; alkenyl; —$(CH_2)_q(CHR^{61})_sOR^{55}$; —$(CH_2)_q(CHR^{61})_sNR^{33}R^{34}$; —$(CH_2)_q(CHR^{61})_sOCONR^{33}R^{75}$;
—$(CH_2)_q(CHR^{61})_sNR^{20}CONR^{33}R^{82}$; —$(CH_2)_r(CHR^{61})_s COOR^{57}$; —$(CH_2)_r(CHR^{61})_sCONR^{58}R^{59}$; —$(CH_2)_r(CHR^{61})_sPO(OR^{60})_2$;
—$(CH_2)_r(CHR^{61})_sSO_2R^{62}$; or —$(CH_2)_r(CHR^{61})_s C_6H_4R^8$;

$R^8$ is H; Cl; F; $CF_3$; $NO_2$; lower alkyl; lower alkenyl; aryl; aryl-lower alkyl; —$(CH_2)_o(CHR^{61})_sOR^{55}$; —$(CH_2)_o(CHR^{61})_sSR^{56}$; —$(CH_2)_o(CHR^{61})NR^{33}R^{34}$; —$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o (CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_sCOR^{64}$;

$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})NR^{33}R^{34}$; —$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o (CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{10}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o (CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{11}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_s COOR^{57}$; —$(CH_2)_o(CHR^{61})_sCONR^{58}R^{59}$;
—$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{12}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_s NR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$;
—$(CH_2)_r(CHR^{61})_sSO_2R^{62}$; or —$(CH_2)_r(CHR^{61})_s C_6H_4R^8$;

$R^{13}$ is alkyl; alkenyl; —$(CH_2)_q(CHR^{61})_sOR^{55}$; —$(CH_2)_q(CHR^{61})_sSR^{56}$; —$(CH_2)_q(CHR^{61})_sNR^{33}R^{34}$; —$(CH_2)_q(CHR^{61})_sOCONR^{33}R^{75}$; —$(CH_2)_q(CHR^{61})_s NR^{20}CONR^{33}R^{82}$; —$(CH_2)_q(CHR^{61})_sCOOR^{57}$;
—$(CH_2)_q (CHR^{61})_sCONR^{58}R^{59}$; —$(CH_2)_q(CHR^{61})_sPO(OR^{60})_2$;
—$(CH_2)_q(CHR^{61})_sSO_2R^{62}$; or —$(CH_2)_q(CHR^{61})_s C_6H_4R^8$;

$R^{14}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$;
—$(CH_2)_m(CHR^{61})_sNR^{20}CONR^{33}R^{82}$; —$(CH_2)_q(CHR^{61})_s COOR^{57}$; —$(CH_2)_q(CHR^{61})_sCONR^{58}R^{59}$;
—$(CH_2)_q(CHR^{61})_sPO(OR^{60})_2$;
—$(CH_2)_q(CHR^{61})_sSOR^{62}$; or —$(CH_2)_q(CHR^{61})_sC_6H_4R^8$;

$R^{15}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{16}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{17}$ is alkyl; alkenyl; —$(CH_2)_q(CHR^{61})_sOR^{55}$; —$(CH_2)_q(CHR^{61})_sSR^{56}$; —$(CH_2)_q(CHR^{61})_sNR^{33}R^{34}$;
—$(CH_2)_q(CHR^{61})_sOCONR^{33}R^{75}$; —$(CH_2)_q(CHR^{61})_s NR^{20}CONR^{33}R^{82}$; —$(CH_2)_q(CHR^{61})_sCOOR^{57}$;
—$(CH_2)_q(CHR^{61})_sCONR^{58}R^{59}$; —$(CH_2)_q(CHR^{61})_sPO(OR^{60})_2$;
—$(CH_2)_q(CHR^{61})_sSO_2R^{62}$; or —$(CH_2)_q(CHR^{61})_s C_6H_4R^8$;

$R^{18}$ is alkyl; alkenyl; —$(CH_2)_p(CHR^{61})_sOR^{55}$; —$(CH_2)_p(CHR^{61})_sSR^{56}$; —$(CH_2)_p(CHR^{61})_sNR^{33}R^{34}$;
—$(CH_2)_p(CHR^{61})_sOCONR^{33}R^{75}$; —$(CH_2)_p(CHR^{61})_s NR^{20}CONR^{33}R^{82}$; —$(CH_2)_p(CHR^{61})_sCOOR^{57}$;
—$(CH_2)_p(CHR^{61})CONR^{58}R^{59}$; —$(CH_2)_p(CHR^{61})_sPO(OR^{60})_2$;
—$(CH_2)_p(CHR^{61})_sSO_2R^{62}$; or —$(CH_2)_o(CHR^{61})_s C_6H_4R^8$;

$R^{19}$ is lower alkyl; —$(CH_2)_p(CHR^{61})_sOR^{55}$; —$(CH_2)_p(CHR^{61})_sSR^{56}$; —$(CH_2)_p(CHR^{61})_sNR^{33}R^{34}$;
—$(CH_2)_p(CHR^{61})_sOCONR^{33}R^{75}$; —$(CH_2)_p(CHR^{61})_s NR^{20}CONR^{33}R^{82}$; —$(CH_2)_p(CHR^{61})_sCOOR^{57}$;
—$(CH_2)_p(CHR^{61})_sCONR^{58}R^{59}$; —$(CH_2)_p(CHR^{61})_sPO(OR^{60})_2$;
—$(CH_2)_p(CHR^{61})_sSO_2R^{62}$; or —$(CH_2)_o(CHR^{61})_s C_6H_4R^8$; or $R^{18}$ and $R^{19}$ taken together can form: —$(CH_2)_{2-6}$—; —$(CH_2)_2 O(CH_2)_2$—; —$(CH_2)_2S(CH_2)_2$—; or —$(CH_2)_2NR^{57}(CH_2)_2$—;

$R^{20}$ is H; alkyl; alkenyl; or aryl-lower alkyl;

$R^{21}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{22}$ is H; alkyl; alkenyl; —$(CH_2)_o(CHR^6)_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{23}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$; —$(CH_2)_o(CHR^{61})_s NR^{20}CONR^{33}R^{82}$; —$(CH_2)_o(CHR^{61})_sCOOR^{57}$;
—$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; or —$(CH_2)_o(CHR^{61})_s C_6H_4R^8$;

$R^{24}$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{25}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{26}$ is H; alkyl; alkenyl; $-(CH_2)_m(CHR^{61})_sOR^{55}$; $-(CH_2)_m(CHR^{61})_sSR^{56}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{61})_2$; $-(CH_2)_o(CHR^{61})_sSO_2R^{62}$; or $-(CH_2)_o(CHR^{61})_sC_6H_4R^8$; or $R^{25}$ and $R^{26}$ taken together can form: $-(CH_2)_{2-6}-$; $-(CH_2)_rO(CH_2)_r-$; $-(CH_2)_rS(CH_2)_r-$; or $-(CH_2)_rNR^{57}(CH_2)_r-$;

$R^{27}$ is H; alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sCOOR^{57}$; $-(CH_2)_o(CHR^{61})_sCONR^{58}R^{59}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{28}$ is alkyl; alkenyl; $-(CH_2)_o(CHR^{61})_s-OR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{29}$ is alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$; $-(CH_2)_o(CHR^{61})_sOCONR^{33}R^{75}$; $-(CH_2)_o(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{30}$ is H; alkyl; alkenyl; or aryl-lower alkyl;

$R^{31}$ is H; alkyl; alkenyl; $-(CH_2)_p(CHR^{61})_sOR^{55}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{32}$ is H; lower alkyl; or aryl-lower alkyl;

$R^{33}$ is H; alkyl, alkenyl; $-(CH_2)_m(CHR^{61})_sOR^{55}$; $-(CH_2)_m(CHR^{61})_sNR^{34}R^{63}$; $-(CH_2)_m(CHR^{61})_sOCONR^{75}R^{82}$; $-(CH_2)_m(CHR^{61})_sNR^{20}CONR^{78}R^{82}$; $-(CH_2)_o(CHR^{61})_sCOR^{64}$; $-(CH_2)_o(CHR^{61})_s-CONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{34}$ is H; lower alkyl; aryl, or aryl-lower alkyl;

$R^{33}$ and $R^{34}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{35}$ is H; alkyl; alkenyl; $-(CH_2)_m(CHR^{61})_sOR^{55}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_p(CHR^{61})_sCOOR^{57}$; $-(CH_2)_p(CHR^{61})_sCONR^{58}R^{59}$; $-(CH_2)_p(CHR^{61})_sPO(OR^{60})_2$; $-(CH_2)_p(CHR^{61})SO_2R^{62}$; or $-(CH_2)_o(CHR^{61})_sC_6H_4R^8$;

$R^{36}$ is H, alkyl; alkenyl; $-(CH_2)_o(CHR^{61})_sOR^{55}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_p(CHR^{61})_sCOOR^{57}$; $-(CH_2)_p(CHR^{61})_sCONR^{58}R^{59}$; $-(CH_2)_p(CHR^{61})_sPO(OR^{60})_2$; $-(CH_2)_p(CHR^{61})_sSO_2R^{62}$; or $-(CH_2)_o(CHR^{61})_sC_6H_4R^8$;

$R^{37}$ is H; F; Br; Cl; $NO_2$; $CF_3$; lower alkyl; $-(CH_2)_p(CHR^{61})_sOR^{55}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{38}$ is H; F; Br; Cl; $NO_2$; $CF_3$; alkyl; alkenyl; $-(CH_2)_p(CHR^{61})_sOR^{55}$; $-(CH_2)_p(CHR^6)_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; $-(CH_2)_p(CHR^{61})_sOR^{55}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{42}$ is H; F; Br; Cl; $NO_2$; $CF_3$; alkyl; alkenyl; $-(CH_2)_p(CHR^{61})_sOR^{55}$; $-(CH_2)_p(CHR^{61})_sNR^{33}R^{34}$; $-(CH_2)_p(CHR^{61})_sOCONR^{33}R^{75}$; $-(CH_2)_p(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{60})_2$; $-(CH_2)_o(CHR^{61})_sSO_2R^{62}$; or $-(CH_2)_o(CHR^{61})_sC_6H_4R^8$;

$R^{43}$ is H; alkyl; alkenyl; $-(CH_2)_m(CHR^{61})_sOR^{55}$; $-(CH_2)_m(CHR^{61})_sNR^{33}R^{34}$; $-(CH_2)_m(CHR^{61})_sOCONR^{33}R^{75}$; $-(CH_2)_m(CHR^{61})_sNR^{20}CONR^{33}R^{82}$; $-(CH_2)_o(CHR^{61})_sCOOR^{57}$; $-(CH_2)_o(CHR^{61})_sCONR^{58}R^{59}$; $-(CH_2)_o(CHR^{61})_sPO(OR^{61})_2$; $-(CH_2)_o(CHR^{61})_sSO_2R^{62}$; or $-(CH_2)_o(CHR^{61})_sC_6H_4R^8$;

$R^{44}$ is alkyl; alkenyl; $-(CH_2)_r(CHR^{61})_sOR^{55}$; $-(CH_2)_r(CHR^{61})_sSR^{56}$; $-(CH_2)_r(CHR^{61})_sNR^{33}R^{34}$; $-(CH_2)_r(CHR^{61})_sOCONR^{33}R^{75}$; $-(CH_2)_r(CHR^{61})_sNR^{20}CONR^{33}R^{82}$; $-(CH_2)_r(CHR^{61})_sCOOR^{57}$; $-(CH_2)_r(CHR^{61})_sCONR^{58}R^{59}$; $-(CH_2)_r(CHR^{61})_sPO(OR^6)_2$; $-(CH_2)_r(CHR^{61})_sSO_2R^{62}$; or $-(CH_2)_r(CHR^{61})_sC_6H_4R^8$;

$R^{45}$ is H; alkyl; alkenyl; $-(CH_2)_o(CHR^{61})_sOR^{55}$; $-(CH_2)_o(CHR^{61})_sSR^{56}$; $-(CH_2)_o(CHR^{61})_sNR^{33}R^{34}$;

—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_s$(CHR$^{61}$)$_s$PO(OR$^{60}$)$_2$; —(CH$_2$)$_s$(CHR$^{61}$)$_s$SO$_2$R$^{62}$; or —(CH$_2$)$_s$(CHR$^{61}$)$_s$C$_6$H$_4$R$^8$;

R$^{46}$ is H; alkyl; alkenyl; or —(CH$_2$)$_o$(CHR$^{61}$)$_s$C$_6$H$_4$R$^8$;

R$^{47}$ is H; alkyl; alkenyl; or —(CH$_2$)$_o$(CHR$^{61}$)$_s$OR$^{55}$;

R$^{48}$ is H; lower alkyl; lower alkenyl; or aryl-lower alkyl;

R$^{49}$ is H; alkyl; alkenyl; —(CHR$^{61}$)$_s$COOR$^{57}$; (CHR$^{61}$)$_s$CONR$^{58}$R$^{59}$; (CHR$^{61}$)$_s$PO(OR$^{60}$)$_2$; —(CHR$^{61}$)$_s$SOR$^{62}$; or —(CHR$^{61}$)$_s$C$_6$H$_4$R$^8$;

R$^{50}$ is H; lower alkyl; or aryl-lower alkyl;

R$^{51}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_m$(CHR$^{61}$)$_s$CONR$^{58}$R$^{59}$; —(CH$_2$)$_o$(CHR$^{61}$)$_p$PO(OR$^{60}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{52}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_p$PO(OR$^{61}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{53}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_p$PO(OR$^{61}$)$_2$; —(CH$_2$)$_p$(CHR$^{61}$)$_s$SO$_2$R$^{62}$; or —(CH$_2$)$_p$(CHR$^{61}$)$_s$C$_6$H$_4$R$^8$;

R$^{54}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{6}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; or —(CH$_2$)$_o$(CHR$^{61}$)$_s$C$_6$H$_4$R$^8$;

R$^{55}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; —(CH$_2$)$_o$(CHR$^{61}$)COOR$^{57}$; or —(CH$_2$)$_o$(CHR$^{61}$)$_s$CONR$^{58}$R$^{59}$;

R$^{56}$ is H; lower alkyl; lower alkenyl; aryl-lower alkyl; —(CH$_2$)$_m$(CHR$^{61}$)$_s$OR$^{57}$; —(CH$_2$)$_m$(CHR$^{61}$)$_s$NR$^{34}$R$^{63}$; —(CH$_2$)$_m$(CHR$^{61}$)$_s$OCONR$^{75}$R$^{82}$; —(CH$_2$)$_m$(CHR$^{61}$)$_s$NR$^{20}$CONR$^{78}$R$^{82}$; —(CH$_2$)$_o$(CHR$^{61}$)$_s$—COR$^{64}$; or —(CH$_2$)$_o$(CHR$^{61}$)$_s$CONR$^{58}$R$^{59}$;

R$^{57}$ is H; lower alkyl; lower alkenyl; aryl lower alkyl; or heteroaryl lower alkyl;

R$^{58}$ is H; lower alkyl; lower alkenyl; aryl; heteroaryl; aryl-lower alkyl; or heteroaryl-lower alkyl;

R$^{59}$ is H; lower alkyl; lower alkenyl; aryl; heteroaryl; aryl-lower alkyl; or heteroaryl-lower alkyl; or R$^{58}$ and R$^{59}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{60}$ is H; lower alkyl; lower alkenyl; aryl; or aryl-lower alkyl;

R$^{61}$ is alkyl; alkenyl; aryl; heteroaryl; aryl-lower alkyl; heteroaryl-lower alkyl; —(CH$_2$)$_m$OR$^{55}$; —(CH$_2$)$_m$NR$^{33}$R$^{34}$; —(CH$_2$)$_m$OCONR$^{75}$R$^{82}$; —(CH$_2$)$_m$NR$^{20}$CONR$^{78}$R$^{82}$; —(CH$_2$)$_o$COOR$^{37}$; —(CH$_2$)$_o$NR$^{58}$R$^{59}$; or —(CH$_2$)$_o$PO(COR$^{60}$)$_2$;

R$^{62}$ is lower alkyl; lower alkenyl; aryl, heteroaryl; or aryl-lower alkyl;

R$^{63}$ is H; lower alkyl; lower alkenyl; aryl, heteroaryl; aryl-lower alkyl; heteroaryl-lower alkyl; —COR$^{64}$; —COOR$^{57}$; —CONR$^{58}$R$^{59}$; —SO$_2$R$^{62}$; or —PO(OR$^{60}$)$_2$;

R$^{34}$ and R$^{63}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{64}$ is H; lower alkyl; lower alkenyl; aryl; heteroaryl; aryl-lower alkyl; heteroaryl-lower alkyl; —(CH$_2$)$_p$(CHR$^{61}$)$_s$OR$^{65}$; —(CH$_2$)$_p$(CHR$^{61}$)$_s$SR$^{66}$; or —(CH$_2$)$_p$(CHR$^{61}$)$_s$NR$^{34}$R$^{63}$; —(CH$_2$)$_p$(CHR$^{61}$)$_s$OCONR$^{75}$R$^{82}$; —(CH$_2$)$_p$(CHR$^{61}$)$_s$NR$^{20}$CONR$^{78}$R$^{82}$;

R$^{65}$ is H; lower alkyl; lower alkenyl; aryl, aryl-lower alkyl; heteroaryl-lower alkyl; —COR$^{57}$; —COOR$^{57}$; or —CONR$^{58}$R$^{59}$;

R$^{66}$ is H; lower alkyl; lower alkenyl; aryl; aryl-lower alkyl; heteroaryl-lower alkyl; or —CONR$^{58}$R$^{59}$;

m is 2-4; o is 0-4; p is 1-4; q is 0-2; r is 1 or 2; s is 0 or 1;

Z is a chain of 11 α-amino acid residues, the positions of said amino acid residues in said chain being counted starting from the N-terminal amino acid, whereby these amino acid residues are, depending on their position in the chains, Gly, Pro, Pro(4NHCOPhe) or of formula -A-CO—, or of formula —B—CO—, or of one of the types C: —NR$^{20}$CH(R$^{72}$)CO—;
D: —NR$^{20}$CH(R$^{73}$)CO—;
E: —NR$^{20}$CH(R$^{74}$)CO—;
F: —NR$^{20}$CH(R$^{84}$)CO—; and
H: —NR$^{20}$—CH(CO—)—(CH$_2$)$_{4-7}$—CH(CO—)—NR$^{20}$—; —NR$^{20}$—CH(CO—)—(CH$_2$)$_p$SS(CH$_2$)$_p$—CH(CO—)—NR$^{20}$—; —NR$^{20}$—CH(CO—)—(—(CH$_2$)$_p$NR$^{20}$CO(CH$_2$)$_p$—CH(CO—)—NR$^{20}$—; and —NR$^{20}$—CH(CO—)—(—(CH$_2$)$_p$NR$^{20}$CONR$^{20}$(CH$_2$)$_p$—CH(CO—)—NR$^{20}$—;

R$^{71}$ is lower alkyl; lower alkenyl; —(CH$_2$)$_p$(CHR$^{61}$)$_s$OR$^{75}$; —(CH$_2$)$_p$(CHR$^{61}$)$_s$SR$^{75}$; —(CH$_2$)$_p$(CHR$^{61}$)$_s$NR$^{33}$R$^{34}$; —(CH$_2$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$;
—(CH$_2$)$_o$(CHR$^{61}$)$_s$COOR$^{75}$; —(CH$_2$)$_p$CONR$^{58}$R$^{59}$; —(CH$_2$)$_p$PO(OR$^{62}$)$_2$; —(CH$_2$)$_p$SO$_2$R$^{62}$; or —(CH$_2$)$_o$—C$_6$R$^{67}$R$^{68}$R$^{69}$R$^{70}$R$^{76}$;

R$^{72}$ is H, lower alkyl; lower alkenyl; —(CH$_2$)$_p$(CHR$^{61}$)$_s$OR$^{85}$; or —(CH$_2$)$_p$(CHR$^{61}$)$_s$SR$^{85}$;

R$^{73}$ is —(CR$^{86}$R$^{87}$)$_o$R$^{77}$; —(CH$_2$)$_o$O(CH$_2$)$_o$R$^{77}$; —(CH$_2$)$_r$S(CH$_2$)$_o$R$^{77}$; or —(CH$_2$)$_r$NR$^{20}$(CH$_2$)$_o$R$^{77}$;

R$^{74}$ is —(CH$_2$)$_p$NR$^{78}$R$^{79}$; —(CH$_2$)$_p$NR$^{77}$R$^{80}$; —(CH$_2$)$_p$C(=NR$^{80}$)NR$^{78}$R$^{79}$; —(CH$_2$)$_p$C(=NOR$^{50}$)NR$^{78}$R$^{79}$; —(CH$_2$)$_p$C(=NNR$^{78}$R$^{79}$)NR$^{78}$R$^{79}$; —(CH$_2$)$_p$NR$^{80}$C(=NR$^{80}$)NR$^{78}$R$^{79}$; —(CH$_2$)$_p$N=C(NR$^{78}$R$^{80}$)NR$^{79}$R$^{80}$; —(CH$_2$)$_p$C$_6$H$_4$NR$^{78}$R$^{79}$; —(CH$_2$)$_p$C$_6$H$_4$NR$^{77}$R$^{80}$; —(CH$_2$)$_p$C$_6$H$_4$C(=NR$^{80}$)NR$^{78}$R$^{79}$; —(CH$_2$)$_p$C$_6$H$_4$C(=NOR$^{50}$)NR$^{78}$R$^{79}$; —(CH$_2$)$_p$C$_6$H$_4$C(=NNR$^{78}$R$^{79}$)NR$^{78}$R$^{79}$; —(CH$_2$)$_p$C$_6$H$_4$NR$^{80}$C(=NR$^{80}$)NR$^{78}$R$^{79}$; —(CH$_2$)$_p$C$_6$H$_4$N=C(NR$^{78}$R$^{80}$)NR$^{79}$R$^{80}$; —(CH$_2$)$_r$O(CH$_2$)$_m$NR$^{78}$R$^{79}$; —(CH$_2$)$_r$O(CH$_2$)$_m$NR$^{77}$R$^{80}$; —(CH$_2$)$_r$O(CH$_2$)$_p$C(=NR$^{80}$)NR$^{78}$R$^{79}$; —(CH$_2$)$_r$O(CH$_2$)$_p$C(=NOR$^{50}$)NR$^{78}$R$^{79}$; —(CH$_2$)$_r$O(CH$_2$)$_p$C(=NNR$^{78}$R$^{79}$)NR$^{78}$R$^{79}$; —(CH$_2$)$_r$O(CH$_2$)$_m$NR$^{80}$C(=NR$^{80}$)NR$^{78}$R$^{79}$; —(CH$_2$)$_r$O(CH$_2$)$_m$N=C(NR$^{78}$R$^{80}$)NR$^{79}$R$^{80}$; —(CH$_2$)$_r$O(CH$_2$)$_p$C$_6$H$_4$CNR$^{78}$R$^{79}$; —(CH$_2$)$_r$O(CH$_2$)$_p$C$_6$H$_4$C(=NR$^{80}$)NR$^{78}$R$^{79}$; —(CH$_2$)$_r$O(CH$_2$)$_p$C$_6$H$_4$C(=NOR$^{50}$)NR$^{78}$R$^{79}$; —(CH$_2$)$_r$O(CH$_2$)$_p$C$_6$H$_4$C(=NNR$^{78}$R$^{79}$)NR$^{78}$R$^{79}$; —(CH$_2$)$_r$O(CH$_2$)$_p$C$_6$H$_4$NR$^{80}$C(=NR$^{80}$)NR$^{78}$R$^{79}$; —(CH$_2$)$_r$S(CH$_2$)$_m$NR$^{78}$R$^{79}$; —(CH$_2$)$_r$S(CH$_2$)$_m$NR$^{77}$R$^{80}$; —(CH$_2$)$_r$S(CH$_2$)$_p$C(=NR$^{80}$)

NR$^{78}$R$^{79}$; —(CH$_2$)$_r$S(CH$_2$)$_p$C(=NOR$^{50}$)NR$^{78}$R$^{79}$; —(CH$_2$)$_r$S(CH$_2$)$_p$C(=NNR$^{78}$R$^{79}$)NR$^{78}$R$^{79}$; —(CH$_2$)$_r$S(CH$_2$)$_m$NR$^{80}$C(=NR$^{80}$)NR$^{78}$R$^{79}$; —(CH$_2$)$_r$S(CH$_2$)$_m$N=C(NR$^{78}$R$^{80}$)NR$^{79}$R$^{80}$; —(CH$_2$)$_r$S(CH$_2$)$_p$C$_6$H$_4$CNR$^{78}$R$^{79}$; —(CH$_2$)$_r$S(CH$_2$)$_p$C$_6$H$_4$C(=NR$^{80}$)NR$^{78}$R$^{79}$; —(CH$_2$)$_r$S(CH$_2$)$_p$C$_6$H$_4$C(=NOR$^{50}$)NR$^{78}$R$^{79}$; —(CH$_2$)$_r$S(CH$_2$)$_p$C$_6$H$_4$C(=NNR$^{78}$R$^{79}$)NR$^{78}$R$^{79}$; —(CH$_2$)$_r$S(CH$_2$)$_p$C$_6$H$_4$NR$^{80}$C(=NR$^{80}$)NR$^{78}$R$^{79}$; —(CH$_2$)$_p$NR$^{80}$COR$^{64}$; —(CH$_2$)$_p$NR$^{80}$COR$^{77}$;

—(CH$_2$)$_p$NR$^{80}$CONR$^{78}$R$^{79}$; —(CH$_2$)$_p$C$_6$H$_4$NR$^{80}$CONR$^{78}$R$^{79}$; or —(CH$_2$)$_p$NR$^{20}$CO—[(CH$_2$)$_u$—X]$_t$—CH$_3$ where X is —O—; —NR$^{20}$—, or —S—; u is 1-3, and t is 1-6;

R$^{75}$ is lower alkyl; lower alkenyl; or aryl-lower alkyl;

R$^{33}$ and R$^{75}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{75}$ and R$^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{76}$ is H; lower alkyl; lower alkenyl; aryl-lower alkyl; —(CH$_2$)$_o$R$^{72}$; —(CH$_2$)$_o$SR$^{72}$; —(CH$_2$)$_o$NR$^{33}$R$^{34}$; —(CH$_2$)$_o$OCONR$^{33}$R$^{75}$; —(CH$_2$)$_o$NR$^{20}$CONR$^{33}$R$^{82}$; —(CH$_2$)$_o$COOR$^{75}$; —(CH$_2$)$_o$CONR$^{58}$R$^{59}$; —(CH$_2$)$_o$PO(OR$^{60}$)$_2$; —(CH$_2$)$_p$SO$_2$R$^{62}$; or —(CH$_2$)$_o$COR$^{64}$;

R$^{77}$ is —C$_6$R$^{67}$R$^{68}$R$^{69}$R$^{70}$R$^{76}$; or a heteroaryl group of one of the formulae

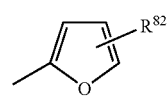
H1

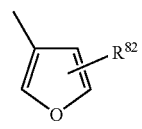
H2

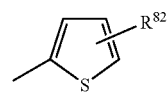
H3

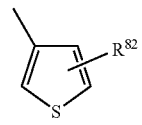
H4

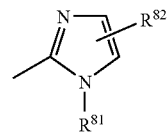
H5

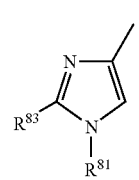
H6

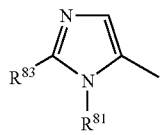
H7

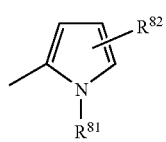
H8

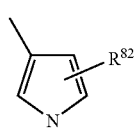
H9

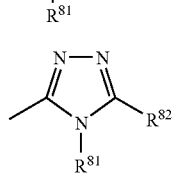
H10

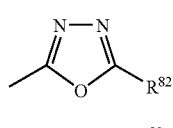
H11

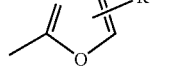
H12

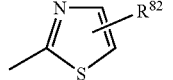
H13

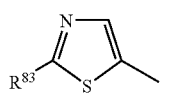
H14

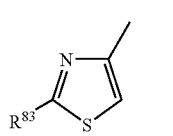
H15

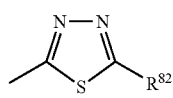
H16

H17

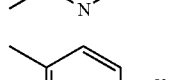
H18

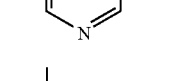
H19

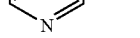

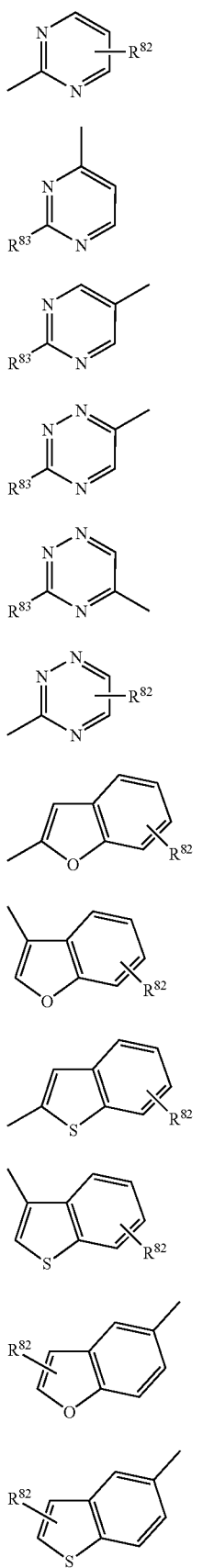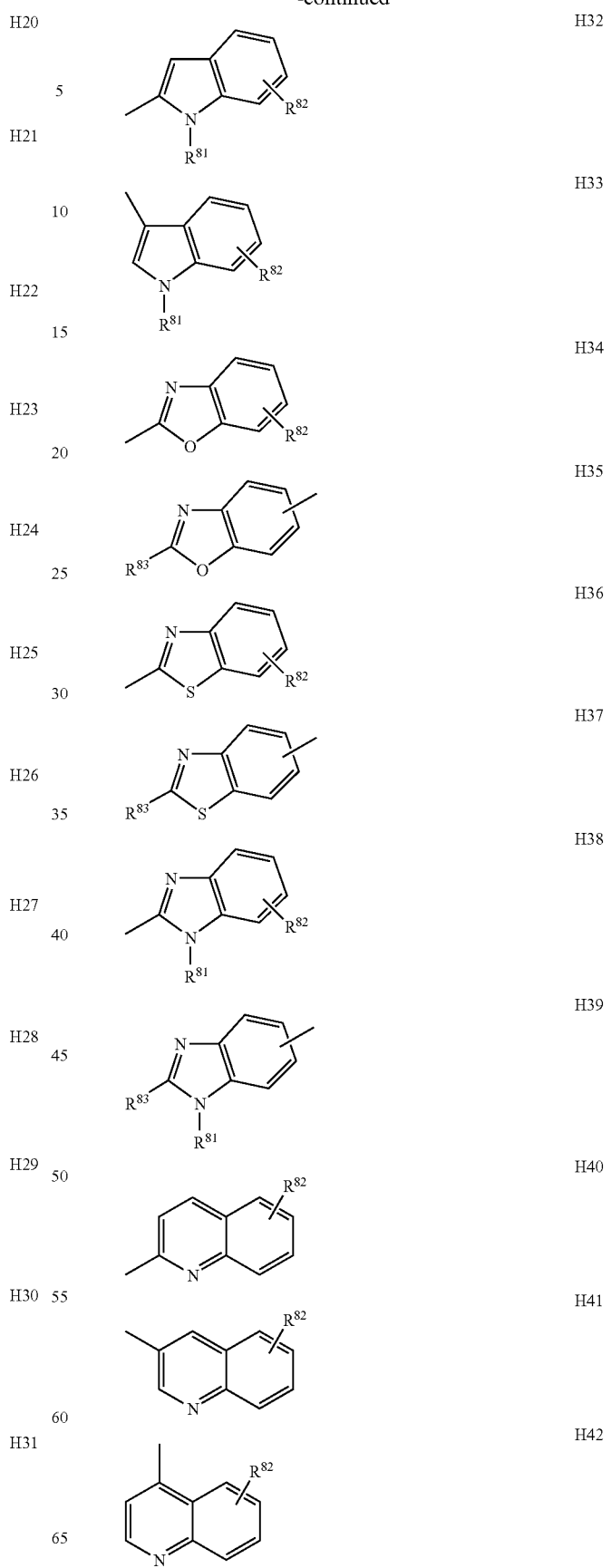

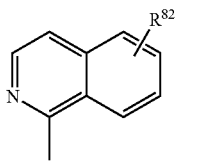

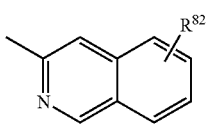

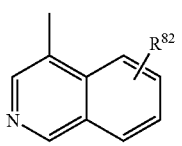

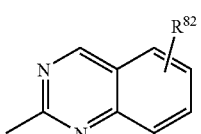

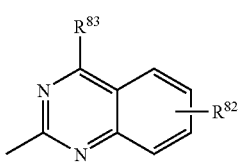

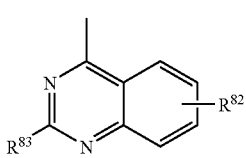

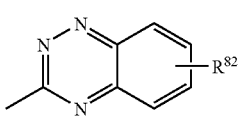

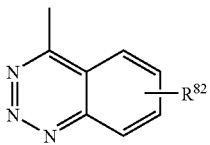

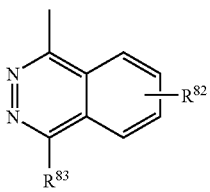

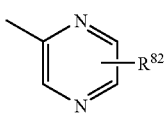

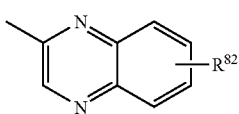

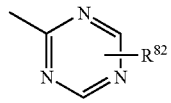

H43

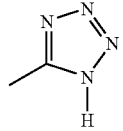

H44

$R^{78}$ is H; lower alkyl; aryl; or aryl-lower alkyl;
$R^{78}$ and $R^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
$R^{79}$ is H; lower alkyl; aryl; or aryl-lower alkyl; or
$R^{78}$ and $R^{79}$, taken together, can be —(CH$_2$)$_{2-7}$—; —(CH$_2$)$_2$O(CH$_2$)$_2$—; or —(CH$_2$)$_2$NR$^{57}$(CH$_2$)$_2$—;
$R^{80}$ is H; or lower alkyl;
$R^{81}$ is H; lower alkyl; or aryl-lower alkyl;
$R^{82}$ is H; lower alkyl; aryl, heteroaryl; or aryl-lower alkyl;
$R^{33}$ and $R^{82}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
$R^{83}$ is H; lower alkyl; aryl; or —NR$^{78}$R$^{79}$;
$R^{84}$ is —(CH$_2$)$_m$(CHR$^{61}$)$_s$OH; —(CR$^{86}$R$^{87}$)$_p$OR$^{80}$; —(CR$^{86}$R$^{87}$)$_p$COOR$^{80}$; —(CH$_2$)$_m$(CHR$^{61}$)$_s$SH; —(CR$^{86}$R$^{87}$)$_p$SR$^{80}$; —(CH$_2$)$_p$CONR$^{78}$R$^{79}$; —(CH$_2$)$_p$NR$^{80}$CONR$^{78}$R$^{79}$; —(CH$_2$)$_p$C$_6$H$_4$CONR$^{78}$R$^{79}$; —(CH$_2$)$_p$C$_6$H$_4$NR$^{80}$CONR$^{78}$R$^{79}$; —(CR$^{86}$R$^{87}$)$_o$PO(OR$^{60}$)$_2$; —(CR$^{86}$R$^{17}$)$_p$SO$_2$R$^{60}$; —(CR$^{86}$R$^{87}$)$_p$SOR$^{60}$; —(CH$_2$)$_m$(CHR$^{61}$)$_s$OPO(OR$^{60}$)$_2$; or —(CH$_2$)$_m$(CHR$^{61}$)$_s$OSO$_2$R$^{60}$;
$R^{85}$ is lower alkyl; or lower alkenyl;
$R^{86}$ is H; lower alkyl, where H is maybe substituted by halogen; or halogen;
$R^{87}$ is H; lower alkyl, where H is maybe substituted by halogen; or halogen;
with the proviso that in said chain of 11 α-amino acid residues Z if n is 11, the amino acid residues in positions 1 to 11 are:

| | |
|---|---|
| P1: | of type C or of type D or of type E or of type F; |
| P2: | of type C or of Type D or of type E, or of type F; |
| P3: | or of type C, of type F, or the residue is Gly; |
| P4: | of type C, or of type D, or of type F, or of type E, or the residue is Gly or Pro; |
| P5: | of type E, or of type C, or of type F, or the residue is Gly or Pro; |
| P6: | of type D, or of type F, or of type E or of type C, or the residue is Gly or Pro; |
| P7: | of type C, or of type E, or of type F, or of formula -A-CO—, or the residue is Gly or Pro; |
| P8: | of type D, or of type C, or of type F, or of formula -A-CO, or the residue is Gly or Pro or Pro(4NHCOPhe); |
| P9: | of type C, or of type D, or of type E, or of type F; |
| P10: | of type D, or of type C, or of type F, or of type E; and |
| P11: | of type C, or of type D, or of type E, or of type F; or P2 and P10, taken together, can form a group of type H; and | with the further proviso that if the template is $^D$Pro$^L$Pro, the amino acid residues in positions P1 to P11 are other than

| | |
|---|---|
| P1: | Arg |
| P2: | Cys, linked with Cys in position P10 by a disulfide bridge |
| P3: | Thr |

| | |
|---|---|
| P4: | Lys |
| P5: | Ser |
| P6: | Ile |
| P7: | Pro |
| P8: | Pro |
| P9: | Ile |
| P10: | Cys, linked with Cys in position P2 by a disulfide bridge; and |
| P11: | Phe | and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product is in position 5, 6 or 7, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating steps (c) and (d) until the N-terminal amino acid residue has been introduced;

(f) coupling the product thus obtained with a compound of the general formula

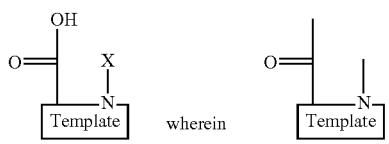

wherein is as defined above and X is an N-protecting group or, alternatively, if

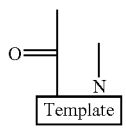

is to be group (a1) or (a2), above, (fa) coupling the product obtained in step (e) with an appropriately N-protected derivative of an amino acid of the general formula

HOOC—B—H    III or

HOOC-A-H    IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected; and, respectively, if

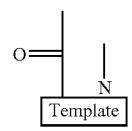

is to be group (a3), above, (fa') coupling the product obtained in step (e) with an appropriately N-protected derivative of an amino acid of the above general formula III, any functional group which may be present in said N-protected amino acid derivative being likewise appropriately protected;

(fb') removing the N-protecting group from the product thus obtained; and (fc') coupling the product thus obtained with an appropriately N-protected derivative of an amino acid of the above general formula III, any functional group which may be present in said N-protected amino acid derivative being likewise appropriately protected;

(g) removing the N-protecting group from the product obtained in step (f) or (fc) or (fc');

(h) coupling the product thus obtained with an appropriately N-protected derivative of that amino acid which in the desired end-product is in position 11, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position 11, any functional group which may be present in said N-protected amino acid derivative being likewise appropriately protected;

(k) removing the N-protecting group from the product thus obtained;

(l) repeating steps (j) and (k) until all amino acid residues have been introduced;

(m) if desired, selectively deprotecting one or several protected functional group(s) present in the molecule and appropriately substituting the reactive group(s) thus liberated;

(n) if desired, forming an interstrand linkage between sidechains of appropriate amino acid residues at positions 2 and 10;

(o) detaching the product thus obtained from the solid support;

(p) cyclizing the product cleaved from the solid support;

(q) removing any protecting groups present on functional groups of any members of the chain of amino acid residues and, if desired, any protecting group(s) which may in addition be present in the molecule; and (r) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Alternatively, the peptidomimetics of the present invention can be prepared by
(a') coupling an appropriately functionalized solid support with a compound of the general formula

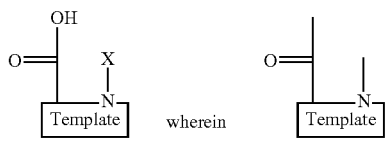 wherein is as defined above and X is an N-protecting group or, alternatively, if

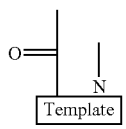

is to be group (a1) or (a2), above,
(a'a) coupling said appropriately functionalized solid support with an appropriately N-protected derivative of an amino acid of the general formula

HOOC—B—H        III or

HOOC-A-H        IV wherein B and A are as defined above, any functional group which may be present in said N-protected amino acid derivative being likewise appropriately protected;
(a'b) removing the N-protecting group from the product thus obtained; and
(a'c) coupling the product thus obtained with an appropriately N-protected derivative of an amino acid of the above general formula IV and, respectively, III, any functional group which may be present in said N-protected amino acid derivative being likewise appropriately protected; and, respectively, if

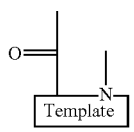

is to be group (a3), above,
(a'a') coupling said appropriately functionalized solid support with an appropriately N-protected derivative of an amino acid of the above general formula III, any functional group which may be present in said N-protected amino acid derivative being likewise appropriately protected;
(a'b') removing the N-protecting group from the product thus obtained; and
(a'c') coupling the product thus obtained with an appropriately N-protected derivative of an amino acid of the above general formula III, any functional group which may be present in said N-protected amino acid derivative being likewise appropriately protected;

(b') removing the N-protecting group from the product obtained in step (a'), (a'c) or (a'c');
(c') coupling the product thus obtained with an appropriately N-protected derivative of that amino acid which in the desired end-product is in position 11, any functional group which may be present in said N-protected amino acid derivative being likewise appropriately protected;
(d') removing the N-protecting group from the product thus obtained;
(e') coupling the product thus obtained with an appropriately N-protected derivative of that amino acid which in the desired end-product is one position farther away from position 11, any functional group which may be present in said N-protected amino acid derivative being likewise appropriately protected;
(f') removing the N-protecting group from the product thus obtained;
(g') repeating steps (e') and (f') until all amino acid residues have been introduced;
(h') if desired, selectively deprotecting one or several protected functional group(s) present in the molecule and appropriately substituting the reactive group(s) thus liberated;
(i') if desired forming an interstrand linkage between side-chains of appropriate amino acid residues at positions 2 and 10;
(j') detaching the product thus obtained from the solid support;
(k') cyclizing the product cleaved from the solid support;
(l') removing any protecting groups present on functional groups of any members of the chain of amino acid residues and, if desired, any protecting group(s) which may in addition be present in the molecule; and
(m') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

The peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). The structural element
—B—CO— forms in combination with another structural element —B—CO— template (a3). The template (a3) is less preferred in formula I. Templates (a) through (p) constitute building blocks which have an N-terminus and a C-terminus oriented in space in such a way that the distance between those two groups may lie between 4.0-5.5 Å. The peptide chain Z is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5 Å the template will induce the H-bond network necessary for the formation of a β-hairpin conformation in the peptide chain Z. Thus template and peptide chain form a β-hairpin mimetic.

The β-hairpin conformation is highly relevant for the serine protease inhibitory activity of the β-hairpin mimetics of the present invention. The β-hairpin stabilizing conformational properties of the templates (a) through (p) play a key role not only for the selective inhibitory activity but also for the synthesis process defined hereinabove, as incorporation of the templates at the beginning or near the middle of the linear protected peptide precursors enhances cyclization yields significantly.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are -$^D$A1-CO-$^L$B—CO— to $^D$A69-CO—$^L$B—CO—. Thus, for example, $^D$Pro-$^L$Pro constitutes the prototype of templates (a1). Less preferred, but possible are combinations
-$^L$A1-CO-$^D$B—CO— to -$^L$A69CO-$^D$B—CO— forming templates (a2). Thus, for example, $^L$Pro-$^D$Pro constitutes the prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_mOR^{55}$ (where $R^{55}$: lower alkyl; or lower alkenyl); $(CH_2)_mSR^{56}$ (where $R^{56}$: lower alkyl; or lower alkenyl); $(CH_2)_mNR^{33}R^{34}$ (where $R^{33}$: lower alkyl; or lower alkenyl; $R^{34}$: H; or lower alkyl; $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{53}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$:

lower alkyl; or lower alkenyl; and $R^{59}$: H; or lower alkyl; or $R^{58}$ and $R^{59}$ taken together form: $-(CH_2)_{2\text{-}6}-$; $-(CH_2)_2O(CH_2)_2-$;

$-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^5$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oCONR^{33}R^{75}$ (where $R^{33}$: H; or lower alkyl; or lower alkenyl; $R^{75}$: lower alkyl; or $R^{33}$ and $R^{75}$ taken together form:
$-(CH_2)_{2\text{-}6}-$; $-(CH_2)_2O(CH_2)_2-$; $-(CH_2)_2S(CH_2)_2-$; or
$-(CH_2)_2NR^{57}(CH_2)_2-$; $R^{57}$: where H; or lower alkyl); $(CH_2)_oNR^{20}CONR^{33}R^{82}$ (where $R^{20}$: H; or lower alkyl; $R^{33}$: H; or lower alkyl; or lower alkenyl; $R^{32}$: H; or lower alkyl; or $R^{33}$ and $R^{82}$ taken together form: $-(CH_2)_{2\text{-}6}-$; $-(CH_2)_2O(CH_2)_2-$;$-(CH_2)_2S(CH_2)_2-$; or $-(CH_2)_2NR^{57}(CH_2)_2-$; where $R^{57}$: H; or lower alkyl); $(CH_2)_oN(R^{20})COR^{64}$ (where: $R^{20}$: H; or lower alkyl; $R^{64}$: alkyl; alkenyl; aryl; and aryl-lower alkyl; heteroaryl-lower alkyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or
$-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2\text{-}6}-$; $-(CH_2)_2O (CH_2)_2-$;

$-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^7$: lower alkyl; lower alkenyl; $-(CH_2)_qOR^{55}$ (where $R^{55}$: lower alkyl; or lower alkenyl); $-(CH_2)_qSR^{56}$ (where $R^{56}$: lower alkyl; or lower alkenyl); $-(CH_2)_qNR^{33}R^{34}$ (where $R^{33}$: lower alkyl; or lower alkenyl; $R^{34}$: H; or lower alkyl; or $R^{33}$ and $R^{34}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$; $-(CH_2)_2S(CH_2)_2-$; or
$-(CH_2)_2NR^{57}(CH_2)_2-$; where $R^{57}$: H; or lower alkyl); $(CH_2)_qNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$;$-(CH_2)_2S(CH_2)_2-$; or $-(CH_2)_2NR^{57}(CH_2)_2-$; where $R^{57}$: H; or lower alkyl); $-(CH_2)_qN(R^{20})COR^{64}$ (where: $R^{20}$: H; or lower alkyl; $R^{64}$: lower alkyl; or lower alkenyl); $-(CH_2)_rCOOR^{57}$ (where $R^{57}$: lower alkyl; or lower alkenyl); $-(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2\text{-}6}-$; $-(CH_2)_2O(CH_2)_2-$;
$-(CH_2)_2S(CH_2)_2-$; or $-(CH_2)_2NR^{57}(CH_2)_2-$; where $R^{57}$: H; or lower alkyl); $-(CH_2)_rPO(OR^{60})_2$ (where $R^{60}$: lower alkyl; or lower alkenyl); $(CH_2)_rSO_2R^{62}$ (where $R^{62}$: lower alkyl; or lower alkenyl); or $-(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; $-(CH_2)_o OR^{55}$ (where $R^{55}$: lower alkyl; or lower alkenyl); $(CH_2)_o SR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2\text{-}6}-$; $-(CH_2)_2O(CH_2)_2-$;
$-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl);
$-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_oSO_2R^{62}$ (where $R^{62}$: lower alkyl; or lower alkenyl); or $-(CH_2)_oC_6H_4R^8$ (where $R^8$: H; F; Cl; $CF_3$; lower alkyl; lower alkenyl; or lower alkoxy).

$R^9$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form:
$-(CH_2)_{2\text{-}6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)SO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_oSO_2R^{62}$ (where $R^{62}$, lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOO^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{14}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); —$(CH_2)_qC_6H_4R^8$ (where $R^8$: H; F; Cl; $CF_3$; lower alkyl; lower alkenyl; or lower alkoxy).

$R^{15}$: lower alkyl; lower alkenyl; —$(CH_2)OR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{16}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{71}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;
$(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{17}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_q NR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$ (where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_rSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

Among the building blocks A1 to A69 the following are preferred: A5 with $R^2$ being H, A8, A22, A25, A38 with $R^2$ being H, A42, A47 and A50. Most preferred are building blocks of type A8':

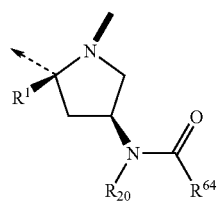

A8' wherein $R^{20}$ is H or lower alkyl; and $R^{64}$ is alkyl; alkenyl; $[(CH_2)_u-X]_t-CH_3$, wherein X is $-O-$, $-NR^{20}$ or $-S-$, u is 1-3 and t is 1-6; aryl; aryl-lower alkyl; or heteroaryl-lower alkyl; especially those wherein $R^{64}$ is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); n-nonyl (A8'-20); $CH_3-OCH_2CH_2-OCH_2-$ and $CH_3-(OCH_2CH_2)_2-OCH_2-$.

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers*, 1968, 6, 1425-1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for $R^{20}$ in A70 to A104 are H or lower alkyl with methyl being most preferred. Preferred values for $R^{18}$, $R^{19}$ and $R^{21}$ to $R^{29}$ in building blocks A70 to A104 are the following:

$R^{18}$: lower alkyl.

$R^{19}$: lower alkyl; lower alkenyl; $-(CH_2)_pOR^{55}$ (where $R^{55}$: lower alkyl; or lower alkenyl); $-(CH_2)_pSR^{56}$ (where $R^{56}$: lower alkyl; or lower alkenyl); $-(CH_2)_pNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_pN(R^{20})COR^{64}$ (where: $R^{20}$: H; or lower alkyl; $R^{64}$: lower alkyl; or lower alkenyl); $-(CH_2)_pCOOR^{57}$ (where $R^{57}$: lower alkyl; or lower alkenyl); $-(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $-(CH_2)_pSO_2R^{62}$ (where $R^{62}$: lower alkyl; or lower alkenyl); or $-(CH_2)_oC_6H_4R^8$ (where $R^8$: H; F; Cl; $CF_3$; lower alkyl; lower alkenyl; or lower alkoxy).

$R^{21}$: H; lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oN(R^{20})COR^{64}$ (where: $R^{20}$: H; or lower alkyl; $R^{64}$: lower alkyl; or lower alkenyl); $-(CH_2)_oCOOR^{57}$ (where $R^{57}$: lower alkyl; or lower alkenyl); $-(CH_2)_oCONR^{58}R^{59}$ (where $R^{58}$: lower alkyl, or lower alkenyl; and $R^{59}$: H; lower alkyl; or $R^{58}$ and $R^{59}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{22}$: lower alkyl; lower alkenyl; $-(CH_2)_oOR^{55}$ (where $R^{55}$: lower alkyl; or lower alkenyl); $-(CH_2)_oSR^{56}$ (where $R^{56}$: lower alkyl; or lower alkenyl); $-(CH_2)_oNR^{33}R^{34}$ (where $R^{33}$: lower alkyl; or lower alkenyl; $R^{34}$: H; or lower alkyl; or $R^{33}$ and $R^{34}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$; where $R^{57}$: H; or lower alkyl); $-(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: $-(CH_2)_{2-6}-$;

—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oOCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF; lower alkyl; lower alkenyl; or lower alkoxy).

$R^{23}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy);

$R^{24}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy);

$R^{25}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

$R^{26}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF$_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{29}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favored are $NR^{20}CO$lower-alkyl ($R^{20}$=H; or lower alkyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

The preferred value for $R^{23}$, $R^{24}$ and $R^{29}$ is —$NR^{20}$—CO-lower alkyl where $R^{20}$ is H or lower alkyl.

For templates (b) to (p), such as (b1) and (l), the preferred values for the various symbols are the following:

$R^1$: H; or lower Alkyl;

$R^8$: H; F; Cl; $CF_3$; lower alkyl; lower alkenyl; —$(CH_2)_o$ $OR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{20}$: H; or lower alkyl.

$R^{30}$: H, methyl.

$R^{31}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —(CH$_2$)$_{2-6}$—; —(CH$_2$)$_2$O(CH$_2$)$_2$—; —(CH$_2$)$_2$S(CH$_2$)$_2$ —; or —(CH$_2$)$_2$NR$^{57}$(CH$_2$)$_2$—; where R$^{57}$: H; or lower alkyl);

—(CH$_2$)$_p$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl); —(CH$_2$)OCOOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_r$C$_6$H$_4$R$^8$ (where R$^8$: H; F; Cl; CF$_3$; lower alkyl; lower alkenyl; or lower alkoxy); most preferred is —CH$_2$CONR$^{58}$R$^{59}$ (R$^{58}$: H; or lower alkyl; R$^{59}$: lower alkyl; or lower alkenyl).

R$^{32}$: H, methyl.

R$^{33}$: lower alkyl; lower alkenyl; —(CH$_2$)$_m$OR$^{55}$ (where R$^{55}$: lower alkyl; or lower alkenyl); —(CH$_2$)$_m$NR$^{34}$R$^{63}$ (where R$^{34}$: lower alkyl; or lower alkenyl; R$^{63}$: H; or lower alkyl; or R$^{34}$ and R$^{63}$ taken together form: —(CH$_2$)$_{2-6}$—;—(CH$_2$)$_2$O(CH$_2$)$_2$—;—(CH$_2$)$_2$S(CH$_2$)$_2$—; or
—(CH$_2$)$_2$NR$^{57}$(CH$_2$)$_2$—; where R$^{57}$: H; or lower alkyl); (CH$_2$)$_m$OCONR$^{75}$R$^{82}$ (where R$^{75}$: lower alkyl; or lower alkenyl; R$^{82}$: H; or lower alkyl; or R$^{75}$ and R$^{82}$ taken together form: —(CH$_2$)$_{2-6}$—; —(CH$_2$)$_2$O(CH$_2$)$_2$—; —(CH$_2$)$_2$S (CH$_2$)$_2$ —; or —(CH$_2$)$_2$NR$^{57}$(CH$_2$)$_2$—; where R$^{57}$: H; or lower alkyl);
—(CH$_2$)$_m$NR$^{20}$CONR$^{78}$R$^{82}$ (where R$^{20}$: H; or lower alkyl; R$^{78}$: H; or lower alkyl; or lower alkenyl; R$^{82}$: H; or lower alkyl; or R$^{78}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{34}$: H; or lower alkyl.

R$^{35}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;—(CH$_2$)$_2$O(CH$_2$)$_2$—;—(CH$_2$)$_2$S(CH$_2$)$_2$ —; or
—(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$ —; or —(CH$_2$)$_2$NR$^{57}$(CH$_2$)$_2$—; where R$^{57}$: H; or lower alkyl);
—(CH$_2$)$_m$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—; where R$^{57}$: H; or lower alkyl);
—(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)OCONR$^{58}$R$^{59}$ (where R$^{58}$: lower alkyl; or lower alkenyl; and R$^{59}$: H; lower alkyl; or R$^{58}$ and R$^{59}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{36}$: lower alkyl; lower alkenyl; or aryl-lower alkyl.

R$^{37}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;—(CH$_2$)$_2$O(CH$_2$)$_2$—;—(CH$_2$)$_2$S(CH$_2$)$_2$ —; or
—(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$ —; or —(CH$_2$)$_2$NR$^{57}$(CH$_2$)$_2$—; where R$^{57}$: H; or lower alkyl);
—(CH$_2$)$_p$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{38}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;—(CH$_2$)$_2$O(CH$_2$)$_2$—;—(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{78}$ taken together form: —(CH$_2$)$_{2-6}$—; —(CH$_2$)$_2$O(CH$_2$)$_2$—; —(CH$_2$)$_2$S (CH$_2$)$_2$ —; or —(CH$_2$)$_2$NR$^{57}$(CH$_2$)$_2$—; where R$^{57}$: H; or lower alkyl);
—(CH$_2$)$_p$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—; where R$^{57}$: H; or lower alkyl);
—(CH$_2$)$_p$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);
—(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{39}$: H; lower alkyl; lower alkenyl; —(CH$_2$)$_m$OR$^{55}$ (where R$^{55}$: lower alkyl; or lower alkenyl); —(CH$_2$)$_m$N(R$^{20}$) COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{40}$: lower alkyl; lower alkenyl; or aryl-lower alkyl.

$R^{41}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{42}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_oC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)OCONR^{58}R^{59}$ (where $R^{58}$:

lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sSR^{56}$ (where $R^{56}$: lower alkyl; or lower alkenyl); —$(CH_2)_sNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); or $(CH_2)_sC_6H_4R^8$ (where $R^8$: H; F; Cl; $CF_3$; lower alkyl; lower alkenyl; or lower alkoxy).

$R^{50}$: H; methyl.

$R^{51}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{52}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{53}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2$ $NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Most preferably $R^1$ is H; $R^{20}$ is H; $R^{30}$ is H; $R^{31}$ is carboxymethyl; or lower alkoxycarbonylmethyl; $R^{32}$ is H; $R^{35}$ is methyl; $R^{36}$ is methoxy; $R^{37}$ is H and $R^{38}$ is H.

Among the building blocks A70 to A104 the following are preferred: A74 with $R^{22}$ being H, A75, A76, A77 with $R^{22}$ being H, A78 and A79.

The building block —B—CO— within templates (a1), (a2) and (a3) designates an L-amino acid residue. Preferred values for B are: —$NR^{20}CH(R^{71})$— and enantiomers of groups A5 with $R^2$ being H, A8, A22, A25, A38 with $R^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Pro(5RPhe) | (2S,5R)-5-phenylpyrrrolidine-2-carbocyclic acid |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC($NH_2$)=NH) | L-meta-Amidinophenylalanine |
| Phe(pC($NH_2$)=NH) | L-para-Amidinophenylalanine |
| Phe(mNHC($NH_2$)=NH) | L-meta-Guanidinophenylalanine |
| Phe(pNHC($NH_2$)=NH) | L-para-Guanidinophenylalanine |
| Phg | L-Phenylglycine |
| Cha | L-Cyclohexylalanine |
| C4al | L-3-Cyclobutylalanine |
| C5al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4$Cl_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| $A_2$Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |

In addition, the most preferred values for B also include groups of type A8" of (L)-configuration:

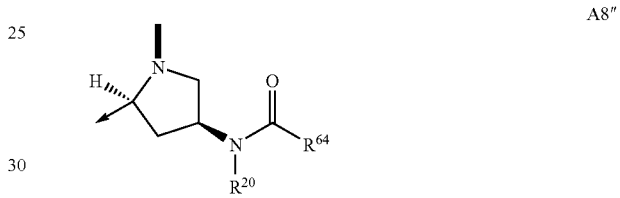

A8"

wherein $R^{20}$ is H or lower alkyl and $R^{64}$ is alkyl; alkenyl; —[$(CH_2)_u$—X]$_t$—$CH_3$ (where X is —O—; —$NR^{20}$—, or —S—, u is 1-3 and t is 1-6), aryl; aryl-lower alkyl; or heteroaryl-lower alkyl; especially those wherein $R^{64}$ is n-hexyl (A8"-21); n-heptyl (A8"-22); 4-(phenyl)benzyl (A8"-23); diphenylmethyl (A8"-24); 3-amino-propyl (A8"-25); 5-amino-pentyl (A8"-26); methyl (A8"-27); ethyl (A8"-28); isopropyl (A8"-29); isobutyl (A8"-30); n-propyl (A8"-31); cyclohexyl (A8"-32); cyclohexylmethyl (A8"-33); n-butyl (A8"-34); phenyl (A8"-35); benzyl (A8"-36); (3-indolyl)methyl (A8"-37); 2-(3-indolyl)ethyl (A8"-38); (4-phenyl) phenyl (A8"-39); n-nonyl (A8"-40); $CH_3$—$OCH_2CH_2$—$OCH_2$— (A8"-41) and $CH_3$—$(OCH_2CH_2)_2$—$OCH_2$— (A8"-42).

The peptidic chain Z of the β-hairpin mimetics described herein is generally defined in terms of amino acid residues belonging to one of the following groups:

| | |
|---|---|
| Group C | —$NR^{20}CH(R^{72})CO$—; "hydrophobic: small to medium-sized" |
| Group D | —$NR^{20}CH(R^{73})CO$—; "hydrophobic: large aromatic or heteroaromatic" |
| Group E | —$NR^{20}CH(R^{74})CO$—; "polar-cationic" and "urea-derived" |
| Group F | —$NR^{20}CH(R^{84})CO$—; "polar-non-charged or anionic" |
| Group H | —$NR^{20}$—CH(CO—)—$(CH_2)_{4-7}$—CH(CO—)—$NR^{20}$—; |
| | —$NR^{20}$—CH(CO—)—$(CH_2)_p SS(CH_2)_p$—CH(CO—)—$NR^{20}$—; |
| | —$NR^{20}$—CH(CO—)—(—$(CH_2)_p NR^{20}CO(CH_2)_p$—CH(CO—)—$NR^{20}$—; and |
| | —$NR^{20}$—CH(CO—)—(—$(CH_2)_p NR^{20}CONR^{20}(CH_2)_p$—CH(CO—)—$NR^{20}$—; "interstrand linkage" |

Furthermore, the amino acid residues in chain Z can also be of formula -A-CO— or of formula —B—CO— wherein A and B are as defined above. Finally, Gly can also be an amino acid residue in chain Z, and Pro and Pro(4-NHCOPhe) can be amino acid residues in chain Z, too, with the exception of positions where an interstrand linkage (H) is possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates, or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates and phosphates, or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates and phosphates, or tertiary amines. Genetically encoded heteroaromatic amino acids include tryptophan and histidine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates and phosphates, or tertiary amines. Genetically encoded heteroaromatic amino acids include tryptophan and histidine.

Group E comprises amino acids containing side chains with polar-cationic, acylamino- and urea-derived residues according to the general definition for substituent $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxylic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tertiary amides, carboxylic acids and carboxylates, alkyl- or aryl phosphonates and phosphates, or tertiary amines. Genetically encoded polar-non-charged amino acids include asparagine, cysteine, glutamine, serine and threonine, but also aspartic acid and glutamic acid.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, Ill., 1984; Ahmed et al. J. Biol. Chem. 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, positions for an interstrand linkage are positions P2 and 10, taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
| --- | --- | --- |
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |

| three letter code | | one letter code |
|---|---|---|
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| $^D$Pip | D-Pipecolic acid |
| OctG | L-Octylglycine |
| NGly | N-Methylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| DimK | L-(N',N'Dimethyl)-lysine |
| Lpzp | L-Piperazinic acid |
| Dpzp | D-Piperazinic acid |
| Isorn | L-(N',N'-diisobutyl)-ornithine |
| PipAla | L-2-(4'-piperidinyl)-alanine |
| PirrAla | L-2-(3'-pyrrolidinyl)-alanine |
| Ampc | 4-Amino-piperidine-4-carboxylic acid |
| NMeR | L-N-Methylarginine |
| NMeK | L-N-Methyllysine |
| NMePhe | L-N-Methylphenylalanine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)-ethoxy]-acetylamino}-butyric acid |
| SPegDab | L-2-Amino-4[2-(2-methoxy-ethoxy)-acetylamino] butyric acid |
| 4-PyrAla | L-2-(4'Pyridyl)-alanine |
| OrnPyr | L-2-Amino-5-[(2'carbonylpyrazine)-]amino-pentanoic acid |
| BnG | N-Benzylglycine |
| AlloT | Allo-Threonin |
| Pro(4NHCOPhe) | (2S)-4-benzamidino-pyrrolidine-2-carboxylic acid |
| Aoc | 2-(S)-Aminooctanoic acid |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C$_4$al | L-3-Cyclobutylalanine |
| C$_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| Aoc | 2-(S)-Aminooctanoic acid |

Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |

-continued

| | |
|---|---|
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |
| PirrAla | L-2-(3'-pyrrolidinyl)-alanine |
| NMePhe | L-N-Methylphenylalanine |
| 4-PyrAla | L-2-(4'Pyridyl)-alanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dbu | (S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| DimK | L-(N',N'Dimethyl)-lysine |
| Isorn | L-(N',N'-diisobutyl)-ornithine |
| NMeR | L-N-Methylarginine |
| NMeK | L-N-Methyllysine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)ethoxy]-acetylamino}-butyric acid |
| SPegDab | L-2-Amino-4[2-(2-methoxy-ethoxy)-acetylamino] butyric acid |
| OrnPyr | L-2-Amino-5-[(2'carbonylpyrazine)]amino-pentanoic |
| PipAla | L-2-(4'-piperidinyl)-alanine |

Particularly preferred residues for group F are

| | |
|---|---|
| Asn | L-Asparagine |
| Asp | L-Aspartic acid |
| Cys | L-Cysteine |
| Gln | L-Glutamine |
| Glu | L-Glutamic acid |
| Ser | L-Serine |
| Thr | L-Threonine |
| AlloThr | Allo Threonine |
| Cit | L-Citrulline |
| Pen | L-Penicillamine |
| AcLys | L-N$^\varepsilon$-Acetyllysine |
| hCys | L-Homo-cysteine |
| hSer | L-Homo-serine |

Generally, the peptidic chain Z within the β-hairpin mimetics of the invention comprises 11 amino acid residues. The positions P1 to P11 of each amino acid residue in the chain Z are unequivocally defined as follows: P1 represents the first amino acid in the chain Z that is coupled with its N-terminus to the C-terminus of the templates (b)-(p), or of group —B—CO— in template (a1), or of group -A-CO— in template (a2), or of the group —B—CO— forming the C-terminus of template (a3); and P11 represents the last amino acid in the chain Z that is coupled with its C-terminus to the N-terminus of the templates (b)-(p), or of group -A-CO— in template (a1), or of group —B—CO— in template (a2), or of the group —B—CO— forming the N-terminus of template (a3). Each of the positions P1 to P11 will preferably contain an amino acid residue belonging to one of the above types C, D, E, F, H, or of formula -A-CO— or of formula —B—CO—, or being Gly, Pro or Pro(4NHCOPhe) as follows:

In general the α-amino acid residues in positions 1 to 11 of the chain Z are preferably:

| | |
|---|---|
| P1: | of type C, or of type D, or of type E, or of type F; |
| P2: | of type E, or of type F, or of type C; |
| P3: | or of type C, of type F or the residue is Gly; |
| P4: | of type C, or of type E, or of type F, or the residue is Gly or Pro; |
| P5: | of type E, or of type F, or the residue is Gly or Pro; |
| P6: | of type C, or of type D, or of type F, or the residue is Gly or Pro; |
| P7: | of type F or of formula -A-CO— or the residue is Gly or Pro; |
| P8: | of type D, or of type C, or of formula -A-CO or the residue is Gly or Pro or Pro(4NHCOPhe); |
| P9: | of type C, or of type D, or of type E, or of type F; |
| P10: | of type F, or of type C, or type E; |
| P11: | of type E, or of type F, or of type C or of type D; or P2 and P10, taken together, form a group of type H; | with the proviso that if template is $^D$Pro-$^L$Pro the amino acid residues in positions P1 to P11 are other than

| | |
|---|---|
| P1: | Arg |
| P2: | Cys, linked with Cys in position P10 by a disulfide bridge |
| P3: | Thr |
| P4: | Lys |
| P5: | Ser |
| P6: | Ile |
| P7: | Pro |
| P8: | Pro |
| P9: | Ile |
| P10: | Cys, linked with Cys in position P2 by a disulfide bridge; and |
| P11: | Phe. |

The α-amino acid residues in positions 1 to 11 are most preferably:

| | |
|---|---|
| P1: | Nle, Ile, Aoc, hLeu, Chg, OctG, hPhe, 4AmPhe, Cha, Phe, Tyr, 2Cl-Phe, Trp, 1-Nal, Leu, Cha, or Arg; |
| P2: | Cys, Glu, Nle, Thr, or Gln; |
| P3: | Thr, Ala or Abu; |
| P4: | Lys, Nle, Ala, Abu, or Thr; |
| P5: | Ser, AlloThr, or Dpr; |
| P6: | Ile, C$_5$al, Leu, Nle, Aoc, OctG, Cha, hLeu, hPhe, Chg, t-BuA, Glu, or Asp; |
| P7: | Pro; |
| P8: | Pro, Ala, or Pro(4NHCOPhe); |
| P9: | Tyr, Phe, Ile, Nle, Cha, Gln, Arg, Lys, His, Thr, or Ala; |
| P10: | Cys, Arg, Nle, Gln, Lys, Met, Thr, or Ser; |
| P11: | Tyr, Gln, Arg, Ser, Nle, 2-Nal, 2Cl-Phe, Cha, Phg, Tyr, Phe, Asp, Asn, or Thr; and |
| | Cys, if present at P2 and P10, may form a disulfide bridge. |

For inhibitors of Cathepsin G the α-amino acid residues in positions 1 to 11 of the chain Z are preferably:

| | |
|---|---|
| P1: | of type C, or of type D, or of type E; |
| P2: | of type F, or of type C; |
| P3: | of type F; |
| P4: | of type C, or of type E; |
| P5: | of type E, or of type F; |
| P6: | of type F; |
| P7: | of type F, or of formula -A-CO—, or the residue is Gly or Pro; |
| P8: | of type C, or of formula -A-CO—, or the residue is Gly or Pro or Pro(4NHCOPhe); |
| P9: | of type C, or of type D, or of type F; |
| P10: | of type F, or of type C, or type E; |
| P11: | of type E, or of type D, or of type F; or P2 and P10, taken together, form a group of type H. |

For inhibitors of Cathepsin G, the α-amino acid residues in positions 1 to 11 are most preferably

| | |
|---|---|
| P1: | Phe, hPhe, 4AmPhe, Nle, Chg, Ile, Tyr, Arg, Trp, 2Cl-Phe, Arg, 1-Nal, or Cha; |
| P2: | Cys, Glu, or Nle; |
| P3: | Thr; |
| P4: | Lys, or Nle; |
| P5: | Ser, AlloThr, or Dpr; |
| P6: | Asp, or Glu; |
| P7: | Pro; |
| P8: | Pro; |
| P9: | Ile, Nle, Cha, Gln, Tyr, or Ala; |
| P10: | Cys, Arg, or Nle; |
| P11: | Thr, Asp, Ser, Tyr, Phe, Asn, or Arg; and Cys, if present at P2 and P10, may form a disulfide bridge. |

For inhibitors of Elastase the α-amino acid residues in positions 1 to 11 of the chain Z are preferably

| | |
|---|---|
| P1: | of type C, or of type D; |
| P2: | of type F; |
| P3: | of type F or of type C; |
| P4: | of type C or of type F; |
| P5: | of type F; |
| P6: | of type C; |
| P7: | of formula -A-CO— or the residue is Gly or Pro; |
| P8: | of formula -A-CO or the residue is Gly or Pro or Pro(4NHCOPhe); |
| P9: | of type D, or of type F or of type C; |
| P10: | of type F, or of type C, or type E; |
| P11: | of type E, or of type F, or of type D; or P2 and P10, taken together, form a group of type H. |

For inhibitors of Elastase, the α-amino acid residues in positions 1 to 11 are most preferably:

| | |
|---|---|
| P1: | Ile, Nle, Aoc, hLeu, Chg, OctG, or hPhe; |
| P2: | Cys, Glu, Thr, or Gln; |
| P3: | Thr, Ala, or Abu; |
| P4: | Ala, Thr, or Abu; |
| P5: | Ser; |
| P6: | OctG, Ile, Cha, Leu, $C_5$al, Nle, Aoc, Chg, tBuA, or hLeu; |
| P7: | Pro; |
| P8: | Pro, or Pro(4NHCOPhe); |
| P9: | Gln, Tyr, ILe, or Phe; |
| P10: | Cys, Lys, Gln, Thr, Met, or Arg; |
| P11: | Tyr, Ser, Arg, Gln, Nle, 2-Nal, 2Cl-Phe, Phe, Cha, or Phg; and Cys, if present at P2 and P10, may form a disulfide bridge. |

For inhibitors of Tryptase the α-amino acid residues in positions 1 to 11 of the chain Z are preferably:

| | |
|---|---|
| P1: | of type C, or of type D, or of type E; |
| P2: | of type F; |
| P3: | of type F; |
| P4: | of type E; |
| P5: | of type F; |
| P6: | of type C, or of type D; |
| P7: | of type F, or of formula - A - CO—, or the residue is Gly or Pro; |
| P8: | of type C, or of formula - A - CO—, or the residue is Gly or Pro; |
| P9: | of type C, or of type E, or of type F; |
| P10: | of type F; |
| P11: | of type E, or of type D; or P2 and P10, taken together, form a group of type H; | with the proviso that if the template is $^D$Pro-$^L$Pro, the amino acid residues in positions P1 to P11 are other than

| | |
|---|---|
| P1: | Arg |
| P2: | Cys, linked with Cys in position P10 by a disulfide bridge |
| P3: | Thr |
| P4 | Lys |
| P5 | Ser |
| P6 | Ile |
| P7 | Pro |
| P8 | Pro |
| P9 | Ile |
| P10 | Cys, linked with Cys in position P10 by a disulfide bridge; and |
| P11 | Phe. |

For inhibitors of Tryptase the α-amino acid residues in positions 1 to 11 of the chain Z are most preferably:

| | |
|---|---|
| P1: | Cha, Tyr, or Trp |
| P2: | Cys |
| P3: | Thr |
| P4: | Lys |
| P5: | Ser |
| P6: | Leu |
| P7: | Pro |
| P8: | Pro |
| P9: | Lys |
| P10: | Cys |
| P11: | Arg; and | the Cys residues present at P2 and P10 may form a disulfide bridge.

Particularly preferred β-peptidomimetics of the invention include those described in Examples 5, 19, 20, 22, 23, 38, 39, 40, and 75 as inhibitors of cathepsin G; Examples 91, 121, 153, 154, 155, 156, 157, 158, 159, 160, 161 177, and 178 as inhibitors of elastase; and Examples 193, 194, and 195 as inhibitors of Tryptase.

The processes of the invention can advantageously be carried out as parallel array syntheses to yield libraries of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl) Fmoc-aminomethyl)phenoxyacetamido) aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e.g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e.g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e.g. in the side-chain of threonine and serine)

| | |
|---|---|
| tBu | tert.-butyl |
| Bn | benzyl |
| Trt | trityl | and for the mercapto group (as is present e.g. in the side-chain of cysteine)

| Acm | acetamidomethyl |
|-----|-----------------|
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/ 2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodi-imides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea are insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-) 1,1,3,3-tetramethyluronium tetrafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N', N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive calorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;

2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. For the formation of pegylated amino acids such as IPegK, or SPegK, preferably a solution of 5 equivalents of HATU (N-[(dimethylamino)-1H-1,2,3-triazolo[4,5-b]pyridin-1-ylmethylene]-N-methylmethanaminium hexafluorophosphate N-oxide) in dry DMF and a solution of 10 equivalents of DIPEA (Diisopropyl ethylamine) in dry DMF and 5 equivalents of 2-[2-(2-methoxyethoxy)ethoxy]acetic acid (lPeg) and, respectively, 2-(2-methoxyethoxy)acetic acid (sPeg), is applied to the liberated amino group of the appropriate amino acid side chain for 3 h. The procedure is thereafter repeated for another 3 h with a fresh solution of reagents after filtering and washing the resin.

Before this fully protected linear peptide is detached from the solid support, it is also possible, if desired, to form an interstrand linkages between side-chains of appropriate amino acid residues at positions 2 and 10.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of disulfide bridges preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% with $NaHCO_3$ to pH 5-6 for 4 h, or in water adjusted to pH 8 with ammonium hydroxide solution by stirring for 24 h, or in ammonium acetate buffer adjusted to pH 8 in the presence of air, or in a solution of NMP and tri-n-butylphosphine (preferably 50 eq.).

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula I is obtained as end-product.

Alternatively the detachment, cyclization and complete deprotection of the fully protected peptide from the solid support can be achieved manually in glass vessels.

Depending on its purity, this peptide derivative can be used directly for biological assays, or it has to be further purified, for example by preparative HPLC.

As mentioned earlier, it is thereafter possible, if desired, to convert a fully deprotected product of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The template starting materials of formula II used in the processes of the invention, pre-starting materials therefor, and the preparation of these starting and pre-starting materials are described in International Application PCT/EP02/01711 of the same applicants, published as WO 02/070547 A1.

The β-hairpin peptidomimetics of the invention can be used in a wide range of applications where inflammatory diseases or pulmonary diseases or infections or immunological diseases or cardiovascular diseases or neurodegenerative diseases are mediated or resulting from serine protease activity, or where cancer is mediated or resulting from serine protease activity. For the control or prevention of a given illness or disease amenable to treatment with protease inhibitors, the β-hairpin peptidomimetics may be administered per se or may be applied as an appropriate formulation together with carriers, diluents or excipients well known in the art.

When used to treat or prevent diseases such as pulmonary emphysema, rheumatoid arthritis, osteoarthritis, atherosclerosis, psoriasis, cystic fibrosis, multiple sclerosis, adult respiratory distress syndrome, pancreatitis, asthma, allergic rhinitis, inflammatory dermatoses, post angioplasty restenosis, cardiac hypertrophy, heart failure or cancer such as, but not limited to, breast cancer, or cancer related to angiogenesis or metastasis, the β-hairpin peptidomimetics can be administered singly, as mixtures of several β-hairpin peptidomimetics, in combination with other anti-inflammatory agents, or antimicrobial agents or anti-cancer agents and/or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the β-hairpin peptidomimetics of the invention can be readily formulated by combining them with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc., formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The β-hairpin peptidomimetics of the invention, or compositions thereof, will generally be used in an amount effective to achieve the intended purpose. It is to be understood that the amount used will depend on a particular application.

For topical administration to treat or prevent diseases amenable to treatment with beta hairpin mimetics a therapeutically effective dose can be determined using, for example, the in vitro assays provided in the examples. The treatment may be applied while the disease is visible, or even when it is not visible. An ordinary skilled expert will be able to determine therapeutically effective amounts to treat topical diseases without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture. Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as serine protease inhibitory agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgment of the prescribing physician.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethyluronium hexafluorophosphate (Knorr et al. *Tetrahedron Lett.* 1989, 30, 1927-1930);

HOBt: 1-hydroxybenzotriazole;

DIEA: diisopropylethylamine;

HOAT: 7-aza-1-hydroxybenzotriazole;

HATU: O-(7-aza-benzotriazole-1-yl)-N,N,N',N'-tetramethyluronium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2Cl_2$ (2.5 ml) and allowed to swell at room temperature under constant stirring for 30 min. The resin was treated with 0.415 mMol (1 eq) of the first suitably protected amino acid residue (see below) and 284 μl (4 eq) of diisopropylethylamine (DIEA) in $CH_2Cl_2$ (2.5 ml), the mixture was shaken at 25° C. for 4 hours. The resin colour changed to purple and the solution remained yellowish. The resin was shaken ($CH_2Cl_2$/MeOH/DIEA: 17/2/1), 30 ml for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.7 mMol/g.

The following preloaded resins were prepared: Fmoc-Pro-2-chlorotritylresin, Fmoc-Asp (OtBu)-2-chlorotritylresin, Fmoc-Pro(5RPhe)-2-chlorotritylresin, Fmoc-Leu-2-chlorotritylresin, Fmoc-Glu(OtBu)-2-chlorotritylresin, Fmoc-Asp (OtBu)-2-chlorotritylresin, Fmoc-Phe-2-chlorotritylresin, Fmoc-Gln(Trt)-2-chlorotritylresin, Fmoc-Ser (OtBu)-2-chlorotritylresin, Fmoc-Val-2-chlorotritylresin, Fmoc-Thr (OtBu)-2-chlorotritylresin and Fmoc-Ile-2-chlorotritylresin.

Synthesis of the Fully Protected Peptide Fragment

The synthesis was carried out using a Syro-peptide synthesizer (Multisyntech) using 24 to 96 reaction vessels. In each vessel were placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |

-continued

| Step | Reagent | Time |
|---|---|---|
| 5 | 5 equiv. Fmoc amino acid/DMF +5 eq. HBTU +5 eq. HOBt +5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid.

After the synthesis of the fully protected peptide fragment had been terminated, then subsequently either Procedure A or Procedure B, as described hereinbelow, was adopted, depending on whether not interstrand linkages (i.e. disulfide β-strand linkages) were to be formed.

Procedure A: Cyclization and Work Up of Backbone Cyclized Peptides

Cleavage of the Fully Protected Peptide Fragment

After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. An aliquot (200 μL) of the filtrate was fully deprotected with 0.5 ml of the cleavage mixture containing 95% trifluoroacetic acid (TFA), 2.5% water and 2.5% triisopropylsilane (TIS) and analysed by reverse phase-LC MS to monitor the efficiency of the linear peptide synthesis.

Cyclization of the Linear Peptide

The fully protected linear peptide was dissolved in DMF (8 ml, conc. 10 mg/ml). Two eq. of HATU (0.72 mMol) in 1 ml of DMF and 4 eq. of DIEA (1.44 mMol) in 1 ml of DMF were added, and the mixture was stirred at room temperature for 16 h. The volatile was evaporated to dryness. The crude cyclized peptide was dissolved in 7 ml of $CH_2Cl_2$ and extracted with 10% acetonitrile in water (4.5 ml) three times. The $CH_2Cl_2$ layer was evaporated to dryness.

Deprotection and Purification of the Cyclic Peptide

The cyclic peptide obtained was dissolved in 3 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The crude peptide was dissolved in 20% AcOH in water (7 ml) and extracted with diisopropylether (4 ml) three times. The aqueous layer was collected and evaporated to dryness, and the residue was purified by preparative reverse phase LC-MS.

After lyophilisation the products were obtained as white powders and analysed by LC-MS. The analytical data comprising purity after preparative HPLC and ESI-MS are shown in Table 1.

Analytical Method:

Analytical HPLC retention times (RT, in minutes) were determined using an Jupiter Proteo 90A, 150×2.0 mm, (cod. 00F4396-B0—Phenomenex) with the following solvents A ($H_2O$+0.1% TFA) and B ($CH_3CN$+0.1% TFA) and the gradient: 0 min: 95% A, 5% B; 20 min: 40% A 60% B; 21-23 min: 0% A, 100% B; 23.1-30 min: 95% A, 5% B.

Procedure B: Cyclization and Work Up of Backbone Cyclized Peptides Having Disulfide β-Strand Linkages Formation of Disulfide β-Strand Linkage After completion of the synthesis, the resin was swelled in 3 ml of dry DMF for 1 h. Then 10 eq. of iodine solution in DMF (6 ml) were added to the reactor, followed by stirring for 1.5 h. The resin was filtered and a fresh solution of iodine (10 eq.) in DMF (6 ml) was added, followed by stirring for another 3 h. The resin was filtered and washed with DMF (3×) and CH$_2$Cl$_2$ (3×).

Backbone Cyclization, Cleavage and Purification of the Peptide

After formation of the disulfide β-strand linkage, the resin was suspended in 1 ml (0.39 mMol) of 1% TFA in CH$_2$Cl$_2$ (v/v) for 3 minutes and filtered, and the filtrate was neutralized with 1 ml (1.17 mMol, 3 eq.) of 20% DIEA in CH$_2$Cl$_2$ (v/v). This procedure was repeated twice to ensure completion of the cleavage. The resin was washed with 2 ml of CH$_2$Cl$_2$. The CH$_2$Cl$_2$ layer was evaporated to dryness.

The fully protected linear peptide was solubilized in 8 ml of dry DMF. Then 2 eq. of HATU in dry DMF (1 ml) and 4 eq. of DIPEA in dry DMF (1 ml) were added to the peptide, followed by stirring for 16 h. The volatiles were evaporated to dryness. The crude cyclized peptide was dissolved in 7 ml of CH$_2$Cl$_2$ and extracted with 10% acetonitrile in water (4.5 ml) three times. The CH$_2$Cl$_2$ layer was evaporated to dryness. To deprotect the peptide fully, 3 ml of cleavage cocktail TFA:TIS:H$_2$O (95:2.5:2.5) were added, and the mixture was kept for 2.5 h. The volatile was evaporated to dryness and the crude peptide was dissolved in 20% AcOH in water (7 ml) and extracted with diisopropyl ether (4 ml) for three times. The aqueous layer was collected and evaporated to dryness, and the residue was purified by preparative reverse phase LC-MS.

After lyophilisation the products were obtained as white powders and analysed by ESI-MS analytical method as described above. The analytical data comprising purity after preparative HPLC and ESI-MS are shown in Table 1.

Examples 1-45, 52-63, 65-67, 70-71, 75-114, 129, 131-162 and 179-196 are shown in Table 1. The peptides were synthesized starting with the amino acid Pro which was grafted to the resin. Starting resin was Fmoc-Pro-2-chlorotrityl resin, which was prepared as described above. The linear peptides were synthesized on solid support according to the procedure described above in the following sequence: Resin-Pro-$^D$Pro-P11-P10-P9-P8-P7-P6-P5-P4-P3-P2-P1. Ex. 1-6, 9-45, 52-63, 65-67, 70-71, 75-103 112-114, 129, 131, 133, 136-138, 140-141, 143-146, 148-153, 155, 157-162 and 179-196 were cleaved from the resin, subjected to the disulfide bridge formation, cyclized, deprotected and purified as indicated in procedure B. Ex. 82, 123, 149, 159, 161 and 178 were cleaved from the resin as indicated in procedure B. The disulfide bridges were formed using the following procedure:

The crude product was solubilized in an ammonium acetate buffer 0.1M (pH adjusted to 8) (concentration: 1 mg of crude product per ml). The mixture was stirred at room temperature in presence of air. The reaction was monitored by reverse phase LC-MS. After reaction completion, the solution was evaporated to dryness and the residue purified by preparative reverse phase LC-MS.

The cyclization of the backbone was performed as indicated in procedure A. The deprotection was performed using the following procedure:

To deprotect the peptide fully, 5 ml of cleavage cocktail TFA:H$_2$O:Phenol:Thioanisol: Ethanedithiol (82.5:5:5:5:2.5) were added, and the mixture was kept for 5 h at room temperature. The peptide was precipitated by addition of cold diethylether (10 ml). After centrifugation, the supernatant phase was removed. The precipitate was washed three times with 5 ml of diethylether and was purified by preparative reverse phase LC-MS.

After lyophilisation the products were obtained as white powders and analysed by ESI-MS analytical method as described above.

Ex. 7, 8, 104-111, 132, 134, 135, 139, 142, 147, 154 and 156 were cleaved from the resin, cyclized, deprotected and purified as indicated in procedure A.

HPLC-retention times (minutes) were determined using the analytical method as described above:

Ex. 1 (15.37), Ex. 2 (11.54), Ex. 3 (7.82), Ex. 4 (8.62), Ex. 5 (16.51), Ex. 6 (13.67), Ex. 7 (3.61), Ex. 8 (4.11), Ex. 9 (5.82), Ex. 10 (7.98), Ex. 11 (8.38), Ex. 12 (6.80), Ex. 13 (7.41), Ex. 14 (6.20), Ex. 15 (8.68), Ex. 16 (9.82); Ex. 17 (5.59), Ex. 20 (7.32), Ex. 21 (8.66), Ex. 22 (8.68), Ex. 23 (12.66), Ex. 24 (8.67), Ex. 25 (7.53), Ex. 26 (9.02), Ex. 27 (8.06), Ex. 28 (9.62), Ex. 29 (8.78), Ex. 30 (10.49), Ex. 31 (5.50), Ex. 32 (7.45), Ex. 33 (8.39), Ex. 34 (10.16), Ex. 35 (9.04), Ex. 36 (10.98), Ex. 37 (7.56), Ex. 38 (9.29), Ex. 39 (8.32), Ex. 40 (10.11), Ex. 41 (7.23), Ex. 42 (8.83), Ex. 43 (7.92), Ex. 44 (9.87), Ex. 45 (8.26), Ex. 52 (6.20), Ex. 53 (8.68), Ex 54 (9.82), Ex. 55 (5.59), Ex. 56 (6.06), Ex. 57 (6.47), Ex. 58 (7.32), Ex. 59 (8.68), Ex. 60 (10.66), Ex. 61 (8.54), Ex. 62 (9.83), Ex. 63 (16.54), Ex. 65 (15.71), Ex. 66 (17.50), Ex. 67 (15.87), Ex. 70 (12.87), Ex. 71 (13.48), Ex. 75 (14.22), Ex. 76 (4.47), Ex. 77 (5.15), Ex. 78 (10.93), Ex. 79 (10.70), Ex. 80 (12.09), Ex. 81 (11.63), Ex. 82 (5.71), Ex. 83 (5.45), Ex. 84 (11.14), Ex. 85 (10.90), Ex. 86 (13.78), Ex. 87 (13.98), Ex. 88 (14.35), Ex. 89 (15.21), Ex. 90 (14.72), Ex. 91 (11.97), Ex. 92 (11.77), Ex. 93 (15.25), Ex. 94 (14.61), Ex. 95 (20.46), Ex. 96 (15.08), Ex. 97 (20.78), Ex. 98 (18.28), Ex. 99 (14.62), Ex. 100 (13.90), Ex. 101 (13.76), Ex. 102 (20.53), Ex. 103 (14.14), Ex. 104 (11.60), Ex. 105 (11.90), Ex. 106 (11.63), Ex. 107 (11.78), Ex. 108 (13.03), Ex. 109 (15.22), Ex. 110 (12.40), Ex. 111 (12.10), Ex. 112 (5.49), Ex. 113 (5.67), Ex. 114 (5.55), Ex. 129 (17.22), Ex. 131 (11.97), Ex. 132 (13.56), Ex. 133 (14.57), Ex. 134 (14.72), Ex. 135 (17.53), Ex. 136 (18.28), Ex. 137 (14.72), Ex. 138 (14.35), Ex. 139 (15.40), Ex. 140 (11.14), Ex. 141 (5.71), Ex. 142 (13.97), Ex. 143 (13.94), Ex. 144 (15.08), Ex. 145 (20.87), Ex. 146 (17.91), Ex. 147 (17.11), Ex. 148 (7.83), Ex. 149 (16.22), Ex. 150 (20.09), Ex. 151 (20.72), Ex. 152 (21.38), Ex. 153 (17.97), Ex. 154 (16.58), Ex. 155 (19.46), Ex. 156 (15.66), Ex. 157 (22.04), Ex. 158 (15.65), Ex. 159 (17.89), Ex. 160 (18.72), Ex. 161 (19.91), Ex. 162 (17.79), Ex. 179 (4.25), Ex. 180 (11.43), Ex. 181 (12.30), Ex. 182 (12.83), Ex. 183 (10.51), Ex. 184 (12.12), Ex. 185 (10.14), Ex. 186 (10.09), Ex. 187 (10.14), Ex. 188 (10.65), Ex. 189 (10.73), Ex. 190 (10.10), Ex. 191 (10.17), Ex. 192 (10.19), Ex. 193 (11.02), Ex. 194 (9.92), Ex. 195 (10.74), Ex. 196 (9.94).

Example 46 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Asp(OtBu)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 46 (8.94).

Example 47 is shown in Table 1. The peptide was synthesized starting with the amino acid Asp which was grafted to the resin. Starting resin was Fmoc-Asp(OtBu)-2-chlorotrityl resin, which was prepared as described above. The linear peptide was synthesized on solid support according to procedure described above in the following sequence: Resin-Asp(OtBu)-$^D$Pro-P11-P10-P9-P8-P7-P6-P5-P4-P3-P2-P1.

Thereafter the disulfide bridge was formed, and the peptide was cleaved from the resin, cyclized, deprotected and purified as indicated in procedure B.

HPLC-retention time (minutes) was determined using the analytical method as described above:

Ex. 47 (7.29).

Example 48 is shown in Table 1. The peptide was synthesized starting with the amino acid Pro(5RPhe) which was grafted to the resin. Starting resin was Fmoc-Pro(5RPhe)-2-chlorotrityl resin, which was prepared as described above. The linear peptide was synthesized on solid support according to procedure described above in the following sequence: Resin-Pro(5RPhe)-$^D$Pro-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical described above:

Ex. 48 (10.07).

Example 49 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Ala-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 49 (8.09);

Example 50 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Ile-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical described above:

Ex. 50 (9.78).

Example 51 is shown in Table 1. The peptide was synthesized starting with the amino acid Leu which was grafted to the resin. Starting resin was Fmoc-Leu-2-chlorotrityl resin, which was prepared as described above. The linear peptide was synthesized on solid support according to procedure described above in the following sequence: Resin-Leu-$^D$Pro-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 51 (8.94);

Example 64 is shown in Table 1. The peptide was synthesized starting with the amino acid Glu which was grafted to the resin. Starting resin was Fmoc-Glu(OtBut)-2-chlorotrityl resin, which was prepared as described above. The linear peptide was synthesized on solid support according to procedure described above in the following sequence: Resin-Glu(OtBu)-$^D$Pro-P11-P10-P9-P8-P7-P6-P5-P4-P3-P2-P1.

Thereafter the disulfide bridge was formed, and the peptide was cleaved from the resin, cyclized, deprotected and purified as indicated in procedure B.

HPLC-retention time (minutes) was determined using the analytical method described above:

Ex. 64 (13.17).

Example 68 is shown in Table 1. The peptide was synthesized starting with the amino acid Asp which was grafted to the resin. Starting resin was Fmoc-Asp(OtBu)-2-chlorotrityl resin, which was prepared as described above. The linear peptide was synthesized on solid support according to procedure described above in the following sequence: Resin-Asp(OtBu)-$^D$Ala-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 68 (12.44).

Example 69 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin Pro-$^D$Asn(Trt)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 69 (12.97).

Example 72 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Thr(OtBu)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 72 (13.34).

Example 73 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Ile-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 73 (9.78).

Example 74 is shown in Table 1. The peptide was synthesized starting with the amino acid Leu which was grafted to the resin. Starting resin was Fmoc-Leu-2-chlorotrityl resin, which was prepared as described above. The linear peptide was synthesized on solid support according to procedure described above in the following sequence: Resin-Leu-$^D$Pro-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 74 (8.94).

Example 115 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Asp(OtBu)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 115 (4.82).

Example 116 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Phe-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 116 (5.98).

Example 117 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Arg(Trt)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 117 (4.48).

Example 118 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Ser(OtBu)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 118 (4.73).

Example 119 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Val-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 119 (5.47).

Example 120 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Pip-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the gradient method 1 described above:

Ex. 120 (5.48).

Example 121 is shown in Table 1. The peptide was synthesized starting with the amino acid Asp which was grafted to the resin. Starting resin was Fmoc-Asp(OtBu)-2-chlorotrityl resin, which was prepared as described above. The linear peptide was synthesized on solid support according to procedure described above in the following sequence: Resin-Asp(OtBu)-$^D$Pro-P11-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 121 (4.56).

Examples 122 and 167 are shown in Table 1. The peptides were synthesized starting with the amino acid Phe which was grafted to the resin. Starting resin was Fmoc-Phe-2-chlorotrityl resin, which was prepared as described above. The linear peptides were synthesized on solid support according to procedure described above in the following sequence: Resin-Phe-$^D$Pro-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 122 (5.75); 167 (5.75).

Examples 123, 164, 169, 170, 172, 173, 175, 177 and 178 are shown in Table 1. The peptides were synthesized starting with the amino acid Gln which was grafted to the resin. Starting resin was Fmoc-Gln(Trt)-2-chlorotrityl resin, which was prepared as described above. The linear peptides were synthesized on solid support according to procedure described above in the following sequence: Resin-Gln(Trt)-$^D$Pro-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 123 (4.35), 164 (13.20), 169 (16.81), 170 (14.57), 172 (16.78), 173 (13.57), 175 (15.94), 177 (16.78), 178 (17.45).

Example 124 is shown in Table 1. The peptide was synthesized starting with the amino acid Ser which was grafted to the resin. Starting resin was Fmoc-Ser(OtBu)-2-chlorotrityl resin, which was prepared as described above. The linear peptide was synthesized on solid support according to procedure described above in the following sequence: Resin-Ser(OtBu)-$^D$Pro-P11-P10-P9-P8-P7-P6-P5-P4-P3-P2-P1.

Thereafter the disulfide bridge was formed, and the peptide was cleaved from the resin, cyclized, deprotected and purified as indicated in procedure B.

HPLC-retention time (minutes) was determined using the analytical method described above:

Ex. 124 (4.46).

Example 125 is shown in Table 1. The peptide was synthesized starting with the amino acid Val which was grafted to the resin. Starting resin was Fmoc-Val-2-chlorotrityl resin, which was prepared as described above. The linear peptide was synthesized on solid support according to procedure described above in the following sequence: Resin-Val-$^D$Pro-P11-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 125 (18.42).

Example 126 is shown in Table 1. The peptide was synthesized starting with the amino acid Thr which was grafted to the resin. Starting resin was Fmoc-Thr(OtBu)-2-chlorotrityl resin, which was prepared as described above. The linear peptide was synthesized on solid support according to procedure described above in the following sequence: Resin-Thr(OtBu)-$^D$Thr(OtBu)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 126 (4.35).

Examples 127, 163, 165 and 174 are shown in Table 1. The peptides were synthesized starting with the amino acid Glu which was grafted to the resin. Starting resin was Fmoc-Glu(OtBu)-2-chlorotrityl resin, which was prepared as described above. The linear peptides were synthesized on solid support according to procedure described above in the following sequence: Resin-Glu(OtBu)-$^D$Lys(Boc)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 127 (4.11), 163 (14.93), 165 (14.40), 174 (12.73).

Example 128 is shown in Table 1. The peptide is synthesized starting with the amino acid Thr which was grafted to the resin. Starting resin was Fmoc-Thr(OtBu)-2-chlorotrityl resin, which was prepared as described above. The linear peptide was synthesized on solid support according to procedure described above in the following sequence: Resin-Thr(OtBu)-$^D$Phe-P11-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the gradient method 1 described above:

Ex. 128 (5.26).

Example 130 is shown in Table 1. The peptide was synthesized starting with the amino acid Pro which was grafted to the resin. Starting resin was Fmoc-Pro-2-chlorotrityl resin, which was prepared as described above. The linear peptide was synthesized on solid support according to procedure described above in the following sequence: Resin-Pro-$^D$Ala-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 130 (14.79).

Example 166 is shown in Table 1. The peptide was synthesized starting with the amino acid Ile which was grafted to the resin. Starting resin was Fmoc-Ile-2-chlorotrityl resin, which was prepared as described above. The linear peptide was synthesized on solid support according to procedure described above in the following sequence: Resin-Ile-$^D$Phe-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 166 (16.80).

Example 168 is shown in Table 1. The peptide was synthesized starting with the amino acid Asp which was grafted to the resin. Starting resin was Fmoc-Asp(OtBu)-2-chlorotrityl resin, which was prepared as described above. The linear peptide was synthesized on solid support according to procedure described above in the following sequence: Resin-Asp(OtBu)-$^D$Pro-P11-P10-P9-P8-P7-P6-P5-P4-P3-P2-P1.

Thereafter the disulfide bridge was formed, and the peptide was cleaved from the resin, cyclized, deprotected and purified as indicated in procedure B.

HPLC-retention time (minutes) was determined using the analytical described above:

Ex. 168 (4.56).

Examples 171 and 176 are shown in Table 1. The peptides were synthesized starting with the amino acid Gln which was grafted to the resin. Starting resin was Fmoc-Gln(Trt)-2-chlorotrityl resin, which was prepared as described above. The linear peptides were synthesized on solid support according to procedure described above in the following sequence: Resin-Gln(Trt)-$^D$Gln(Trt)-P11-P10-P9-P8-P7-P6-P5-P4-P3-P2-P1. Thereafter the disulfide bridge was formed, and the peptide was cleaved from the resin, cyclized, deprotected and purified as indicated in procedure B.

HPLC-retention time (minutes) was determined using the analytical method described above:

Ex. 171 (15.40), 176 (13.67).

TABLE 1

| | | Examples | | | | | | | |
|---|---|---|---|---|---|---|---|---|---|
| Example | Sequ.ID | P1 | P2 | P3 | P4 | P5 | P6 | P7 | P8 |
| 1 | SEQ ID NO: 1 | Phe | Cys | Thr | Lys | Ser | Glu | Pro | Pro |
| 2 | SEQ ID NO: 2 | Phe | Cys | Thr | Lys | Ser | Asp | Pro | Pro |
| 3 | SEQ ID NO: 3 | Phe | Cys | Thr | Lys | Ser | Asp | Pro | Pro |
| 4 | SEQ ID NO: 4 | Phe | Cys | Thr | Lys | Ser | Asp | Pro | Pro |
| 5 | SEQ ID NO: 5 | Phe | Cys | Thr | Lys | Ser | Asp | Pro | Pro |
| 6 | SEQ ID NO: 6 | Tyr | Cys | Thr | Lys | Ser | Asp | Pro | Pro |

TABLE 1-continued

| | | Examples | | | | | | | |
|---|---|---|---|---|---|---|---|---|---|
| 7 | SEQ ID NO: 7 | Arg | Glu | Thr | Lys | Ser | Asp | Pro | Pro |
| 8 | SEQ ID NO: 8 | Arg | Nle | Thr | Lys | Ser | Asp | Pro | Pro |
| 9 | SEQ ID NO: 9 | 4AmPhe | Cys | Thr | Lys | Ser | Asp | Pro | Pro |
| 10 | SEQ ID NO: 10 | Nle | Cys | Thr | Lys | Ser | Asp | Pro | Pro |
| 11 | SEQ ID NO: 11 | Chg | Cys | Thr | Lys | Ser | Asp | Pro | Pro |
| 12 | SEQ ID NO: 12 | Chg | Cys | Thr | Lys | Ser | Asp | Pro | Pro |
| 13 | SEQ ID NO: 13 | 2Cl-Phe | Cys | Thr | Lys | Ser | Asp | Pro | Pro |
| 14 | SEQ ID NO: 14 | Ile | Cys | Thr | Lys | Ser | Asp | Pro | Ala |
| 15 | SEQ ID NO: 15 | Phe | Cys | Thr | Lys | Ser | Asp | Pro | Pro |
| 16 | SEQ ID NO: 16 | Phe | Cys | Thr | Lys | Ser | Asp | Pro | Pro |
| 17 | SEQ ID NO: 17 | Ile | Cys | Thr | Lys | Ser | Asp | Pro | Pro |
| 18 | SEQ ID NO: 18 | Ile | Cys | Thr | Lys | Ser | Asp | Pro | Pro |
| 19 | SEQ ID NO: 19 | Ile | Cys | Thr | Lys | Ser | Asp | Pro | Pro |
| 20 | SEQ ID NO: 20 | Ile | Cys | Thr | Lys | Ser | Asp | Pro | Pro |
| 21 | SEQ ID NO: 21 | Phe | Cys | Thr | Lys | Ser | Glu | Pro | Pro |
| 22 | SEQ ID NO: 22 | Ile | Cys | Thr | Nle | Ser | Asp | Pro | Pro |
| 23 | SEQ ID NO: 23 | Phe | Cys | Thr | Nle | Ser | Asp | Pro | Pro |
| 24 | SEQ ID NO: 24 | Phe | Cys | Thr | Lys | AlloThr | Asp | Pro | Pro |
| 25 | SEQ ID NO: 25 | Phe | Cys | Thr | Lys | Dpr | Asp | Pro | Pro |
| 26 | SEQ ID NO: 26 | Tyr | Cys | Thr | Lys | Ser | Asp | Pro | Pro |
| 27 | SEQ ID NO: 27 | hPhe | Cys | Thr | Lys | Ser | Asp | Pro | Pro |
| 28 | SEQ ID NO: 28 | hPhe | Cys | Thr | Lys | Ser | Asp | Pro | Pro |
| 29 | SEQ ID NO: 29 | hPhe | Cys | Thr | Lys | Ser | Asp | Pro | Pro |
| 30 | SEQ ID NO: 30 | hPhe | Cys | Thr | Lys | Ser | Asp | Pro | Pro |
| 31 | SEQ ID NO: 31 | 4AmPhe | Cys | Thr | Lys | Ser | Asp | Pro | Pro |
| 32 | SEQ ID NO: 32 | 4AmPhe | Cys | Thr | Lys | Ser | Asp | Pro | Pro |
| 33 | SEQ ID NO: 33 | Cha | Cys | Thr | Lys | Ser | Asp | Pro | Pro |
| 34 | SEQ ID NO: 34 | Cha | Cys | Thr | Lys | Ser | Asp | Pro | Pro |
| 35 | SEQ ID NO: 35 | Cha | Cys | Thr | Lys | Ser | Asp | Pro | Pro |
| 36 | SEQ ID NO: 36 | Cha | Cys | Thr | Lys | Ser | Asp | Pro | Pro |
| 37 | SEQ ID NO: 37 | Chg | Cys | Thr | Lys | Ser | Asp | Pro | Pro |
| 38 | SEQ ID NO: 38 | Chg | Cys | Thr | Lys | Ser | Asp | Pro | Pro |
| 39 | SEQ ID NO: 39 | Chg | Cys | Thr | Lys | Ser | Asp | Pro | Pro |
| 40 | SEQ ID NO: 40 | Chg | Cys | Thr | Lys | Ser | Asp | Pro | Pro |
| 41 | SEQ ID NO: 41 | Nle | Cys | Thr | Lys | Ser | Asp | Pro | Pro |
| 42 | SEQ ID NO: 42 | Nle | Cys | Thr | Lys | Ser | Asp | Pro | Pro |
| 43 | SEQ ID NO: 43 | Nle | Cys | Thr | Lys | Ser | Asp | Pro | Pro |
| 44 | SEQ ID NO: 44 | Nle | Cys | Thr | Lys | Ser | Asp | Pro | Pro |
| 45 | SEQ ID NO: 45 | 2Cl-Phe | Cys | Thr | Lys | Ser | Asp | Pro | Pro |
| 46 | SEQ ID NO: 46 | Phe | Cys | Thr | Lys | Ser | Asp | Pro | Pro |
| 47 | SEQ ID NO: 47 | Phe | Cys | Thr | Lys | Ser | Asp | Pro | Pro |
| 48 | SEQ ID NO: 48 | Phe | Cys | Thr | Lys | Ser | Asp | Pro | Pro |
| 49 | SEQ ID NO: 49 | Phe | Cys | Thr | Lys | Ser | Asp | Pro | Pro |
| 50 | SEQ ID NO: 50 | Phe | Cys | Thr | Lys | Ser | Asp | Pro | Pro |
| 51 | SEQ ID NO: 51 | Phe | Cys | Thr | Lys | Ser | Asp | Pro | Pro |
| 52 | SEQ ID NO: 52 | Ile | Cys | Thr | Lys | Ser | Asp | Pro | Ala |
| 53 | SEQ ID NO: 53 | Phe | Cys | Thr | Lys | Ser | Asp | Pro | Pro |
| 54 | SEQ ID NO: 54 | Phe | Cys | Thr | Lys | Ser | Asp | Pro | Pro |
| 55 | SEQ ID NO: 55 | Ile | Cys | Thr | Lys | Ser | Asp | Pro | Pro |
| 56 | SEQ ID NO: 56 | Ile | Cys | Thr | Lys | Ser | Asp | Pro | Pro |
| 57 | SEQ ID NO: 57 | Ile | Cys | Thr | Lys | Ser | Asp | Pro | Pro |
| 58 | SEQ ID NO: 58 | Ile | Cys | Thr | Lys | Ser | Asp | Pro | Pro |
| 59 | SEQ ID NO: 59 | Ile | Cys | Thr | Nle | Ser | Asp | Pro | Pro |
| 60 | SEQ ID NO: 60 | Phe | Cys | Thr | Nle | Ser | Asp | Pro | Pro |
| 61 | SEQ ID NO: 61 | Trp | Cys | Thr | Lys | Ser | Asp | Pro | Pro |
| 62 | SEQ ID NO: 62 | 1-Nal | Cys | Thr | Lys | Ser | Asp | Pro | Pro |
| 63 | SEQ ID NO: 63 | Chg | Cys | Thr | Lys | Ser | Asp | Pro | Pro |
| 64 | SEQ ID NO: 64 | Phe | Cys | Thr | Lys | Ser | Asp | Pro | Pro |
| 65 | SEQ ID NO: 65 | Chg | Cys | Thr | Lys | Ser | Asp | Pro | Pro |
| 66 | SEQ ID NO: 66 | Chg | Cys | Thr | Lys | Ser | Asp | Pro | Pro |
| 67 | SEQ ID NO: 67 | Chg | Cys | Thr | Lys | AlloThr | Asp | Pro | Pro |
| 68 | SEQ ID NO: 68 | Phe | Cys | Thr | Lys | Ser | Asp | Pro | Pro |
| 69 | SEQ ID NO: 69 | Phe | Cys | Thr | Lys | Ser | Asp | Pro | Pro |
| 70 | SEQ ID NO: 70 | 4AmPhe | Cys | Thr | Lys | Ser | Asp | Pro | Pro |
| 71 | SEQ ID NO: 71 | Chg | Cys | Thr | Lys | Ser | Asp | Pro | Pro |
| 72 | SEQ ID NO: 72 | Phe | Cys | Thr | Lys | Ser | Asp | Pro | Pro |
| 73 | SEQ ID NO: 73 | Phe | Cys | Thr | Lys | Ser | Asp | Pro | Pro |
| 74 | SEQ ID NO: 74 | Phe | Cys | Thr | Lys | Ser | Asp | Pro | Pro |
| 75 | SEQ ID NO: 75 | Arg | Cys | Thr | Lys | Ser | Asp | Pro | Pro |
| 76 | SEQ ID NO: 76 | Ile | Cys | Thr | Ala | Ser | Leu | Pro | Pro |
| 77 | SEQ ID NO: 77 | Nle | Cys | Thr | Thr | Ser | Ile | Pro | Pro |
| 78 | SEQ ID NO: 78 | Nle | Cys | Thr | Abu | Ser | Ile | Pro | Pro |
| 79 | SEQ ID NO: 79 | Nle | Cys | Thr | Ala | Ser | Nle | Pro | Pro |
| 80 | SEQ ID NO: 80 | Nle | Cys | Thr | Ala | Ser | Aoc | Pro | Pro |
| 81 | SEQ ID NO: 81 | Nle | Cys | Thr | Ala | Ser | OctG | Pro | Pro |
| 82 | SEQ ID NO: 82 | Nle | Cys | Thr | Ala | Ser | Cha | Pro | Pro |
| 83 | SEQ ID NO: 83 | Nle | Cys | Thr | Ala | Ser | hLeu | Pro | Pro |
| 84 | SEQ ID NO: 84 | Nle | Cys | Thr | Ala | Ser | Chg | Pro | Pro |

TABLE 1-continued

| Examples | | | | | | | | | |
|---|---|---|---|---|---|---|---|---|---|
| 85 | SEQ ID NO: 85 | Nle | Cys | Thr | Ala | Ser | t-BuAla | Pro | Pro |
| 86 | SEQ ID NO: 86 | Nle | Cys | Ala | Ala | Ser | Ile | Pro | Pro |
| 87 | SEQ ID NO: 87 | Nle | Cys | Abu | Ala | Ser | Ile | Pro | Pro |
| 88 | SEQ ID NO: 88 | Nle | Cys | Thr | Ala | Ser | Ile | Pro | Pro(4NHCOPhe) |
| 89 | SEQ ID NO: 89 | Nle | Cys | Thr | Ala | Ser | Ile | Pro | Pro |
| 90 | SEQ ID NO: 90 | Nle | Cys | Thr | Ala | Ser | Ile | Pro | Pro |
| 91 | SEQ ID NO: 91 | Nle | Cys | Thr | Ala | Ser | Ile | Pro | Pro |
| 92 | SEQ ID NO: 92 | Nle | Cys | Thr | Ala | Ser | Ile | Pro | Pro |
| 93 | SEQ ID NO: 93 | Nle | Cys | Thr | Ala | Ser | Ile | Pro | Pro |
| 94 | SEQ ID NO: 94 | Nle | Cys | Thr | Ala | Ser | Ile | Pro | Pro |
| 95 | SEQ ID NO: 95 | Nle | Cys | Thr | Ala | Ser | Ile | Pro | Pro |
| 96 | SEQ ID NO: 96 | Nle | Cys | Thr | Ala | Ser | Ile | Pro | Pro |
| 97 | SEQ ID NO: 97 | Nle | Cys | Thr | Ala | Ser | Ile | Pro | Pro |
| 98 | SEQ ID NO: 98 | Nle | Cys | Thr | Ala | Ser | Ile | Pro | Pro |
| 99 | SEQ ID NO: 99 | Aoc | Cys | Thr | Ala | Ser | Ile | Pro | Pro |
| 100 | SEQ ID NO: 100 | hLeu | Cys | Thr | Ala | Ser | Ile | Pro | Pro |
| 101 | SEQ ID NO: 101 | Chg | Cys | Thr | Ala | Ser | Ile | Pro | Pro |
| 102 | SEQ ID NO: 102 | OctG | Cys | Thr | Ala | Ser | Ile | Pro | Pro |
| 103 | SEQ ID NO: 103 | hPhe | Cys | Thr | Ala | Ser | Ile | Pro | Pro |
| 104 | SEQ ID NO: 104 | Nle | Glu | Thr | Ala | Ser | Ile | Pro | Pro |
| 105 | SEQ ID NO: 105 | Nle | Glu | Thr | Ala | Ser | Ile | Pro | Pro |
| 106 | SEQ ID NO: 106 | Nle | Thr | Thr | Ala | Ser | Ile | Pro | Pro |
| 107 | SEQ ID NO: 107 | Nle | Gln | Thr | Ala | Ser | Ile | Pro | Pro |
| 108 | SEQ ID NO: 108 | Nle | Thr | Thr | Ala | Ser | Ile | Pro | Pro |
| 109 | SEQ ID NO: 109 | Nle | Gln | Thr | Ala | Ser | Ile | Pro | Pro |
| 110 | SEQ ID NO: 110 | Nle | Thr | Thr | Ala | Ser | Ile | Pro | Pro |
| 111 | SEQ ID NO: 111 | Nle | Gln | Thr | Ala | Ser | Ile | Pro | Pro |
| 112 | SEQ ID NO: 112 | Nle | Cys | Thr | Ala | Ser | C5al | Pro | Pro |
| 113 | SEQ ID NO: 113 | Nle | Cys | Thr | Ala | Ser | Leu | Pro | Pro |
| 114 | SEQ ID NO: 114 | Ile | Cys | Thr | Ala | Ser | Leu | Pro | Pro |
| 115 | SEQ ID NO: 115 | Nle | Cys | Thr | Ala | Ser | Ile | Pro | Pro |
| 116 | SEQ ID NO: 116 | Nle | Cys | Thr | Ala | Ser | Ile | Pro | Pro |
| 117 | SEQ ID NO: 117 | Nle | Cys | Thr | Ala | Ser | Ile | Pro | Pro |
| 118 | SEQ ID NO: 118 | Nle | Cys | Thr | Ala | Ser | Ile | Pro | Pro |
| 119 | SEQ ID NO: 119 | Nle | Cys | Thr | Ala | Ser | Ile | Pro | Pro |
| 120 | SEQ ID NO: 120 | Nle | Cys | Thr | Ala | Ser | Ile | Pro | Pro |
| 121 | SEQ ID NO: 121 | Nle | Cys | Thr | Ala | Ser | Ile | Pro | Pro |
| 122 | SEQ ID NO: 122 | Nle | Cys | Thr | Ala | Ser | Ile | Pro | Pro |
| 123 | SEQ ID NO: 123 | Nle | Cys | Thr | Ala | Ser | Ile | Pro | Pro |
| 124 | SEQ ID NO: 124 | Nle | Cys | Thr | Ala | Ser | Ile | Pro | Pro |
| 125 | SEQ ID NO: 125 | Nle | Cys | Thr | Ala | Ser | Ile | Pro | Pro |
| 126 | SEQ ID NO: 126 | Nle | Cys | Thr | Ala | Ser | Ile | Pro | Pro |
| 127 | SEQ ID NO: 127 | Nle | Cys | Thr | Ala | Ser | Ile | Pro | Pro |
| 128 | SEQ ID NO: 128 | Nle | Cys | Thr | Ala | Ser | Ile | Pro | Pro |
| 129 | SEQ ID NO: 129 | Nle | Cys | Thr | Ala | Ser | OctG | Pro | Pro |
| 130 | SEQ ID NO: 130 | Nle | Cys | Thr | Ala | Ser | Ile | Pro | Pro |
| 131 | SEQ ID NO: 131 | Nle | Cys | Thr | Ala | Ser | Ile | Pro | Pro |
| 132 | SEQ ID NO: 132 | hPhe | Glu | Thr | Ala | Ser | Ile | Pro | Pro |
| 133 | SEQ ID NO: 133 | Nle | Cys | Thr | Ala | Ser | Cha | Pro | Pro |
| 134 | SEQ ID NO: 134 | hPhe | Thr | Thr | Ala | Ser | Ile | Pro | Pro |
| 135 | SEQ ID NO: 135 | Nle | Thr | Thr | Ala | Ser | OctG | Pro | Pro |
| 136 | SEQ ID NO: 136 | Nle | Cys | Thr | Ala | Ser | Ile | Pro | Pro |
| 137 | SEQ ID NO: 137 | Nle | Cys | Thr | Ala | Ser | Ile | Pro | Pro |
| 138 | SEQ ID NO: 138 | Nle | Cys | Thr | Ala | Ser | Ile | Pro | Pro(4NHCOPhe) |
| 139 | SEQ ID NO: 139 | Nle | Thr | Thr | Ala | Ser | Cha | Pro | Pro |
| 140 | SEQ ID NO: 140 | Nle | Cys | Thr | Ala | Ser | Chg | Pro | Pro |
| 141 | SEQ ID NO: 141 | Nle | Cys | Thr | Ala | Ser | Cha | Pro | Pro |
| 142 | SEQ ID NO: 142 | hPhe | Gln | Thr | Ala | Ser | Ile | Pro | Pro |
| 143 | SEQ ID NO: 143 | hPhe | Cys | Thr | Ala | Ser | Ile | Pro | Pro |
| 144 | SEQ ID NO: 144 | Nle | Cys | Thr | Ala | Ser | Ile | Pro | Pro |
| 145 | SEQ ID NO: 145 | OctG | Cys | Thr | Ala | Ser | Ile | Pro | Pro |
| 146 | SEQ ID NO: 146 | hPhe | Cys | Thr | Ala | Ser | Ile | Pro | Pro |
| 147 | SEQ ID NO: 147 | OctG | Thr | Thr | Ala | Ser | Ile | Pro | Pro |
| 148 | SEQ ID NO: 148 | OctG | Cys | Thr | Ala | Ser | OctG | Pro | Pro |
| 149 | SEQ ID NO: 149 | OctG | Cys | Thr | Ala | Ser | Ile | Pro | Pro |
| 150 | SEQ ID NO: 150 | OctG | Cys | Thr | Ala | Ser | Cha | Pro | Pro |
| 151 | SEQ ID NO: 151 | OctG | Cys | Thr | Ala | Ser | OctG | Pro | Pro(4NHCOPhe) |
| 152 | SEQ ID NO: 152 | hPhe | Cys | Thr | Ala | Ser | OctG | Pro | Pro |
| 153 | SEQ ID NO: 153 | hPhe | Cys | Thr | Ala | Ser | OctG | Pro | Pro |
| 154 | SEQ ID NO: 154 | OctG | Gln | Thr | Ala | Ser | Ile | Pro | Pro |
| 155 | SEQ ID NO: 155 | hPhe | Cys | Thr | Ala | Ser | Cha | Pro | Pro |
| 156 | SEQ ID NO: 156 | OctG | Glu | Thr | Ala | Ser | Ile | Pro | Pro |
| 157 | SEQ ID NO: 157 | OctG | Cys | Thr | Ala | Ser | Cha | Pro | Pro |
| 158 | SEQ ID NO: 158 | hPhe | Cys | Thr | Ala | Ser | Cha | Pro | Pro |
| 159 | SEQ ID NO: 159 | OctG | Cys | Thr | Ala | Ser | Cha | Pro | Pro |
| 160 | SEQ ID NO: 160 | OctG | Cys | Thr | Ala | Ser | Cha | Pro | Pro(4NHCOPhe) |
| 161 | SEQ ID NO: 161 | hPhe | Cys | Thr | Ala | Ser | OctG | Pro | Pro |
| 162 | SEQ ID NO: 162 | hPhe | Cys | Thr | Ala | Ser | Cha | Pro | Pro |

TABLE 1-continued

Examples

| | | | | | | | | |
|---|---|---|---|---|---|---|---|---|
| 163 | SEQ ID NO: 163 | Nle | Cys | Thr | Ala | Ser | OctG | Pro Pro |
| 164 | SEQ ID NO: 164 | Nle | Cys | Thr | Ala | Ser | Cha | Pro Pro |
| 165 | SEQ ID NO: 165 | OctG | Cys | Thr | Ala | Ser | Ile | Pro Pro |
| 166 | SEQ ID NO: 166 | Nle | Cys | Thr | Ala | Ser | Ile | Pro Pro |
| 167 | SEQ ID NO: 167 | Nle | Cys | Thr | Ala | Ser | Ile | Pro Pro |
| 168 | SEQ ID NO: 168 | Nle | Cys | Thr | Ala | Ser | Ile | Pro Pro |
| 169 | SEQ ID NO: 169 | Nle | Cys | Thr | Ala | Ser | OctG | Pro Pro |
| 170 | SEQ ID NO: 170 | Nle | Cys | Thr | Ala | Ser | Cha | Pro Pro |
| 171 | SEQ ID NO: 171 | Nle | Cys | Thr | Ala | Ser | Cha | Pro Pro |
| 172 | SEQ ID NO: 172 | Nle | Cys | Thr | Ala | Ser | Cha | Pro Pro |
| 173 | SEQ ID NO: 173 | hPhe | Cys | Thr | Ala | Ser | Ile | Pro Pro |
| 174 | SEQ ID NO: 174 | hPhe | Cys | Thr | Ala | Ser | Ile | Pro Pro |
| 175 | SEQ ID NO: 175 | Nle | Cys | Thr | Ala | Ser | Cha | Pro Pro |
| 176 | SEQ ID NO: 176 | Nle | Cys | Thr | Ala | Ser | Cha | Pro Pro(4NHCOPhe) |
| 177 | SEQ ID NO: 177 | OctG | Cys | Thr | Ala | Ser | Ile | Pro Pro |
| 178 | SEQ ID NO: 178 | OctG | Cys | Thr | Ala | Ser | OctG | Pro Pro |
| 179 | SEQ ID NO: 179 | Nle | Cys | Thr | Ala | Ser | Ile | Pro Pro |
| 180 | SEQ ID NO: 180 | Ile | Cys | Thr | Lys | Ser | Leu | Pro Pro |
| 181 | SEQ ID NO: 181 | Ile | Cys | Thr | Lys | Ser | hPhe | Pro Pro |
| 182 | SEQ ID NO: 182 | Ile | Cys | Thr | Lys | Ser | Cha | Pro Pro |
| 183 | SEQ ID NO: 183 | Ile | Cys | Thr | Lys | Ser | Tyr | Pro Pro |
| 184 | SEQ ID NO: 184 | Phe | Cys | Thr | Lys | Ser | Leu | Pro Pro |
| 185 | SEQ ID NO: 185 | Ile | Cys | Thr | Lys | Ser | Leu | Pro Pro |
| 186 | SEQ ID NO: 186 | Ile | Cys | Thr | Lys | Ser | Leu | Pro Pro |
| 187 | SEQ ID NO: 187 | Ile | Cys | Thr | Lys | Ser | Leu | Pro Pro |
| 188 | SEQ ID NO: 188 | Ile | Cys | Thr | Lys | Ser | Leu | Pro Pro |
| 189 | SEQ ID NO: 189 | Ile | Cys | Thr | Lys | Ser | Leu | Pro Pro |
| 190 | SEQ ID NO: 190 | Ile | Cys | Thr | Lys | Ser | Leu | Pro Pro |
| 191 | SEQ ID NO: 191 | Leu | Cys | Thr | Lys | Ser | Leu | Pro Pro |
| 192 | SEQ ID NO: 192 | Nle | Cys | Thr | Lys | Ser | Leu | Pro Pro |
| 193 | SEQ ID NO: 193 | Cha | Cys | Thr | Lys | Ser | Leu | Pro Pro |
| 194 | SEQ ID NO: 194 | Tyr | Cys | Thr | Lys | Ser | Leu | Pro Pro |
| 195 | SEQ ID NO: 195 | Trp | Cys | Thr | Lys | Ser | Leu | Pro Pro |
| 196 | SEQ ID NO: 196 | Arg | Cys | Thr | Lys | Ser | Leu | Pro Pro |

| Example | P9 | P10 | P11 | Template | Purity %[a] | [M + H] |
|---|---|---|---|---|---|---|
| 1 | Ile | Cys | Thr | $^D$Pro$^L$Pro | 95 | 1385.7 |
| 2 | Ile | Cys | Asp | $^D$Pro$^L$Pro | 93 | 1399.5 |
| 3 | Ile | Cys | Asn | $^D$Pro$^L$Pro | 95 | 1398.5 |
| 4 | Ile | Cys | Ser | $^D$Pro$^L$Pro | 95 | 1371.1 |
| 5 | Ile | Cys | Tyr | $^D$Pro$^L$Pro | 95 | 1447.5 |
| 6 | Ile | Cys | Thr | $^D$Pro$^L$Pro | 95 | 1401.7 |
| 7 | Ile | Arg | Phe | $^D$Pro$^L$Pro | 95 | 1521.2 |
| 8 | Ile | Nle | Phe | $^D$Pro$^L$Pro | 95 | 1462.4 |
| 9 | Ile | Cys | Ser | $^D$Pro$^L$Pro | 92 | 1386.9 |
| 10 | Ile | Cys | Ser | $^D$Pro$^L$Pro | 93 | 1337.8 |
| 11 | Ile | Cys | Ser | $^D$Pro$^L$Pro | 95 | 1363.8 |
| 12 | Ile | Cys | Arg | $^D$Pro$^L$Pro | 95 | 1432.7 |
| 13 | Ile | Cys | Arg | $^D$Pro$^L$Pro | 95 | 1474.5 |
| 14 | Ile | Cys | Arg | $^D$Pro$^L$Pro | 93 | 1380.5 |
| 15 | Nle | Cys | Ser | $^D$Pro$^L$Pro | 95 | 1371.8 |
| 16 | Cha | Cys | Ser | $^D$Pro$^L$Pro | 95 | 1411.6 |
| 17 | Gln | Cys | Arg | $^D$Pro$^L$Pro | 95 | 1421.6 |
| 18 | Tyr | Cys | Arg | $^D$Pro$^L$Pro | 89 | 1456.6 |
| 19 | Nle | Cys | Arg | $^D$Pro$^L$Pro | 95 | 1476.6 |
| 20 | Cha | Cys | Arg | $^D$Pro$^L$Pro | 95 | 1446.5 |
| 21 | Ile | Cys | Ser | $^D$Pro$^L$Pro | 95 | 1385.8 |
| 22 | Ile | Cys | Arg | $^D$Pro$^L$Pro | 95 | 1391.6 |
| 23 | Ile | Cys | Tyr | $^D$Pro$^L$Pro | 95 | 1432.7 |
| 24 | Ile | Cys | Ser | $^D$Pro$^L$Pro | 95 | 1385.7 |
| 25 | Ile | Cys | Ser | $^D$Pro$^L$Pro | 95 | 1370.9 |
| 26 | Ile | Cys | Tyr | $^D$Pro$^L$Pro | 95 | 1463.8 |
| 27 | Ile | Cys | Asn | $^D$Pro$^L$Pro | 95 | 1412.6 |
| 28 | Ile | Cys | Thr | $^D$Pro$^L$Pro | 95 | 1399.7 |
| 29 | Ile | Cys | Asp | $^D$Pro$^L$Pro | 95 | 1413.6 |
| 30 | Ile | Cys | Tyr | $^D$Pro$^L$Pro | 95 | 1461.7 |
| 31 | Ile | Cys | Asn | $^D$Pro$^L$Pro | 91 | 1413.8 |
| 32 | Ile | Cys | Tyr | $^D$Pro$^L$Pro | 93 | 1462.7 |
| 33 | Ile | Cys | Asn | $^D$Pro$^L$Pro | 94 | 1404.8 |
| 34 | Ile | Cys | Thr | $^D$Pro$^L$Pro | 95 | 1391.7 |
| 35 | Ile | Cys | Asp | $^D$Pro$^L$Pro | 95 | 1405.8 |
| 36 | Ile | Cys | Tyr | $^D$Pro$^L$Pro | 95 | 1453.8 |
| 37 | Ile | Cys | Asn | $^D$Pro$^L$Pro | 95 | 1390.7 |
| 38 | Ile | Cys | Thr | $^D$Pro$^L$Pro | 95 | 1377.6 |
| 39 | Ile | Cys | Asp | $^D$Pro$^L$Pro | 95 | 1391.6 |
| 40 | Ile | Cys | Tyr | $^D$Pro$^L$Pro | 95 | 1439.6 |
| 41 | Ile | Cys | Asn | $^D$Pro$^L$Pro | 95 | 1364.7 |

TABLE 1-continued

| Examples | | | | | | |
|---|---|---|---|---|---|---|
| 42 | Ile | Cys | Thr | $^D$Pro$^L$Pro | 93 | 1351.7 |
| 43 | Ile | Cys | Asp | $^D$Pro$^L$Pro | 95 | 1365.7 |
| 44 | Ile | Cys | Tyr | $^D$Pro$^L$Pro | 95 | 1413.6 |
| 45 | Ile | Cys | Asn | $^D$Pro$^L$Pro | 95 | 1432.6 |
| 46 | Ile | Cys | Ser | $^D$Pro$^L$Pro | 95 | 1389.6 |
| 47 | Ile | Cys | Ser | $^D$Pro$^L$Asp | 95 | 1389.6 |
| 48 | Ile | Cys | Ser | $^D$Pro$^L$Pro(5RPhe) | 95 | 1447.5 |
| 49 | Ile | Cys | Ser | $^D$Ala$^L$Pro | 95 | 1345.6 |
| 50 | Ile | Cys | Ser | $^D$Ile$^L$Pro | 94 | 1387.9 |
| 51 | Ile | Cys | Ser | $^D$Pro$^L$Leu | 94 | 1395.7 |
| 52 | Ile | Cys | Arg | $^D$Pro$^L$Pro | 93 | 1380.7 |
| 53 | Nle | Cys | Ser | $^D$Pro$^L$Pro | 95 | 1371.8 |
| 54 | Cha | Cys | Ser | $^D$Pro$^L$Pro | 95 | 1411.6 |
| 55 | Gln | Cys | Arg | $^D$Pro$^L$Pro | 95 | 1421.6 |
| 56 | Tyr | Cys | Arg | $^D$Pro$^L$Pro | 89 | 1456.5 |
| 57 | Nle | Cys | Arg | $^D$Pro$^L$Pro | 94 | 1406.6 |
| 58 | Cha | Cys | Arg | $^D$Pro$^L$Pro | 95 | 1446.5 |
| 59 | Ile | Cys | Arg | $^D$Pro$^L$Pro | 95 | 1391.6 |
| 60 | Ile | Cys | Tyr | $^D$Pro$^L$Pro | 95 | 1432.7 |
| 61 | Ile | Cys | Ser | $^D$Pro$^L$Pro | 95 | 1410.9 |
| 62 | Ile | Cys | Ser | $^D$Pro$^L$Pro | 95 | 1421.9 |
| 63 | Nle | Cys | Tyr | $^D$Pro$^L$Pro | 95 | 1439. |
| 64 | Ile | Cys | Ser | $^D$Pro$^L$Glu | 95 | 1403.8 |
| 65 | Tyr | Cys | Tyr | $^D$Pro$^L$Pro | 95 | 1489.5 |
| 66 | Cha | Cys | Tyr | $^D$Pro$^L$Pro | 95 | 1479.6 |
| 67 | Tyr | Cys | Tyr | $^D$Pro$^L$Pro | 95 | 1503.6 |
| 68 | Ile | Cys | Ser | $^D$Ala$^L$Asp | 95 | 1363.6 |
| 69 | Ile | Cys | Ser | $^D$Asn$^L$Pro | 90 | 1388.8 |
| 70 | Cha | Cys | Asn | $^D$Pro$^L$Pro | 92 | 1454.5 |
| 71 | Cha | Cys | Arg | $^D$Pro$^L$Pro | 95 | 1472.6 |
| 72 | Ile | Cys | Ser | $^D$Thr$^L$Pro | 95 | 1375.6 |
| 73 | Ile | Cys | Ser | $^D$Ile$^L$Pro | 94 | 1387.9 |
| 74 | Ile | Cys | Ser | $^D$ProLeu | 94 | 1387.9 |
| 75 | Ile | Cys | Phe | $^D$Pro$^L$Pro | 95 | 1440.5 |
| 76 | Gln | Cys | Tyr | $^D$Pro$^L$Pro | 95 | 1369.3 |
| 77 | Tyr | Cys | Tyr | $^D$Pro$^L$Pro | 95 | 1434.3 |
| 78 | Gln | Cys | Tyr | $^D$Pro$^L$Pro | 95 | 1383.6 |
| 79 | Gln | Cys | Tyr | $^D$Pro$^L$Pro | 95 | 1369.8 |
| 80 | Gln | Cys | Tyr | $^D$Pro$^L$Pro | 95 | 1397.6 |
| 81 | Gln | Cys | Tyr | $^D$Pro$^L$Pro | 95 | 1425.6 |
| 82 | Gln | Cys | Tyr | $^D$Pro$^L$Pro | 95 | 1409.5 |
| 83 | Gln | Cys | Tyr | $^D$Pro$^L$Pro | 95 | 1383.6 |
| 84 | Gln | Cys | Tyr | $^D$Pro$^L$Pro | 95 | 1395.7 |
| 85 | Gln | Cys | Tyr | $^D$Pro$^L$Pro | 95 | 1383.6 |
| 86 | Gln | Cys | Tyr | $^D$Pro$^L$Pro | 95 | 1340.1 |
| 87 | Gln | Cys | Tyr | $^D$Pro$^L$Pro | 95 | 1354.0 |
| 88 | Gln | Cys | Tyr | $^D$Pro$^L$Pro | 95 | 1488.6 |
| 89 | Phe | Cys | Tyr | $^D$Pro$^L$Pro | 88 | 1388.7 |
| 90 | Gln | Cys | Phe | $^D$Pro$^L$Pro | 95 | 1353.6 |
| 91 | Gln | Cys | Gln | $^D$Pro$^L$Pro | 95 | 1334.5 |
| 92 | Gln | Cys | Arg | $^D$Pro$^L$Pro | 56 | 1362.6 |
| 93 | Gln | Cys | Ser | $^D$Pro$^L$Pro | 95 | 1293.7 |
| 94 | Gln | Cys | Nle | $^D$Pro$^L$Pro | 95 | 1319.5 |
| 95 | Gln | Cys | 2-Nal | $^D$Pro$^L$Pro | 94 | 1404.0 |
| 96 | Gln | Cys | 2Cl-Phe | $^D$Pro$^L$Pro | 94 | 1387.8 |
| 97 | Gln | Cys | Cha | $^D$Pro$^L$Pro | 95 | 1359.8 |
| 98 | Gln | Cys | Phg | $^D$Pro$^L$Pro | 95 | 1359.9 |
| 99 | Gln | Cys | Tyr | $^D$Pro$^L$Pro | 93 | 1397.4 |
| 100 | Gln | Cys | Try | $^D$Pro$^L$Pro | 95 | 1383.4 |
| 101 | Gln | Cys | Tyr | $^D$Pro$^L$Pro | 87 | 1395.6 |
| 102 | Gln | Cys | Tyr | $^D$Pro$^L$Pro | 95 | 1425.5 |
| 103 | Gln | Cys | Tyr | $^D$Pro$^L$Pro | 95 | 1417.5 |
| 104 | Gln | Lys | Tyr | $^D$Pro$^L$Pro | 95 | 1422.8 |
| 105 | Gln | Arg | Tyr | $^D$Pro$^L$Pro | 95 | 1450.9 |
| 106 | Gln | Lys | Tyr | $^D$Pro$^L$Pro | 95 | 1394.7 |
| 107 | Gln | Arg | Tyr | $^D$Pro$^L$Pro | 90 | 1449.8 |
| 108 | Gln | Met | Tyr | $^D$Pro$^L$Pro | 96 | 1397.7 |
| 109 | Gln | Thr | Tyr | $^D$Pro$^L$Pro | 95 | 1394.7 |
| 110 | Gln | Gln | Tyr | $^D$Pro$^L$Pro | 81 | 1394.6 |
| 111 | Gln | Ser | Tyr | $^D$Pro$^L$Pro | 95 | 1380.7 |
| 112 | Gln | Cys | Tyr | $^D$Pro$^L$Pro | 85 | 1413.8 |
| 113 | Tyr | Cys | Tyr | $^D$Pro$^L$Pro | 95 | 1404.7 |
| 114 | Tyr | Cys | Tyr | $^D$Pro$^L$Pro | 95 | 1404.7 |
| 115 | Gln | Cys | Tyr | $^D$Asp$^L$Pro | 95 | 1387.8 |
| 116 | Gln | Cys | Tyr | $^D$Phe$^L$Pro | 95 | 1419.9 |
| 117 | Gln | Cys | Tyr | $^D$Arg$^L$Pro | 95 | 1428.6 |
| 118 | Gln | Cys | Tyr | $^D$Ser$^L$Pro | 95 | 1359.9 |
| 119 | Gln | Cys | Tyr | $^D$Val$^L$Pro | 95 | 1371.8 |

TABLE 1-continued

| Examples | | | | | | |
|---|---|---|---|---|---|---|
| 120 | Gln | Cys | Tyr | $^D$Pic$^L$Pro | 95 | 1383.7 |
| 121 | Gln | Cys | Tyr | $^D$Pro$^L$Asp | 95 | 1387.9 |
| 122 | Gln | Cys | Tyr | $^D$Pro$^L$Phe | 95 | 1419.9 |
| 123 | Gln | Cys | Tyr | $^D$Pro$^L$Gln | 95 | 1400.6 |
| 124 | Gln | Cys | Tyr | $^D$Pro$^L$Ser | 95 | 1359.5 |
| 125 | Gln | Cys | Tyr | $^D$Pro$^L$Val | 95 | 1371.8 |
| 126 | Gln | Cys | Tyr | $^D$Thr$^L$Thr | 95 | 1377.4 |
| 127 | Gln | Cys | Tyr | $^D$Lys$^L$Glu | 95 | 1433.5 |
| 128 | Gln | Cys | Tyr | $^D$Phe$^L$Thr | 95 | 1423.5 |
| 129 | Gln | Cys | Gln | $^D$Pro$^L$Pro | 91 | 1390.4 |
| 130 | Gln | Cys | Tyr | $^D$Ala$^L$Pro | 95 | 1343.5 |
| 131 | Gln | Cys | Gln | $^D$Pro$^L$Pro | 95 | 1334.5 |
| 132 | Gln | Lys | Tyr | $^D$Pro$^L$Pro | 95 | 1470.6 |
| 133 | Gln | Cys | Gln | $^D$Pro$^L$Pro | 95 | 1440.5 |
| 134 | Gln | Gln | Tyr | $^D$Pro$^L$Pro | 95 | 1442.5 |
| 135 | Gln | Gln | Tyr | $^D$Pro$^L$Pro | 88 | 1450.7 |
| 136 | Gln | Cys | Phg | $^D$Pro$^L$Pro | 95 | 1339.9 |
| 137 | Gln | Cys | Phe | $^D$Pro$^L$Pro | 95 | 1353.6 |
| 138 | Gln | Cys | Tyr | $^D$Pro$^L$Pro | 95 | 1488.6 |
| 139 | Gln | Gln | Tyr | $^D$Pro$^L$Pro | 95 | 1434.8 |
| 140 | Gln | Cys | Tyr | $^D$Pro$^L$Pro | 95 | 1395.7 |
| 141 | Gln | Cys | Tyr | $^D$Pro$^L$Pro | 95 | 1409.5 |
| 142 | Gln | Thr | Tyr | $^D$Pro$^L$Pro | 91 | 1406.5 |
| 143 | Gln | Cys | Gln | $^D$Pro$^L$Pro | 94 | 1383.5 |
| 144 | Gln | Cys | 2Cl-Phe | $^D$Pro$^L$Pro | 94 | 1387.8 |
| 145 | Gln | Cys | Phe | $^D$Pro$^L$Pro | 95 | 1409.4 |
| 146 | Gln | Cys | Phe | $^D$Pro$^L$Pro | 95 | 1401.5 |
| 147 | Gln | Gln | Tyr | $^D$Pro$^L$Pro | 95 | 1450.9 |
| 148 | Gln | Cys | Gln | $^D$Pro$^L$Pro | 95 | 1446.6 |
| 149 | Gln | Cys | Gln | $^D$Pro$^L$Pro | 95 | 1390.4 |
| 150 | Gln | Cys | Tyr | $^D$Pro$^L$Pro | 95 | 1465.6 |
| 151 | Gln | Cys | Gln | $^D$Pro$^L$Pro | 94 | 1565.7 |
| 152 | Gln | Cys | Phe | $^D$Pro$^L$Pro | 95 | 1457.6 |
| 153 | Gln | Cys | Gln | $^D$Pro$^L$Pro | 95 | 1438.5 |
| 154 | Gln | Thr | Tyr | $^D$Pro$^L$Pro | 93 | 1450.9 |
| 155 | Gln | Cys | Phe | $^D$Pro$^L$Pro | 90 | 1441.5 |
| 156 | Gln | Lys | Tyr | $^D$Pro$^L$Pro | 95 | 1478.7 |
| 157 | Gln | Cys | Phe | $^D$Pro$^L$Pro | 95 | 1449.8 |
| 158 | Gln | Cys | Gln | $^D$Pro$^L$Pro | 94 | 1422.7 |
| 159 | Gln | Cys | Gln | $^D$Pro$^L$Pro | 93 | 1430.0 |
| 160 | Gln | Cys | Gln | $^D$Pro$^L$Pro | 95 | 1549.6 |
| 161 | Gln | Cys | Tyr | $^D$Pro$^L$Pro | 95 | 1473.4 |
| 162 | Gln | Cys | Tyr | $^D$Pro$^L$Pro | 95 | 1457.3 |
| 163 | Gln | Cys | Tyr | $^D$Lys$^L$Glu | 95 | 1374.4 |
| 164 | Gln | Cys | Gln | $^D$Pro$^L$Gln | 95 | 1405.5 |
| 165 | Gln | Cys | Tyr | $^D$Lys$^L$Glu | 95 | 1488.0 |
| 166 | Gln | Cys | Tyr | $^D$Pro$^L$Ile | 95 | 1385.6 |
| 167 | Gln | Cys | Tyr | $^D$Pro$^L$Phe | 95 | 1419.9 |
| 168 | Gln | Cys | Tyr | $^D$Pro$^L$Asp | 95 | 1387.9 |
| 169 | Gln | Cys | Tyr | $^D$Pro$^L$Gln | 95 | 1456.5 |
| 170 | Gln | Cys | Tyr | $^D$Pro$^L$Gln | 95 | 1440.5 |
| 171 | Gln | Cys | Cha | $^D$Gln$^L$Gln | 95 | 1461.0 |
| 172 | Gln | Cys | Cha | $^D$Pro$^L$Gln | 95 | 1430.6 |
| 173 | Gln | Cys | Tyr | $^D$Pro$^L$Gln | 95 | 1448.6 |
| 174 | Gln | Cys | Tyr | $^D$Lys$^L$Glu | 95 | 1480.0 |
| 175 | Gln | Cys | 2Cl-Phe | $^D$Pro$^L$Gln | 95 | 1458.5 |
| 176 | Gln | Cys | Gln | $^D$Gln$^L$Gln | 95 | 1555.5 |
| 177 | Gln | Cys | Tyr | $^D$Pro$^L$Gln | 95 | 1430.6 |
| 178 | Gln | Cys | Gln | $^D$Pro$^L$Gln | 95 | 1477.6 |
| 179 | Gln | Cys | Tyr | $^D$Pro$^L$Pro | 90 | 1369.7 |
| 180 | Ile | Cys | Arg | $^D$Pro$^L$Pro | 94 | 1404.8 |
| 181 | Ile | Cys | Arg | $^D$Pro$^L$Pro | 92 | 1452.6 |
| 182 | Ile | Cys | Arg | $^D$Pro$^L$Pro | 95 | 1444.6 |
| 183 | Ile | Cys | Arg | $^D$Pro$^L$Pro | 91 | 1454.5 |
| 184 | Ile | Cys | Arg | $^D$Pro$^L$Pro | 95 | 1438.6 |
| 185 | Arg | Cys | Arg | $^D$Pro$^L$Pro | 95 | 1447.5 |
| 186 | Lys | Cys | Arg | $^D$Pro$^L$Pro | 95 | 1419.9 |
| 187 | His | Cys | Arg | $^D$Pro$^L$Pro | 95 | 1428.6 |
| 188 | Gln | Cys | Arg | $^D$Pro$^L$Pro | 95 | 1419.8 |
| 189 | Thr | Cys | Arg | $^D$Pro$^L$Pro | 95 | 1392.4 |
| 190 | Arg | Cys | Lys | $^D$Pro$^L$Pro | 95 | 1420.1 |
| 191 | Lys | Cys | Arg | $^D$Pro$^L$Pro | 95 | 1420.0 |
| 192 | Lys | Cys | Arg | $^D$Pro$^L$Pro | 95 | 1420.0 |
| 193 | Lys | Cys | Arg | $^D$Pro$^L$Pro | 95 | 1459.7 |
| 194 | Lys | Cys | Arg | $^D$Pro$^L$Pro | 95 | 1469.6 |

TABLE 1-continued

| Examples | | | | | | |
|---|---|---|---|---|---|---|
| 195 | Lys | Cys | Arg | $^{D}$Pro$^{L}$Pro | 92 | 1492.6 |
| 196 | Lys | Cys | Tyr | $^{D}$Pro$^{L}$Pro | 95 | 1469.6 |

$^{a)}$%-purity of compounds after prep. HPLC
Cys in pos. 2 and 10 in Ex. 1-6, 9-103, 112-131, 133, 136-138, 140-141, 143-146, 148-153, 155, 157-196 form a disulfide bridge

2. Biological Methods

2.1. Preparation of the Peptide Samples.

Lyophilized peptides were weighed on a Microbalance (Mettler MT5) and dissolved in sterile water to a final concentration of 1 mM unless stated otherwise. Stock solutions were kept at +4° C., light protected.

2.2. Enzymatic Assays

Enzyme and substrate conditions were as indicated Table 2.

Kinetic measurements were made in a total reaction volume of 100 µl in 96 well flat bottomed plates (Greiner) on a Genios plate reader (Tecan). The enzyme was combined with the peptides (inhibitors) in a buffer containing 100 mM HEPES (pH 7.5), 50 mM $CaCl_2$, 0.025% Tween-20, 5% DMSO, and 1 mM of the substrate. The rate of substrate hydrolysis was measured by monitoring the change in absorbance at 405 nm over 30 minutes to verify linearity of the reaction curve. The average rate from minute 1 through minute 10 was used for all calculations. Initial calculations of background subtraction, average rate, duplicate averaging and % inhibition were made using the Magellan software (version 5) from Tecan. IC50% calculations were made using Grafit (version 5.0.10) from Erithacus Software by fitting inhibition data from 6 different inhibitor concentrations to a 4-parameter equation:

$$y = \frac{100\%}{1+\left(\frac{x}{IC_{50}}\right)^s}$$

In this equation s is the slope factor, x is the inhibitor concentration and y is % inhibition at a given concentration of the inhibitor.

$K_m/K_i$ Determination

The $K_m$ for the serine protease substrate was determined from a Lineweaver-Burke plot (Grafit v5). The $K_i$ values for inhibitors were calculated using the formula $K_i$=IC50%/(1+ ([substrate] $K_m$)).

Increasing concentrations of substrate were reacted with the enzyme and the rate of each reaction (ABS/mSec) was plotted vs. substrate concentration. The reciprocal plot (Lineweaver-Burke) was also plotted to give $K_m$ and $V_{max}$ (inset) (see ref. 1 below).

TABLE 2

| Enzyme/ Supplier | Enzyme concentration in assay | Substrate/ Supplier | Substrate concentration in assay (mM) |
|---|---|---|---|
| Elastase from human neutrophils/Serva | 0.6 mU/reaction | N-Met-Ala-Pro-Val-p-nitroanilide/Sigma | 1 |
| CathepsinG, from human neutrophils CAS nr. 107200-92-0 Calbiochem | 1 mU/reaction | N-Succinyl-Ala-Pro-Phe-p-nitroanilide Sigma | 1 |
| Trypsin, Iodination grade, from human pancreas, CAS nr. 9002-07-7 Calbiochem | 1 mU/reaction | N-Benzoyl-Arg-p-nitroanilide Sigma | 0.32 |
| Chymase, from human skin Calbiochem | 9 mU/reaction | N-Succinyl-Ala-Pro-Phe-p-nitroanilide Sigma | 1.5 |
| Thrombin, from Human Plasma, high activity, CAS nr. 9002-04-4 Calbiochem | 100 mU/reaction | Benzoyl-Phe-Val-Arg-p-nitroanilide Calbiochem | 0.5 |
| Chymotrypsin, from human pancreas CAS nr 9004-07-3 Calbiochem | 1.6 microM/reaction | N-Succinyl-Ala-Pro-Phe-p-nitroanilide Sigma | 1 |
| Coagulation Factor Xa, from uman plasma, CAS nr. 9002-05-5 Calbiochem | 0.4 mU/reaction | Methoxycarbonyl-D-Nle-Gly-Arg-p-nitroanilid Roche | 2 |
| Tryptase, from human lung Calbiochem | 12.5 mU/reaction | N-Benzoyl-Arg-p-nitroanilide Sigma | 1.28 |
| Urokinase from human urine/Sigma Aldrich CAS nr. 9039-53-6 | 250 mU/reaction | Pyroglu-Gly-Arg-p-nitroanilide × HCl Endotell | 0.5 |
| Kallikrein, from human plasma, CAS Nr 9001-01-8 Calbiochem | 0.34 microgram/reaction | N-Benzoyl-Pro-Phe-Arg-p-nitroanilide Sigma | 1 |

TABLE 2-continued

| Enzyme/ Supplier | Enzyme concentration in assay | Substrate/ Supplier | Substrate concentration in assay (mM) |
|---|---|---|---|
| Plasmin from human plasma, CAS nr. 9001-90-5 Sigma-Aldrich | 2 mU/reaction | D-Val-Leu-Lys-p-Nitroanilide Sigma | 5 |

2.3. Cytotoxicity Assay

The cytotoxicity of the peptides to HELA cells (Acc57) and COS-7 cells (CRL-1651) was determined using the MTT reduction assay [see ref. 2 and 3, below]. Briefly the method was as follows: HELA cells and COS-7 cells were seeded at $7.0 \times 10^3$ and, respectively, $4.5 \times 10^3$ cells per well and grown in 96-well microtiter plates for 24 hours at 37° C. at 5% $CO_2$. At this point, time zero (Tz) was determined by MTT reduction (see below). The supernatant of the remaining wells was discarded, and fresh medium and the peptides in serial dilutions of 12.5, 25 and 50 µM were pipetted into the wells. Each peptide concentration was assayed in triplicate. Incubation of the cells was continued for 48 hours at 37° C. at 5% $CO_2$. Wells were then washed once with phosphate buffered saline (PBS) and subsequently 100 µl MTT reagent (0.5 mg/ml in medium RPMI1640 and, respectively, DMEM) were added to the wells. This was incubated at 37° C. for 2 hours and subsequently the medium was aspirated and 100 µl isopropanol were added to each well. The absorbance at 595 nm of the solubilized product was measured ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100% and was plotted for each peptide concentration.

The LC 50 values (Lethal Concentration, defined as the concentration that kills 50% of the cells) were determined for each peptide by using the trend line function of EXCEL (Microsoft Office 2000) for the concentrations (50, 25, 12.5 and 0 µM), the corresponding growth percentages and the value −50, (=TREND(C50:C0,%50:%0,−50)).

The GI 50 (Growth Inhibition) concentrations were calculated for each peptide by using a trend line function for the concentrations (50, 25, 12.5 and 0 µg/ml), the corresponding percentages and the value 50, (=TREND ($C_{50}$:$C_0$,%$_{50}$:%$_0$, 50).

2.4. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 µM were incubated with 20% v/v hRBC for 1 hour at 37° C. The final erythrocyte concentration was approximately $0.9 \times 10^9$ cells per ml. A value of 0% and, respectively, 100% cell lysis was determined by incubation of the hRBC in the presence of PBS alone and, respectively, 0.1% Triton X-100 in $H_2O$. The samples were centrifuged, the supernatant was 20-fold diluted in PBS buffer and the optical density (OD) of the sample at 540 nM was measured. The 100% lysis value ($OD_{540}H_2O$) gave an $OD_{540}$ of approximately 1.3-1.8. Percent hemolysis was calculated as follows: ($OD_{540}$peptide/ $OD_{540}H_2O$)×100%.

2.5 Plasma Stability

405 µl of plasma/albumin solution were placed in a polypropylene (PP) tube and spiked with 45 µl of compound from a 100 mM solution B, derived from 135 µl of PBS and 15 µl of 1 mM peptide in PBS, pH 7.4. 150 µl aliquots were transferred into individual wells of the 10 kDa filter plate (Millipore MAPPB 1010 Biomax membrane). For "0 minutes controls": 270 µl of PBS were placed in a PP tube and 30 µl of stock solution B was added and vortexed. 150 µl of control solution were placed into one well of the filter plate and served as "filtered control".

Further 150 µl of control solution were placed directly into a receiver well (reserved for filtrate) and served as "not-filtered control". The entire plate including evaporation lid was incubated for 60 min at 37° C. Plasma samples (rat plasma: Harlan Sera lab UK, human plasma: Blutspendezentrum Zürich) were centrifuged at least for 2 h at 4300 rpm (3500 g) and 15° C. in order to yield 100 filtrate. For "serum albumin"-samples (freshly prepared human albumin: Sigma A-4327, rat albumin: Sigma A-6272, all at 40 mg/ml concentration in PBS) approximately 1 hour of centrifugation was sufficient. The filtrates in the receiver PP plate were analysed by LC/MS as follower follows: Column: Jupiter C18 (Phenomenex), mobile phases: (A) 0.1% formic acid in water and (B) acetonitrile, gradient: 5%-100% (B) in 2 minutes, electrospray ionization, MRM detection (triple quadrupole). The peak areas were determined and triplicate values were averaged. The binding was expressed in percent of the (filtered and not-filtered time point 0 min) control 1 and 2 by: 100− (100×$T_{60}$/$T_0$). The average from these values was then calculated.

2.6. Pharmacokinetic Study (PK)

Pharmacokinetic Study after Single Oral (Gavage) and Intravenous Administration in Rats Pharmacokinetic study after single intravenous (i.v.) and oral (p.o., gavage) administration was performed for the compound of Example 75 ("Ex. 75"). 332 g (±10 g) male Wistar mice obtained from RCC Ltd, Laboratory animal Services, CH-4414 Füllinsdorf, Switzerland were used in the study. The vehicle, physiological saline, was added to give a final concentration of 2.5 mg/ml of the compound. The volume was 2 ml/kg i.v. and 10 ml/kg p.o. and the peptide Ex. 75 was injected to give a final intravenous dose of 5 mg/kg and an oral dose of 50 mg/kg. Blood samples (approx. 0.24 ml) were taken following the schedule below at different time points into heparinized tubes by automated blood sampling using the DiLab AccuSampler. When a problem occurred during automated blood sampling, blood was sampled by retro-orbital bleeding under light isoflurane anesthesia. Samples were taken at the following time points: 0, 5 min (only i.v.), 15, 30 min and 1, 2, 4, 8, 16, 24 and 36 (only p.o.) hours and added to heparinized tubes. Plasma was removed from pelleted cells upon centrifugation and frozen at −80° C. prior to HPLC-MS analysis.

Preparation of the Plasma Calibration Samples

"Blank" rat plasma from untreated animals was used. Aliquots of plasma of 0.1 ml each were spiked with 50 ng of propranolol (Internal Standard, IS), (sample preparation by solid phase extraction on OASIS® HLB cartridges (Waters)) and with known amounts of Ex. 75 in order to obtain 9 plasma calibration samples in the range 5-2000 ng/ml. The OASIS® HLB cartridges were conditioned with 1 ml of methanol and then with 1 ml of 1% $NH_3$ in water. Samples were then diluted with 400 μl of 1% $NH_3$ in water and loaded. The plate was washed with 1 ml of methanol/1% $NH_3$ in water 5/95. Elution was performed using 1 ml of 0.1% TFA in methanol.

The plate containing eluates was introduced into the concentrator system and taken to dryness. The residues were dissolved in 100 μl of formic acid 0.1%/acetonitrile, 95/5 (v/v) and analysed in the HPLC/MS on a reverse phase analytical column (Jupiter C18, 50×2.0 mm, 5 μm, Phenomenex), using gradient elution (mobile phases A: 0.1% formic acid in water, B: Acetonitrile; from 5% B to 100% B in 2 min.).

Preparation of Plasma Samples

From each sample 100 μl of plasma were taken for the extraction. If the volume was less than 100 μl the appropriate amount of "blank" mouse plasma was added in order to keep the matrix identical to the calibration curve. Samples were then spiked with IS and processed as described for the calibration curve.

Pharmacokinetic Evaluation

PK analysis was performed on pooled data (generally n=2 or 3) using the software PK solutions 2.0™ (Summit Research Service, Montrose, Colo. 81401 USA). The area under the curve AUC was calculated by the linear trapezoidal rule. $AUC_{(t-\infty)}$ was estimated as Ct/b (b: elimination rate constant). $AUC_{(t-\infty)}$ is the sum of $AUC_{(0-t)}$ and $AUC_{(t-\infty)}$. Elimination half-life was calculated by the linear regression on at least three data points during the elimination phase. The time intervals selected for the half-life determinations were evaluated by the correlation coefficient ($r^2$), which should be at least above 0.85 and most optimally above 0.96. In case of i.v. administration the initial concentration at $t_{zero}$ was determined by extrapolation of the curve through the first two time points. Finally bioavailability after i.p. administration was calculated from the normalised $AUC_{(0-\infty)}$ ratio after i.p. versus i.v. administration.

3.0 Results

The results of the experiments described under 2.2-2.5, above, are indicated in Table 3 herein below.

TABLE 3

| Ex | Cathepsin G IC50 (nmol) | Elastase IC50 (nmol) | Trypsin at 100 μM % | Chymotrypsin at 100 μM % | Chymase at 100 μM % | Thrombin at 100 μM % | FXa at 100 μM % | Urokinase at 100 μM % | Tryptase At 100 μM % | Cytotoxicity $LC_{50}/GI_{50}$ Hela cells | Hemolysis at 100 μM % |
|---|---|---|---|---|---|---|---|---|---|---|---|
| 1 | 86 | >100000 | 92.6 | 7.8 | 0 | 1.1 | 5.7 | 5.7 | 0 | nd | 0 |
| 2 | 84 | >100000 | 92 | 2.9 | 0 | 9.2 | 5.3 | 0.9 | 39.6 | nd | nd |
| 3 | 51 | >100000 | 92 | 0 | 1 | 0 | 4 | 4 | 68 | 100 | 0 |
| 4 | 91 | >100000 | 96 | 1.8 | 0 | 0 | 2.4 | 5.4 | 0 | 100 | 0 |
| 5 | 56 | >100000 | 92 | 3 | 0 | 0.5 | 0.2 | 5.7 | 74 | nd | 0 |
| 6 | ? | nd | nd | nd | nd | nd | nd | nd | nd | nd | nd |
| 7 | 91 | 1.5 at 100 μM % | 41 | 12 | 13.4 | 0 | 11.7 | 1.1 | 1.5 | 100 | 0.2 |
| 8 | 126 | 0.8 at 100 μM % | 74.2 | 5.6 | 71.7 | nd | nd | nd | nd | nd | nd |
| 9 | 105 | 4.1 at 100 μM % | 88.1 | nd | nd | nd | nd | nd | nd | nd | nd |
| 10 | 75 | 0.3 at 100 μM % | 89.9 | nd | 9.4 | nd | nd | nd | nd | nd | nd |
| 11 | 95 | 19 at 100 μM % | 6.5 | 73.6 | 12.1 | nd | nd | nd | nd | nd | nd |
| 12 | 90 | 37038 | 97 | 28 | 12 | 11 | 5 | 12 | 59.3 | 59.3 | nd |
| 13 | 100 | 8.2 at 100 μM % | 95.0 | nd | 19.9 | nd | nd | nd | nd | nd | nd |
| 14 | 52 | >100000 | 88 | 0 | 42.3 | 8.7 | 6 | 5.4 | 84.2 | 100 | 0 |
| 15 | 56.0 | >100000 | 95.0 | 54.2 | 12.7 | nd | nd | nd | nd | 100 | 0 |
| 16 | 66 | >100000 | 90.0 | 17.9 | 12.9 | nd | nd | 3.2 | nd | 94 | 0.1 |
| 17 | 55 | >100000 | 90.0 | 16 | 27.6 | 0 | nd | nd | 90.4 | 94 | 0.1 |
| 18 | 47 | >100000 | 84 | 25 | 32.5 | 0 | nd | nd | 88.3 | 100 | 0 |
| 19 | 41 | >100000 | 94.0 | 0 | 26.9 | 11 | 32 | 4 | 85.2 | 100 | 0 |
| 20 | 48 | >100000 | 97.0 | 0 | 44.1 | 28 | 25 | 6.7 | nd | 100 | 0 |
| 21 | 97 | 16.4 | 95.6 | 2.6 | 5 | nd | nd | nd | nd | nd | nd |
| 22 | 55 | >100000 | 84. | 0 | 98.8 | nd | nd | 5.7 | 3.8 | 8 | 0 |
| 23 | 38 | >100000 | 90 | 4 | 60 | 0 | 11 | 9 | 29 | 51 | 0 |
| 24 | 71 | >100000 | 97 | 1.0 | 1.2 | 3.5 | 30 | 5.1 | 0 | 99 | nd |
| 25 | 102 | 3.2 at 100 μM % | 89.3 | nd | 10.0 | nd | nd | nd | nd | nd | nd |
| 26 | 49 | >100000 | 84 | 2.2 | 0 | 3 | 6 | 3.1 | 66.4 | nd | nd |
| 27 | 48 | nd | nd | nd | nd | nd | nd | nd | nd | nd | nd |
| 28 | 39 | >100000 | 95 | 32 | 0 | 12 | 6 | 1 | 0 | nd | nd |
| 29 | 42 | nd | nd | nd | nd | nd | nd | nd | nd | nd | nd |
| 30 | 39 | 49900 | 98 | 49 | 0 | 2 | 3 | 9 | nd | nd | nd |
| 31 | 34 | >100000 | 98 | 15 | 12 | 10 | 8 | 15 | 76 | nd | nd |
| 32 | 52 | nd | nd | nd | nd | nd | nd | nd | nd | nd | nd |
| 33 | 45 | nd | nd | nd | nd | nd | nd | nd | nd | nd | nd |
| 34 | 56 | nd | nd | nd | nd | nd | nd | nd | nd | nd | nd |
| 35 | 54 | nd | nd | nd | nd | nd | nd | nd | nd | nd | nd |
| 36 | 41 | nd | Nd | nd | nd | nd | nd | 0 | 73.3 | 83 | 0 |
| 37 | 35 | nd | nd | nd | nd | nd | nd | 5 | 56 | 92 | 0.1 |
| 38 | 31 | >100000 | 96 | 4 | 1 | 0 | 0 | 1 | 11 | 100 | 0 |
| 39 | 38 | >100000 | 94 | 7 | 0 | 2 | 0 | 2 | 34 | 98 | 0 |
| 40 | 25 | >44862 | 94 | 19 | 8 | 1 | 3 | 10 | 33 | 97 | 0.1 |
| 41 | 49 | nd | nd | nd | nd | nd | nd | nd | nd | nd | nd |

TABLE 3-continued

| Ex | Cathepsin G IC50 (nmol) | Elastase IC50 (nmol) | Trypsin at 100 μM % | Chymotrypsin IC50 (nmol) | Chymase at 100 μM % | Thrombin at 100 μM % | FXa at 100 μM % | Urokinase at 100 μM % | Tryptase at 100 μM % | Cytotoxicity LC50/GI50 Hela cells | Hemolysis at 100 μM % |
|---|---|---|---|---|---|---|---|---|---|---|---|
| 42 | 46 | nd | nd | nd | nd | nd | nd | 7 | 0 | 87 | 0 |
| 43 | 77 | nd | nd | nd | nd | nd | nd | nd | nd | nd | nd |
| 44 | 31 | >10000 | 100 | 24 | 3 | 9 | 9 | 14 | 50 | 67 | 0.1 |
| 45 | 47 | nd | nd | nd | nd | nd | nd | nd | nd | nd | nd |
| 46 | 87.5 | >100000 | 95 | 0 | 10.2 | 6.9 | 12.2 | 5.8 | 44.1 | nd | nd |
| 47 | 64 | >10000 | 87 | 1 | 8.2 | 0 | 9.3 | 6.3 | 0 | 100 | 0 |
| 48 | 83 | >100000 | 93 | 3 | nd | nd | nd | nd | nd | nd | nd |
| 49 | 82 | >10000 | 96 | 0 | 0 | 7.9 | nd | 6.2 | 30.5 | nd | nd |
| 50 | 89 | >100000 | 94 | 0 | nd | nd | nd | nd | nd | nd | nd |
| 51 | 91 | >100000 | nd | nd | nd | nd | nd | nd | nd | nd | nd |
| 52 | 52 | >100000 | 86 | 0 | 42.3 | 8.7 | 6 | 5.4 | 84.2 | 100 | 0 |
| 53 | 56 | >100000 | 95 | 54 | 12.7 | nd | nd | nd | nd | 63 | 0 |
| 54 | 66 | >100000 | 90 | 18 | 12.9 | nd | nd | 3.2 | nd | nd | 0 |
| 55 | 55 | >100000 | 90 | 16 | 27.6 | nd | nd | nd | 90.4 | 94 | 0.1 |
| 56 | 47 | >100000 | 84 | 25 | 32.5 | 0 | nd | nd | 88.3 | 100 | 0 |
| 57 | 41 | >100000 | 94 | 0 | 26.9 | 11 | 32 | 4 | 82.2 | 0 | 0 |
| 58 | 47.5 | >100000 | 97 | 0 | 44.1 | 28 | 25 | 6.7 | nd | 100 | 0 |
| 59 | 55 | >100000 | 84 | 0 | 98.8 | nd | nd | 5.7 | 3.8 | 8 | 0 |
| 60 | 38 | >100000 | 90 | 4 | 60 | 0 | 11 | 9 | 29.4 | 51 | 0 |
| 61 | 72 | nd | nd | nd | nd | nd | nd | nd | nd | nd | nd |
| 62 | 69 | nd | nd | nd | nd | nd | nd | nd | nd | nd | nd |
| 63 | 41 | >100000 | 96 | 11 | 7 | 1 | 0 | 0 | 50 | 87 | 0 |
| 64 | 45 | >100000 | 87 | 0 | 0 | 2.3 | 0 | 3 | 0 | 59 | 0 |
| 65 | 47 | nd | nd | nd | nd | nd | nd | 1 | 57 | 84 | 0 |
| 66 | 48 | nd | nd | nd | nd | nd | nd | nd | nd | nd | nd |
| 67 | 48 | nd | nd | nd | nd | nd | nd | nd | nd | nd | nd |
| 68 | 59 | >100000 | 84.2 | 4.3 | 0 | 5.4 | 8.6 | 4.6 | 21.3 | nd | nd |
| 69 | 68 | nd | nd | nd | nd | nd | nd | nd | nd | nd | nd |
| 70 | 69 | nd | nd | nd | nd | nd | nd | nd | nd | nd | nd |
| 71 | 70 | nd | nd | nd | nd | nd | nd | nd | nd | nd | nd |
| 72 | 87 | nd | nd | nd | nd | nd | nd | nd | nd | nd | nd |
| 73 | 89 | >100000 | 94 | 0 | nd | nd | nd | nd | nd | nd | Nd |
| 74 | 91 | >10000 | 86 | >100000 | nd | nd | nd | nd | nd | nd | nd |
| 75 | 86 | 69.1 at 100 μM % | 92.6 | 7.8 at 100 μM % | 0 | 1.1 | 5.7 | 5.7 | 0 | nd | nd |
| 76 | nd | 71 | nd | nd | nd | nd | nd | nd | nd | nd | nd |
| 77 | nd | 68 | nd | nd | nd | nd | nd | nd | nd | nd | nd |
| 78 | nd | 29 | nd | <4000 | nd | nd | nd | nd | nd | 61 | nd |
| 79 | nd | 66 | nd | nd | nd | nd | nd | nd | nd | nd | nd |
| 80 | nd | 35 | nd | >20000 | nd | nd | nd | nd | nd | 12 | nd |
| 81 | 61.3 at 100 μM % | 28 | 100000 | 100000 | nd | 13.1 | 8.7 | nd | nd | 58 | nd |
| 82 | nd | 18 | nd | 72.9 | nd | nd | 15.3 | nd | 44.5 | nd | nd |
| 83 | nd | 43 | nd | 100000 | nd | nd | nd | nd | nd | 12 | nd |
| 84 | 20195 | 18 | 10.8 | 17103 | 0 | 20.6 | 13.3 | 10.4 | 4.2 | 9 | nd |
| 85 | nd | 28 | 0 | >20000 | nd | 12.6 | 25.6 | nd | nd | nd | nd |
| 86 | 47 at 100 μM % | 26 | 0 | >100000 | 0 | 10.7 | 24.8 | nd | 0 | nd | nd |
| 87 | nd | 37 | nd | 106977 | nd | nd | nd | nd | nd | 65 | nd |
| 88 | >100000 | 18 | 6.4 | 4309 | 0 | 0.2 | 3 | 96 | 0.6 | 73 | nd |
| 89 | nd | 43 | nd | nd | nd | nd | nd | nd | nd | 51 | nd |
| 90 | 66975 | 21 | 5.2 | 33074 | 0 | 0 | 5.5 | 3.5 | 5 | 96 | nd |
| 91 | 45 at 100 μM % | 28 | 0 | 48108 | 4.7 | 13.5 | 19.4 | nd | nd | 79 | nd |
| 92 | nd | 43 | nd | nd | nd | nd | nd | nd | nd | 93 | nd |
| 93 | nd | 41 | nd | nd | nd | nd | nd | nd | 5.6 | 100 | nd |
| 94 | nd | 50 | nd | nd | nd | nd | nd | nd | nd | nd | nd |
| 95 | 38677 | 24 | 8.9 | 33729 | 0 | 0 | 11.3 | 10.3 | 0 | 89 | nd |
| 96 | 21175 | 15 | 7.5 | 15433 | 0 | 3.6 | 0 | 6.2 | 0 | 52 | nd |
| 97 | >100000 | 24 | 9.5 | 77431 | 0 | 11.6 | 4.8 | 11.9 | 0 | 100 | nd |
| 98 | >100000 | 21 | 0 | 38820 | 0 | 5.2 | 0 | 0 | 0 | 78 | nd |
| 99 | 85196 | 16 | 30.5 | 8558 | 0 | 0 | 0 | 17.4 | 0 | 58 | nd |
| 100 | nd | 35 | nd | nd | nd | nd | nd | nd | nd | 83 | nd |
| 101 | nd | 49 | nd | nd | nd | nd | nd | nd | nd | nd | nd |
| 102 | >100000 | 13 | 0 | 4975 | 0 | 1.7 | 0 | 0.5 | 0 | 55 | nd |
| 103 | >100000 | 18 | 6.4 | 4309 | 0 | 10.2 | 3 | 9.6 | 0.6 | 47 | nd |
| 104 | 53.5 at 100 μM % | 34 | 0 | 3.1 at 100 μM % | 0 | 7.7 | 6.2 | 0 | 0 | nd | nd |
| 105 | nd | 34 | nd | nd | nd | nd | nd | nd | nd | nd | nd |
| 106 | nd | 49 | nd | nd | nd | nd | nd | nd | nd | nd | nd |
| 107 | nd | 51 | nd | nd | nd | nd | nd | nd | nd | nd | nd |
| 108 | nd | 31 | nd | nd | nd | nd | nd | nd | nd | nd | nd |
| 109 | 54.1 at 100 μM % | 33 | 0 | 13.8 | 0.1 | 0 | 5.6 | nd | nd | nd | nd |

TABLE 3-continued

| Ex | Cathepsin G IC50 (nmol) | Elastase IC50 (nmol) | Trypsin at 100 µM % | Chymotrypsin at 100 µM % | Chymase at 100 µM % | Thrombin at 100 µM % | FXa at 100 µM % | Urokinase at 100 µM % | Tryptase at 100 µM % | Cytotoxicity LC$_{50}$/GI$_{50}$ Hela cells | Hemolysis at 100 µM % |
|---|---|---|---|---|---|---|---|---|---|---|---|
| 110 | nd | 38 | nd | nd | nd | nd | nd | nd | nd | nd | nd |
| 111 | nd | 46 | nd | nd | nd | nd | nd | nd | nd | nd | nd |
| 112 | nd | 39 | nd | nd | nd | nd | nd | nd | nd | 33 | nd |
| 113 | nd | 35 | nd | nd | nd | nd | nd | nd | nd | nd | nd |
| 114 | nd | 47 | nd | nd | nd | nd | nd | nd | nd | 34 | nd |
| 115 | nd | 38 | nd | 27751 | nd | nd | nd | nd | nd | 51 | nd |
| 116 | nd | 46 | 0 | 39710 | nd | nd | nd | nd | nd | nd | nd |
| 117 | nd | 33 | nd | nd | nd | nd | nd | nd | nd | 29 | nd |
| 118 | nd | 43 | nd | nd | nd | nd | nd | nd | nd | nd | nd |
| 119 | nd | 45 | nd | nd | nd | nd | nd | nd | nd | nd | nd |
| 120 | nd | 29 | nd | nd | nd | nd | nd | nd | nd | 38 | nd |
| 121 | 11155 | 18 | 12.8 | 27526, IC50 (nmol) | 1.2 | 0 | 5.6 | 5.7 | 4.6 | 49 | nd |
| 122 | 35134 | 18 | 19 | 58000, IC50 (nmol) | 6.4 | 0 | 19.6 | 11.1 | 0.2 | 29 | nd |
| 123 | 35203 | 14 | 7.9 | 14995, IC50 (nmol) | 0 | 2.7 | 0 | 7.6 | nd | nd | nd |
| 124 | nd | 40 | nd | nd | nd | nd | nd | nd | nd | 40 | nd |
| 125 | 18269 | 15 | 28.3 | >20000, IC50 (nmol) | 4.8 | 0 | 0 | nd | nd | 37 | nd |
| 126 | nd | 36 | nd | nd | nd | nd | nd | nd | nd | nd | nd |
| 127 | 64 at 100 µM % | 29 | 0 | 47.2 | 1.9 | 3.7 | 13.3 | nd | 0 | nd | nd |
| 128 | nd | 40 | nd | nd | nd | nd | nd | nd | nd | nd | nd |
| 129 | nd | 30 | nd | nd | nd | nd | nd | nd | nd | nd | nd |
| 130 | nd | 29 | nd | nd | <4000 | nd | nd | nd | nd | nd | nd |
| 131 | 45 | 28 | 0 | nd | 46108 | nd | nd | nd | nd | nd | nd |
| 132 | nd | 26 | nd | nd | nd | nd | nd | nd | nd | nd | nd |
| 133 | nd | 26 | nd | nd | nd | nd | nd | nd | nd | nd | nd |
| 134 | nd | 23 | nd | nd | nd | nd | nd | nd | nd | nd | nd |
| 135 | nd | 23 | nd | nd | nd | nd | nd | nd | nd | nd | nd |
| 136 | >100000 | 21 | 0 | 67.9 | 0 | 5.2 | 0 | 0 | 0 | nd | nd |
| 137 | 66975 | 21 | 5.2 | 68.7 | 0 | 0 | 5.5 | 3.5 | 5 | nd | nd |
| 138 | 43856 | 19 | 12.2 | 77.1 | 4.6 | 17.1 | 12.6 | 14.4 | 0 | nd | nd |
| 139 | nd | 18 | nd | nd | nd | nd | nd | nd | nd | nd | nd |
| 140 | 20195 | 18 | 10.8 | 79.6 | 0 | 20.6 | 13.3 | 10.4 | 4.2 | nd | nd |
| 141 | 63.4 at 100 µM % | 18 | 0 | 72.9 | 0 | 0 | 15.3 | nd | 44.5 | 56 | nd |
| 142 | nd | 16 | nd | nd | nd | nd | nd | nd | nd | nd | nd |
| 143 | 28 at 100 µM % | 15 | 12 | 91 | 0 | 12 | 0 | 8 | 18 | nd | nd |
| 144 | 21175 | 7.5 | 7.5 | 80.6 | 0 | 3.6 | 0 | 6.2 | 0 | nd | nd |
| 145 | nd | 14 | nd | nd | nd | nd | nd | nd | nd | nd | nd |
| 146 | 1 at 100 µM % | 12 | 3 | 87 | 0 | 11 | 1 | 0 | 22 | nd | nd |
| 147 | nd | 11 | nd | nd | nd | nd | nd | nd | nd | nd | nd |
| 148 | 52 at 100 µM % | 11 | 9 | 91 | 7 | 32 | 8 | 12 | 30 | nd | nd |
| 149 | nd | 11 | nd | nd | nd | nd | nd | nd | nd | nd | nd |
| 150 | nd | 10 | nd | nd | nd | nd | nd | nd | nd | nd | nd |
| 151 | nd | 10 | nd | nd | nd | nd | nd | nd | nd | nd | nd |
| 152 | nd | 9 | nd | nd | nd | nd | nd | nd | nd | nd | nd |
| 153 | 56 at 100 µM % | 8.5 | 8 | 84 | 0 | 16 | 11 | 16 | 9 | nd | nd |
| 154 | 27 at 100 µM % | 8.3 | 0 | 4 | 0 | 7 | 0 | 1 | 15 | nd | nd |
| 155 | 52 at 100 µM % | 8.2 | 18 | 83 | 3 | 19 | 9 | 12 | 30 | nd | nd |
| 156 | 46 at 100 µM % | 7.5 | 0 | 5 | 0 | 17 | 0 | 7 | 15 | nd | nd |
| 157 | nd | 7 | nd | nd | nd | nd | nd | nd | nd | nd | nd |
| 158 | 55 at 100 µM % | 7.1 | 8 | 93 | 0 | 2 | 1 | 10 | 13 | nd | nd |
| 159 | nd | 7 | nd | nd | nd | nd | nd | nd | nd | nd | nd |
| 160 | 55 at 100 µM % | 6 | 3 | 94 | 2 | 23 | 1 | 14 | 30 | nd | nd |
| 161 | nd | 6 | nd | nd | nd | nd | nd | nd | nd | nd | nd |
| 162 | nd | 12.5 | nd | nd | nd | nd | nd | nd | nd | nd | nd |
| 163 | nd | 24 | nd | nd | nd | nd | nd | nd | nd | nd | nd |
| 164 | nd | 24 | nd | nd | nd | nd | nd | nd | nd | nd | nd |
| 165 | nd | 22 | nd | nd | nd | nd | nd | nd | nd | nd | nd |
| 166 | nd | 18 | nd | nd | nd | nd | nd | nd | nd | nd | nd |
| 167 | 35134 | 18 | 19 | 60.2 | 6.4 | 0 | 19.6 | 11.1 | 0.2 | nd | nd |
| 168 | 11155 | 18 | 12.8 | 72.9 | 1.2 | 0 | 5.6 | 5.7 | 4.6 | nd | nd |
| 169 | 20295 | 18 | 10.8 | 79.6 | 0 | 20.6 | 13.3 | 10.4 | 4.2 | nd | nd |

TABLE 3-continued

| | | | | | | | | | | | |
|---|---|---|---|---|---|---|---|---|---|---|---|
| 170 | nd | 16 | nd | nd | nd | nd | nd | nd | nd | nd | nd |
| 171 | nd | 13 | nd | nd | nd | nd | nd | nd | nd | nd | nd |
| 172 | nd | 13 | nd | nd | nd | nd | nd | nd | nd | nd | nd |
| 173 | nd | 12 | nd | nd | nd | nd | nd | nd | nd | nd | nd |
| 174 | 56 at 100 µM % | 12 | 7 | 85 | 0 | 11 | 3 | 1 | 10 | nd | nd |
| 175 | nd | 12 | nd | nd | nd | nd | nd | nd | nd | nd | nd |
| 176 | 69 at 100 µM % | 10.3 | 7 | 55 | 2 | 15 | 1 | 8 | 17 | nd | nd |
| 177 | 54 at 100 µM % | 7 | 5 | 86 | 3 | 17 | 7 | 12 | 15 | nd | nd |
| 178 | nd | 6 | nd | nd | nd | nd | nd | nd | nd | nd | nd |
| 179 | nd | 50 | >100000, IC50 (nmol) | 76.0 | nd | nd | nd | nd | 0 | nd | nd |

| Ex | Cathepsin G IC50 (nmol) | Elastase IC50 (nmol) | Trypsin IC50 (nmol) | Chymotrypsin at 100 µM % | Chymase at 100 µM % | Thrombin at 100 µM % | FXa at 100 µM % | Urokinase at 100 µM % | Tryptase IC50 (nmol) | Cytotoxicity $LC_{50}/GI_{50}$ Hela cells | Hemolysis at 100 µM % |
|---|---|---|---|---|---|---|---|---|---|---|---|
| 180 | 120 | nd | 60 | nd | nd | nd | nd | nd | <100 | nd | nd |
| 181 | 127 | nd | 113 | nd | nd | nd | nd | nd | 40 | nd | nd |
| 182 | 111 | nd | 59 | nd | nd | nd | nd | nd | 39 | nd | nd |
| 183 | 243 | nd | 146 | nd | nd | nd | nd | nd | 25 | nd | nd |
| 184 | 221 | nd | 48 | nd | nd | nd | nd | nd | 27 | nd | nd |
| 185 | 514 | nd | 126 | nd | nd | nd | nd | nd | 14 | nd | nd |
| 186 | 337 | nd | 99 | nd | nd | nd | nd | nd | 15 | nd | nd |
| 187 | 158 | nd | 39 | nd | nd | nd | nd | nd | <100 | nd | nd |
| 188 | 105 | nd | 34 | nd | nd | nd | nd | nd | <100 | nd | nd |
| 189 | 164 | nd | 39 | nd | nd | nd | nd | nd | <100 | nd | nd |
| 190 | 1500 | nd | 172 | nd | nd | nd | nd | nd | <100 | nd | nd |
| 191 | 400 | nd | 66 | nd | nd | nd | nd | nd | 21 | nd | nd |
| 192 | 650 | nd | 72 | nd | nd | nd | nd | nd | 16 | nd | nd |
| 193 | 431 | nd | 35 | nd | nd | nd | nd | nd | 6 | nd | nd |
| 194 | 1570 | nd | 431 | nd | nd | nd | nd | nd | 9 | nd | nd |
| 195 | 4000 | nd | 108 | nd | nd | nd | nd | nd | 12 | nd | nd |
| 196 | 2165 | nd | 70 | nd | nd | nd | nd | nd | 52 | nd | nd | nd: not determined

The results of the experiment described in 2.5 above are indicated in Table 4 herein below.

TABLE 4

| Ex. | Stability human Plasma $t_{1/2}$ (min) | Stability rat Plasma $t_{1/2}$ (min) |
|---|---|---|
| 22 | 300 | 300 |
| 23 | 300 | 300 |
| 75 | 300 | 300 |
| 121 | 300 | 300 |
| 158 | 300 | 300 |

The results of the experiment described in 2.6 (PK), above, are indicated in Table 5 herein below.

TABLE 5

| Administration route | Intravenous | Oral |
|---|---|---|
| Dose (mg/kg) | 5 | 50 |
| $Dose_{norm}$ (mg/kg) | 5 | 5 |
| $AUC_{0-t}$ (ng · h/ml) | 6044 | 782 |
| $AUC_{0-\infty}$ (ng · h/ml) | 6047 | 813 |
| $AUC_{0-\infty\ norm}$ (ng · h/ml) | 6047 | 81 |
| $T_{max\ observed}$ (hours) | 10752 | 464 |
| $T_{max\ norm}$ (hours) | 10752 | 46 |
| $C_{max\ norm}$ (ng/ml) | 0.08 | 0.25 |
| β (hours$^{-1}$) | | |
| Terminal $t_{1/2}$ (hours) | 0.5 | 0.87 |
| Vd (ml/kg) | 547 | 1008 |
| % absorbed (F) (percentage of normalized $AUC_{0-\infty}$ po. against normalized $AUC_{0-\infty}$ i.v.) | 100% | 1.3% |

The large inter-individual variation in plasma concentration of Ex. 75 was most pronounced after single oral administration (for i.v.: % C.V=6-68%, except for one value at the lowest measurable concentration 173%; for p.o. % C.V.: 113-173%).

Intravenous Administration

After intravenous administration of Ex. 75 at a dose level of 5 mg/kg body weight, Ex. 75 followed intravenous kinetic characteristics. After PK analysis, Ex 75 showed an extrapolated $C_{initial}$ of 14069 ng/ml and a $C_{max}$ observed of 10762 ng/ml at 5 min (0.083 hour). Plasma levels rapidly decreased to 5774 and 3455 ng/ml at 15 min and 30 min, respectively. From 1 to 2 hours plasma levels decreased with a terminal $t_{1/2}$ of 0.46 hours to 18 ng/ml at 4 hours. The $AUC_{0-t}$ and $AUC_{0-infinite}$ amounted to 6044 and 6047 ng×h/ml, respectively; the initial distribution volume amounted to 355 ml/kg. The apparent distribution volume was 547 ml/kg.

Oral Administration

Alter oral administration of Ex 75 at a dose level of 50 mg/kg body weight, plasma levels of Ex. 75 followed oral kinetic characteristics. After PK analysis, Ex. 75 showed an observed $C_{max}$ of 464 ng/ml at 0.25 hour (15 min). From 0.25 hours, plasma levels decreased with a terminal $t_{1/2}$ of 0.87 hours to 24 ng/ml at 4 hours. The $AUC_{0-t}$ and $AUC_{0-infinite}$ amounted to 782 and 813 ng×h/ml. respectively. Taking into account the absorption of 1.3%, the apparent distribution volume was 1008 ml/kg.

Oral Versus Intravenous Administration

Due to the different dose levels between the oral group versus the i.v. group, values were compared after dose normalisation.

Compared to the normalized AUC$_{0\text{-}infinite}$ value after i.v. administration of Ex. 75 (100%: 6047 ng-h/ml), the percentage of Ex. 75 absorbed (F) after oral administration amounted to 1.3% (81 ngxh/ml) at an about 234 times lower normalised C$_{max}$ value after oral administration (46 versus 10762 ng/ml; Table 3). The apparent distribution volume after oral administration was about 1.8 fold higher than after i.v. administration (1008 versus 547 ml/kg).

REFERENCES

1. Barrtt, A. J. Methods in Enzymology 1981, 80, 561-565; Leatherbarrow, R. J. 1992, *GraFit*, Erithacus Software Ltd., Staines, U.K.
2. Mossman T. *J. Immunol. Meth.* 1983, 65:55-63
3. Berridge M V, Tan A S. *Arch. Biochem. Biophys.* 1993, 303:474-482

---

The invention claimed is:

1. A compound of the formula (I):

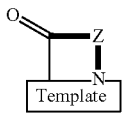

in which

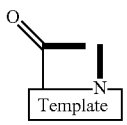

is a dipeptide made up of two different amino acid building blocks, the dipeptide being $^D$Pro-$^L$Pro, and Z is an undecapeptide chain made up of eleven amino acid residues, in which P1 is selected from Nle, Ile, Aoc, hLeu, Chg, OctG, hPhe, 4AmPhe, Cha, Phe, Tyr, 2Cl-Phe, Trp, 1-NaI, or Leu;
P2 is selected from Cys, Glu, Nle, Thr, or Gln;
P3 is selected from Thr, Ala, or Abu;
P4 is selected from Lys, Nle, Ala, Abu, or Thr;
P5 is selected from Ser, AlloThr, or Dpr;
P6 is selected from Ile, C$_5$al, Leu, Nle, Aoc, OctG, Cha, hLeu, hPhe, Chg, t-BuA, Glu, or Asp;
P7 is Pro;
P8 is selected from Pro, Ala, or Pro(4NHCOPhe);
P9 is selected from Tyr, Phe, Be, Nle, Cha, Gln, Arg, Lys, His, or Thr;
P10 is selected from Cys, Arg, Nle, Gln, Lys, Met, Thr, or Ser; and
P11 is selected from Tyr, Gln, Arg, Ser, Nle, 2-NaI, 2Cl-Phe, Cha, Phg, Phe, Asp, Asn, or Thr, two residues of Cys, which are present as the P2 and the P10 residues, being linked by a disulfide bridge formed by replacement of the two —SH groups in the two residues of Cys by one —S—S— group, in free form, an enantiomer or in a pharmaceutically acceptable salt form.

2. A compound according to claim 1, in which, in the said undecapeptide chain,

P1 is selected from Phe, hPhe, 4AmPhe, Nle, Chg, Ile, Tyr, Trp, 2Cl-Phe, 1-NaI, or Cha;
P2 is selected from Cys, Glu, or Nle;
P3 is Thr;
P4 is selected from Lys, or Nle;
P5 is selected from Ser, AlloThr, or Dpr;
P6 is selected from Asp, or Glu;
P8 is Pro;
P9 is selected from Ile, Nle, Cha, Gln, or Tyr;
P10 is selected from Cys, Arg, or Nle; and
P11 is selected from Thr, Asp, Ser, Tyr, Phe, Asn, or Arg.

3. A compound according to claim 1, in which, in the said undecapeptide chain,

P1 is selected from Ile, Nle, Aoc, hLeu, Chg, OctG, or hPhe;
P2 is selected from Cys, Glu, Thr, or Gln;
P3 is selected from Thr, Ala, or Abu;
P4 is selected from Ala, Thr, or Abu;
P5 is Ser;
P6 is selected from OctG, Ile, Cha, Leu, C$_5$al, Nle, Aoc, Chg, t-BuA, or hLeu;
P8 is selected from Pro, or Pro(4NHCOPhe);
P9 is selected from Gln, Tyr, Ile, or Phe;
P10 is selected from Cys, Lys, Gln, Thr, Met, or Arg; and
P11 is selected from Tyr, Ser, Arg, Gln, Nle, 2-NaI, 2Cl-Phe, Phe, Cha, or Phg.

4. A compound according to claim 1, in which, in the said undecapeptide chain,

P1 is selected from Cha, Tyr, or Trp;
P2 is Cys;
P3 is Thr;
P4 is Lys;
P5 is Ser;
P6 is Leu;
P8 is Pro;
P9 is Lys;
P10 is Cys; and
P11 is Arg.

5. A compound according to claim 1, in which, in the said undecapeptide chain,

P1 is Phe;
P2 is Cys;
P3 is Thr;
P4 is Lys;
P5 is Ser;
P6 is Asp;

P8 is Pro;
P9 is Ile;
P10 is Cys; and
P11 is Tyr.

6. A compound according to claim 1, in which, in the said undecapeptide chain,
P1 is Ile;
P2 is Cys;
P3 is Thr;
P4 is Lys;
P5 is Ser;
P6 is Asp;
P8 is Pro;
P9 is Nle;
P10 is Cys; and
P11 is Arg.

7. A compound according to claim 1, in which, in the said undecapeptide chain,
P1 is Ile;
P2 is Cys;
P3 is Thr;
P4 is Lys;
P5 is Ser;
P6 is Asp;
P8 is Pro;
P9 is Cha;
P10 is Cys; and
P11 is Arg.

8. A compound according to claim 1, in which, in the said undecapeptide chain,
P1 is Ile;
P2 is Cys;
P3 is Thr;
P4 is Nle;
P5 is Ser;
P6 is Asp;
P8 is Pro;
P9 is Ile;
P10 is Cys; and
P11 is Arg.

9. A compound according to claim 1, in which, in the said undecapeptide chain,
P1 is Phe;
P2 is Cys;
P3 is Thr;
P4 is Nle;
P5 is Ser;
P6 is Asp;
P8 is Pro;
P9 is Ile;
P10 is Cys; and
P11 is Tyr.

10. A compound according to claim 1, in which, in the said undecapeptide chain,
P1 is Chg;
P2 is Cys;
P3 is Thr;
P4 is Lys;
P5 is Ser;
P6 is Asp;
P8 is Pro;
P9 is Ile;
P10 is Cys; and
P11 is Tyr.

11. A compound according to claim 1 of the formula I, in which, in the said undecapeptide chain,
P1 is Nle;
P2 is Cys;
P3 is Thr;
P4 is Ala;
P5 is Ser;
P6 is Ile;
P8 is Pro;
P9 is Gln;
P10 is Cys; and
P11 is Gln.

12. A compound according to claim 1, in which, in the said undecapeptide chain,
P1 is Nle;
P2 is Cys;
P3 is Thr;
P4 is Ala;
P5 is Ser;
P6 is Ile;
P8 is Pro;
P9 is Gln;
P10 is Cys; and
P11 is Tyr.

13. A compound according to claim 1, in which, in the said undecapeptide chain,
P1 is hPhe;
P2 is Cys;
P3 is Thr;
P4 is Ala;
P5 is Ser;
P6 is OctG;
P8 is Pro;
P9 is Gln;
P10 is Cys; and
P11 is Gln.

14. A compound according to claim 1, in which, in the said undecapeptide chain,
P1 is OctG;
P2 is Gln;
P3 is Thr;
P4 is Ala;
P5 is Ser;
P6 is Ile;
P8 is Pro;
P9 is Gln;
P10 is Thr; and
P11 is Tyr.

15. A compound according to claim 1, in which, in the said undecapeptide chain,
P1 is hPhe;
P2 is Cys;
P3 is Thr;
P4 is Ala;
P5 is Ser;
P6 is Cha;
P8 is Pro;
P9 is Gln;
P10 is Cys; and
P11 is Phe.

16. A compound according to claim 1, in which, in the said undecapeptide chain,
P1 is OctG;
P2 is Glu;
P3 is Thr;
P4 is Ala;
P5 is Ser;

P6 is Ile;
P8 is Pro;
P9 is Gln;
P10 is Lys; and
P11 is Tyr.
17. A compound according to claim 1, in which, in the said undecapeptide chain,
P1 is OctG;
P2 is Cys;
P3 is Thr;
P4 is Ala;
P5 is Ser;
P6 is Cha;
P8 is Pro;
P9 is Gln;
P10 is Cys; and
P11 is Phe.
18. A compound according to claim 1, in which, in the said undecapeptide chain,
P1 is hPhe;
P2 is Cys;
P3 is Thr;
P4 is Ala;
P5 is Ser;
P6 is Cha;
P8 is Pro;
P9 is Gln;
P10 is Cys; and
P11 is Gln.
19. A compound according to claim 1, in which, in the said undecapeptide chain,
P1 is OctG;
P2 is Cys;
P3 is Thr;
P4 is Ala;
P5 is Ser;
P6 is Cha;
P8 is Pro(4NHCOPhe);
P9 is Gln;
P10 is Cys; and
P11 is Gln.
20. A compound according to claim 1, in which, in the said undecapeptide chain,
P1 is hPhe;
P2 is Cys;
P3 is Thr;
P4 is Ala;
P5 is Ser;
P6 is OctG;
P8 is Pro;
P9 is Gln;
P10 is Cys; and
P11 is Tyr.
21. A compound according to claim 1, in which, in the said undecapeptide chain,
P1 is Chg;
P2 is Cys;
P3 is Thr;
P4 is Lys;
P5 is Ser;
P6 is Asp;
P8 is Pro;
P9 is Ile;
P10 is Cys; and
P11 is Thr.
22. A compound according to claim 1, in which, in the said undecapeptide chain,
P1 is Chg;
P2 is Cys;
P3 is Thr;
P4 is Lys;
P5 is Ser;
P6 is Asp;
P8 is Pro;
P9 is Ile;
P10 is Cys; and
P11 is Asp.
23. A compound according to claim 1, in which, in the said undecapeptide chain,
P1 is OctG;
P2 is Cys;
P3 is Thr;
P4 is Ala;
P5 is Ser;
P6 is Cha;
P8 is Pro;
P9 is Gln;
P10 is Cys; and
P11 is Gln.
24. A compound according to claim 1, in which, in the said undecapeptide chain,
P1 is OctG;
P2 is Cys;
P3 is Thr;
P4 is Ala;
P5 is Ser;
P6 is Ile;
P8 is Pro;
P9 is Gln;
P10 is Cys; and
P11 is Tyr.
25. A compound according to claim 1, in which, in the said undecapeptide chain,
P1 is OctG;
P2 is Cys;
P3 is Thr;
P4 is Ala;
P5 is Ser;
P6 is OctG;
P8 is Pro;
P9 is Gln;
P10 is Cys; and
P11 is Gln.
26. A compound according to claim 1, in which, in the said undecapeptide chain,
P1 is Cha;
P2 is Cys;
P3 is Thr;
P4 is Lys;
P5 is Ser;
P6 is Leu;
P8 is Pro;
P9 is Lys;
P10 is Cys; and
P11 is Arg.
27. A compound according to claim 1, in which, in the said undecapeptide chain,
P1 is Tyr;
P2 is Cys;
P3 is Thr;
P4 is Lys;
P5 is Ser;
P6 is Leu;
P8 is Pro;

P9 is Lys;
P10 is Cys; and
P11 is Arg.

28. A compound according to claim 1, in which, in the said undecapeptide chain,
P1 is Trp;
P2 is Cys;
P3 is Thr;
P4 is Lys;
P5 is Ser;
P6 is Leu;
P8 is Pro;
P9 is Lys;
P10 is Cys; and
P11 is Arg.

29. A pharmaceutical composition comprising the compound according to claim 1 as active ingredient and a pharmaceutically acceptable carrier.

30. A pharmaceutical composition according to claim 29, in a form suitable for oral, buccal, rectal, vaginal, topical, transdermal, transmucosal, pulmonary, injection, inhalation or implantation administration.

31. A pharmaceutical composition according to claim 30, in the form of a tablet, a dragee, a capsule, a lozenge, a pill, a powder, a liquid, a solution, a syrup, an elixir, a slurry, a suspension, an emulsion, a gel, a cream, an ointment, a plaster, a spray, a nebulizer, an inhaler, an insufflator, a suppository, a sustained-release system, a long acting formulation, a depot preparation or a liposome.

32. A compound of the formula (I):

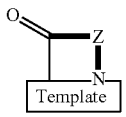

in which

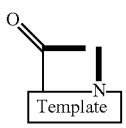

is a dipeptide made up of two different amino acid building blocks, the dipeptide being $^D$Pro-$^L$Gln, and
Z is an undecapeptide chain made up of eleven amino acid residues, in which P1 is Nle;
P2 is Cys;
P3 is Thr;
P4 is Ala;
P5 is Ser;
P6 is Ile;
P7 is Pro;
P8 is Pro;
P9 is Gln;
P10 is Cys; and
P11 is Tyr,
two residues of Cys, which are present as the P2 and the P10 residues, being linked by a disulfide bridge formed by replacement of the two —SH groups in the two residues of Cys by one —S—S— group, in free form or in pharmaceutically acceptable salt form.

33. A compound of the formula (I):

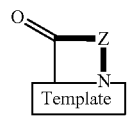

in which

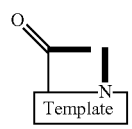

is a dipeptide made up of two different amino acid building blocks, the dipeptide being $^D$Pro-$^L$Gln, and
Z is an undecapeptide chain made up of eleven amino acid residues, in which
P1 is OctG;
P2 is Cys;
P3 is Thr;
P4 is Ala;
P5 is Ser;
P6 is Be;
P7 is Pro;
P8 is Pro;
P9 is Gln;
P10 is Cys; and
P11 is Tyr,
two residues of Cys, which are present as the P2 and the P10 residues, being linked by a disulfide bridge formed by replacement of the two —SH groups in the two residues of Cys by one —S—S— group, in free form or in pharmaceutically acceptable salt form.

34. A compound of the formula (I):

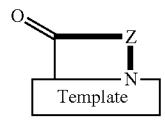

in which

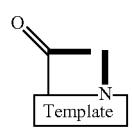

is a dipeptide made up of two different amino acid building blocks, the dipeptide being $^D$Pro-$^L$Gln, and
Z is an undecapeptide chain made up of eleven amino acid residues, in which
P1 is OctG;
P2 is Cys;
P3 is Thr;
P4 is Ala;
P5 is Ser;
P6 is OctG;
P7 is Pro;

P8 is Pro;
P9 is Gln;
P10 is Cys; and
P11 is Gln,
two residues of Cys, which are present as the P2 and the P10 residues, being linked by a disulfide bridge formed by replacement of the two —SH groups in the two residues of Cys by one —S—S— group, in free form or in pharmaceutically acceptable salt form.

35. A compound of the formula (I):

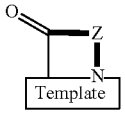

in which

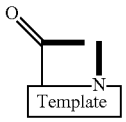

is a dipeptide made up of two different amino acid building blocks, the dipeptide being $^{D}$Pro-$^{L}$Asp, and Z is an undecapeptide chain made up of eleven amino acid residues, in which P1 is Nle;
P2 is Cys;
P3 is Thr;
P4 is Ala;
P5 is Ser;
P6 is Ile;
P7 is Pro;
P8 is Pro;
P9 is Gln;
P10 is Cys; and
P11 is Tyr,
two residues of Cys, which are present as the P2 and the P10 residues, being linked by a disulfide bridge formed by replacement of the two —SH groups in the two residues of Cys by one —S—S— group, in free form or in pharmaceutically acceptable salt form.

* * * * *

UNITED STATES PATENT AND TRADEMARK OFFICE
CERTIFICATE OF CORRECTION

| | | |
|---|---|---|
| PATENT NO. | : 8,658,604 B2 | Page 1 of 1 |
| APPLICATION NO. | : 11/816589 | |
| DATED | : February 25, 2014 | |
| INVENTOR(S) | : Demarco et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1245 days.

Signed and Sealed this
Twenty-first Day of July, 2015

Michelle K. Lee
*Director of the United States Patent and Trademark Office*